United States Patent [19]
Douglas et al.

[11] Patent Number: 5,821,353
[45] Date of Patent: Oct. 13, 1998

[54] DNA ENCODING 1,3 BETA-D GLUCAN SYNTHASE SUBUNITS

[75] Inventors: Cameron M. Douglas, Piscataway; Gary L. Chrebet, Princeton; Joseph Clemas, Metuchen; Mohammed El-Sherbeini, Westfield, all of N.J.; Forrest Foor, New York, N.Y.; Jennifer Nielsen Kahn, East Brunswick, N.J.; Rosemarie Kelly, Westfield, N.J.; Jean A. Marrinan, Somerset, N.J.; Nancy R. Morin, Cranford, N.J.; Janet C. Onishi, Westfield, N.J.; Stephen Authur Parent, Cranbury, N.J.; Naasa M. Ramadan, Westfield, N.J.; Elizabeth A. Register, Scotch Plains, N.J.; Gan-Ju Shei, Plainsboro, N.J.

[73] Assignee: Merck & Co., Inc., Rahway, N.J.

[21] Appl. No.: 619,554

[22] PCT Filed: Oct. 11, 1994

[86] PCT No.: PCT/US94/11498

§ 371 Date: Aug. 1, 1996

§ 102(e) Date: Aug. 1, 1996

[87] PCT Pub. No.: WO95/10625

PCT Pub. Date: Apr. 20, 1995

Related U.S. Application Data

[63] Continuation-in-part of Ser. No. 135,148, Oct. 12, 1993, abandoned, Ser. No. 135,149, Oct. 12, 1993, abandoned, and Ser. No. 135,150, Oct. 12, 1993, abandoned.

[51] Int. Cl.$^6$ .............................. C07H 21/04; C12N 1/15; C12P 21/02; C07K 14/395
[52] U.S. Cl. ................. 536/23.74; 435/69.1; 435/252.3; 435/254.11; 435/320.1; 435/325; 530/350
[58] Field of Search .............................. 536/23.1, 23.74; 435/254.11, 320.1, 325, 69.1, 172.3, 172.1, 252.3; 530/350

[56] References Cited

U.S. PATENT DOCUMENTS 5,194,600 3/1993 Bussey et al. ..................... 536/23.74

OTHER PUBLICATIONS

Font, et al., "Isolation and Characterization of *Saccharomyces Cerevisiae* Mutants Resistant to Aculeacin A," Antimicrobial Agents and Chemotherapy, Dec. 1991, pp. 2596–2601, vol. 35, No. 12.

Duran, et al., "Characterication of genes involved in yeast cell wall synthesis: an attempt to find novel targets for antifungal agents," Profiles on Biotechnology, pp. 221–232 (1992).

Mason, et al., "Disruption of a gene that confers resistance to aculeacin A"; Yeast Cell Biology, Aug. 15–Aug. 20, 1989, p. 154, Cold Spring Harbor Lab., Cold Spring Harbor, NY.

Roemer, et al., "Yeast Beta glucan synthesis KRE6 encodes a predicted type II membrane protein required . . . ," Proc. Natl. Acad. Sci., 88, pp. 11295–11299, Dec. 1991.

Ribas, et al., "Isolation and Characterization of *Schizosaccharomyces pombe* Mutants Defective in Cell Wall . . . ," J. of Bacteriology, pp. 3456–3462, vol. 173, No. 11, (1992).

Diaz, et al., "Isolation and Characterization of *Schizosaccharomyces pombe* Mutants Defective on Cell Wall . . . ," S188 15th Int. Conf. on Yeast Genetics and Mole. Biol. 1990.

Koser, et al., "The CYP2 gene of *Saccharomyces cerevisiae* encodes a cyclosporin . . . ," Gene, 108, (1991), pp. 73–80.

Berger, et al., "Molecular Hybridization of Immobilized Nucleic Acids: Theoretical Concepts and Practical Considerations", Methods in Enzymology, vol. 152, pp. 399–407 (1987).

Breuder, et al., "Calcineurin is Essential in Cyclosporin A– and FK506–sensitive yeast strains", PNAS, vol. 91, pp. 5372–5376 (1994).

Forr, et al., "Calcineurin mediates inhibition by FK506 and cyclosporin of recovery from a–factor arrest in yeast", Nature, vol. 360, pp. 682–684 (1992).

*Primary Examiner*—Nancy Degen
*Attorney, Agent, or Firm*—Joseph A. Coppola; Jack L. Tribble

[57] ABSTRACT

DNA molecules encoding proteins involved in biosynthesis of 1,3-beta-D glucan are identified, cloned, expressed and used in in vitro assays to screen for antifungal compounds, including compounds that affect cell wall biosynthesis. The invention includes but is not limited to the purified DNA molecules, assays employing the DNA molecules, proteins encoded by the DNA molecules, cells expressing the DNA molecules and altered forms of the molecules.

9 Claims, 51 Drawing Sheets

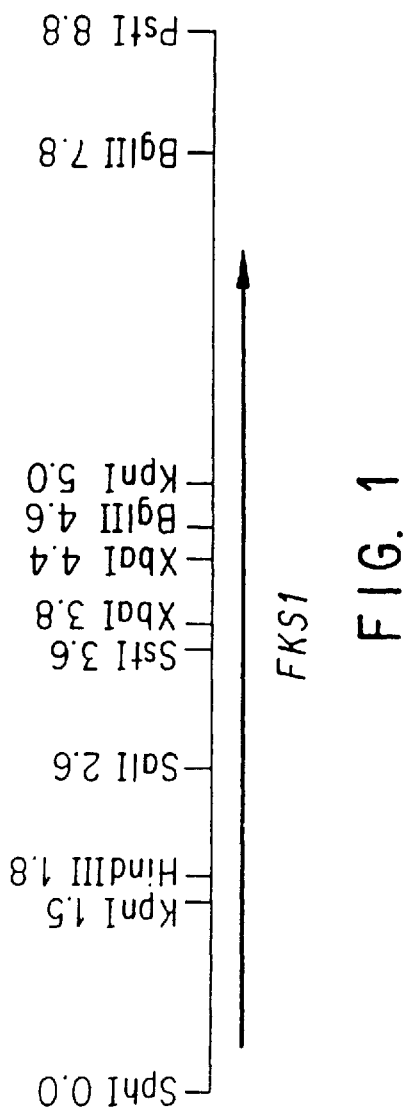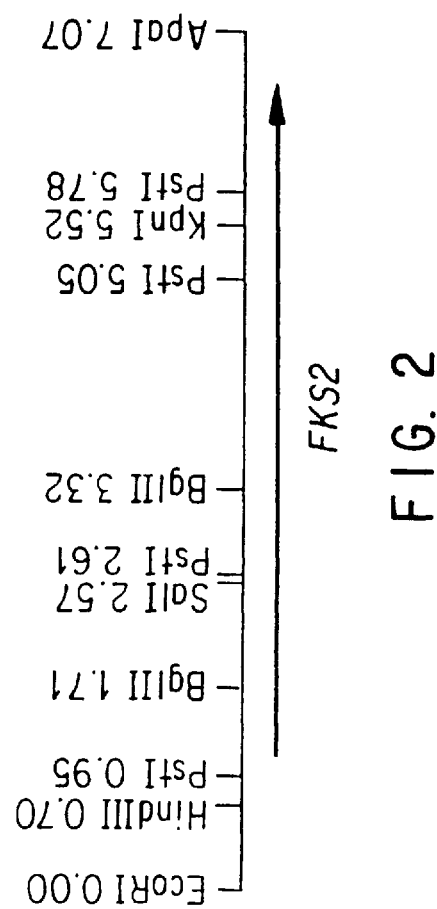

```
  1 TACTGTATCGGTTTCAAGTCTGCTGCTCCCGAGTACACGCTTCGCACCCGTATTTGGTCC  60
  1  Y  C  I  G  F  K  S  A  A  P  E  Y  T  L  R  T  R  I  W  S   20

61 TCGCTGCGTTCGCAAACTCTTTACAGAACTGTATCCGGGATGATGAACTATAGCAGAGCT 120
 21  S  L  R  S  Q  T  L  Y  R  T  V  S  G  M  M  N  Y  S  R  A   40

121 ATCAAGCTCCTCTACCGTGTGGAGAACCCGGAAGTCGTCCAGATGTTCGGTGGTAATTCT 180
 41  I  K  L  L  Y  R  V  E  N  P  E  V  V  Q  M  F  G  G  N  S   60

181 GAGAAGCTGGAACATGAGCTCGAGAGGATGGCCCGTCGCAAGTTCAAGATCTGTGTTTCA 240
 61  E  K  L  E  H  E  L  E  R  M  A  R  R  K  F  K  I  C  V  S   80

241 ATGCAGCGGTATGCCAAATTCACAAAAGAAGAACGTGAGAACACAGAGTTCCTCCTCCGA 300
 81  M  Q  R  Y  A  K  F  T  K  E  E  R  E  N  T  E  F  L  L  R  100

301 GCCTACCCCGACCTGCAGATTGCCTATCTCGATGAGGAACCTCCAGCCAACGAGGGTGAA 360
101  A  Y  P  D  L  Q  I  A  Y  L  D  E  E  P  P  A  N  E  G  E  120

361 GAGCCGCGTCTCTACTCTGCTTTGATTGATGGACACTGTGAGCTGCTCGAGAATGGCATG 420
121  E  P  R  L  Y  S  A  L  I  D  G  H  C  E  L  L  E  N  G  M  140

421 CGGAAGCCCAAGTTCAGGATCCAGCTCTCCGGAAACCCGATCCTTGGTGACGGCAAGTCT 480
141  R  K  P  K  F  R  I  Q  L  S  G  N  P  I  L  G  D  G  K  S  160

481 GACAACCAAAACCACTCGATCATTTTCTACCGCGGTGAATACATTCAGGTCATTGATGCC 540
161  D  N  Q  N  H  S  I  I  F  Y  R  G  E  Y  I  Q  V  I  D  A  180

541 AACCAAGACAACTATCTCGAAGAGTGCTTGAAAATCCGAAGCGTTCTTGCTGAGTTTGAG 600
181  N  Q  D  N  Y  L  E  E  C  L  K  I  R  S  V  L  A  E  F  E  200

601 GAATTGACCACCGACAATGTCTCGCCTTACACTCCTGGCGTTGCCTCTTCCTCTGAAGCT 660
201  E  L  T  T  D  N  V  S  P  Y  T  P  G  V  A  S  S  S  E  A  220

661 CCTGTTGCTATCCTTGGTGCCCGTGAATACATTTTCTCAGAGAACATTGGTGTACTTGGT 720
221  P  V  A  I  L  G  A  R  E  Y  I  F  S  E  N  I  G  V  L  G  240

721 GACGTTGCCGCCGGTAAAGAACAGACATTTGGTACCCTGTTTGCTCGTACTCTTGCTCAG 780
241  D  V  A  A  G  K  E  Q  T  F  G  T  L  F  A  R  T  L  A  Q  260

781 ATTGGCGGAAAGCTCCATTATGGTCACCCTGATTTCCTGAATGGTATCTTCATGACTACC 840
261  I  G  G  K  L  H  Y  G  H  P  D  F  L  N  G  I  F  M  T  T  280
```

FIG.5A

```
841  AGAGGTGGTATCTCCAAGGCTCAAAAAGGTCTACACCTTAACGAGGATATCTACGCTGGT  900
281   R  G  I  S  K  A  Q  K  G  L  H  L  N  E  D  I  Y  A  G   300

901  ATGAACGCCATGGTTCGTGGTGGCCGCATCAAGCACTGCGAGTACTTCCAGTGTGGTAAG  960
301   M  N  A  M  V  R  G  G  R  I  K  H  C  E  Y  F  Q  C  G  K  320

961  GGTCGTGATCTTGGTTTCGGTTCCATTCTTAATTTCACCACTAAGATTGGCACTGGTATG  1020
321   G  R  D  L  G  F  G  S  I  L  N  F  T  T  K  I  G  T  G  M  340

1021 GGTGAGCAAATGCTATCAAGAGAGTACTACTACTKGGGTACTCAACTGCCACTCGACCGA  1080
341   G  E  Q  M  L  S  R  E  Y  Y  Y  X  G  T  Q  L  P  L  D  R  360

1081 TTCCTGTCCTTTTACTATGYTCACCCTGGATTCCACATCAACAACATGTTTATTATGTTG  1140
361   F  L  S  F  Y  Y  X  H  P  G  F  H  I  N  N  M  F  I  M  L  380

1141 TCTGTGCAAATGTTCATGATTGTTCTGATCAACCTGGGGGCCCTGAAGCACGAAACCATC  1200
381   S  V  Q  M  F  M  I  V  L  I  N  L  G  A  L  K  H  E  T  I  400

1201 AACTGCAACTACAACTCCGACCTGCCCATTACCGATCCACTTATGCCAACGTTCTGCGCG  1260
401   N  C  N  Y  N  S  D  L  P  I  T  D  P  L  M  P  T  F  C  A  420

1261 CCTCTCACTCCTATCATCAACTGGGTCAACCGCTGTGTTATTTCGATTTTCATCGTTTTC  1320
421   P  L  T  P  I  I  N  W  V  N  R  C  V  I  S  I  F  I  V  F  440

1321 TTCATTTCGTTTGTTCCTTTGGCTGTTCAAGAATTGACTGAAAGAGGACTCTGGCGTATG  1380
441   F  I  S  F  V  P  L  A  V  Q  E  L  T  E  R  G  L  W  R  M  460

1381 GCAACGCGTCTGGCCAAACATTTCGGATCTTTCTCCTTCATGTTCGAGGTGTTTGTTTGT  1440
461   A  T  R  L  A  K  H  F  G  S  F  S  F  M  F  E  V  F  V  C  480

1441 CAAATCTATTCCAACGCTGTGCACCAAAACTTGTCTTTCGGTGGAGCGCGCTACATCGCT  1500
481   Q  I  Y  S  N  A  V  H  Q  N  L  S  F  G  G  A  R  Y  I  A  500

1501 ACCGGTCGTGGTTTCGCAACTGCTCGTATCCCATTCGGCGTTCTGTACTCTCGGTTTGCC  1560
501   T  G  R  G  F  A  T  A  R  I  P  F  G  V  L  Y  S  R  F  A  520

1561 GGACCTTCAATTTACACCGGTTTCCGTCTGCTGATCATGCTGCTCTTCTCAACCTCAACT  1620
521   G  P  S  I  Y  T  G  F  R  L  L  I  M  L  L  F  S  T  S  T  540
```

FIG.5B

```
1621 ACCTGGACTGCCTCTCTCATTTGGTTCTGGGTCTCTCTTCTCGCCCTTTGCATCTCCCCA 1680
 541  T  W  T  A  S  L  I  W  F  W  V  S  L  L  A  L  C  I  S  P  560

1681 TTCCTTTTCAACCCTCACCAGTTTGCCTGGAACGACTTCTTCATCGATTACCGTGACTAC 1740
 561  F  L  F  N  P  H  Q  F  A  W  N  D  F  F  I  D  Y  R  D  Y  580

1741 ATCCGATGGCTTTCGCGCGGTAACTCTCGCTCACACGCATCCTCATGGATTGGCTTCTGC 1800
 581  I  R  W  L  S  R  G  N  S  R  S  H  A  S  S  W  I  G  F  C  600

1801 CGTTTGTCGCGTACTCGGATCACTGGTTACAAGCGCAAGCTTCTCGGTGTGCCGTCGGAG 1860
 601  R  L  S  R  T  R  I  T  G  Y  K  R  K  L  L  G  V  P  S  E  620

1861 AAAGGATCAGGTGACGTTCCCAGAGCTCGTATTACCAACATTTTCTTCAGCGAAATTGTC 1920
 621  K  G  S  G  D  V  P  R  A  R  I  T  N  I  F  F  S  E  I  V  640

1921 GCTCCTCTAGTCCTCGTTGCTGTTACCCTCGTTCCATACCTCTACATCAATTCTCGGACT 1980
 641  A  P  L  V  L  V  A  V  T  L  V  P  Y  L  Y  I  N  S  R  T  660

1981 GGTGTGAGCGCTGATGTGGACGGGGGCAATGACCCTCACGATGCCATTTTGCGTATTGCC 2040
 661  G  V  S  A  D  V  D  G  G  N  D  P  H  D  A  I  L  R  I  A  680

2041 ATTGTAGCATTTGGACCTATTGGTATCAATGCCGGTGTTGCTGCTGTTTTCTTTGGTATG 2100
 681  I  V  A  F  G  P  I  G  I  N  A  G  V  A  A  V  F  F  G  M  700

2101 GCATGCTGCATGGGTCCCATCCTGAGCATGTGCTGCAAGAAGTTCGGTGCTGTGTTGGCG 2160
 701  A  C  C  M  G  P  I  L  S  M  C  C  K  K  F  G  A  V  L  A  720

2161 GCTATTGCCCACGCGATTGCTGTGATCATCTTGCTTGTCATCTTTGAAGTCATGTTCTTC 2220
 721  A  I  A  H  A  I  A  V  I  I  L  L  V  I  F  E  V  M  F  F  740

2221 CTCGAACACTGGTCTTGGCCCCGGTGCGTCATGGGCATGATCGCCATGGGTGCCATTCAA 2280
 741  L  E  H  W  S  W  P  R  C  V  M  G  M  I  A  M  G  A  I  Q  760

2281 CGTTTCGTCTACAAACTTATTATCGCGCTCGCTCTTACCCGAGAGTTCAAGCATGACCAG 2340
 761  R  F  V  Y  K  L  I  I  A  L  A  L  T  R  E  F  K  H  D  Q  780

2341 TCGAACATCGCATGGTGGACTGGAAAATGGTACAACATGGGTTGGGACTCTCTCTCTCAA 2400
 781  S  N  I  A  W  W  T  G  K  W  Y  N  M  G  W  D  S  L  S  Q  800
```

FIG.5C

2401 CCGGGCCCGAGAGTTCCTCTGCAAGATCACGGAGTTGGGCTATTTCTCAGCAGACTTCGTC 2460
801  P  G  R  E  F  L  C  K  I  T  E  L  G  Y  F  S  A  D  F  V   820

2461 ATTGGTCATCTCCTATTGTTCATTATGCTGCCCGCTCTTTGTGTTCCTTACATTGACAAG 2520
821  I  G  H  L  L  F  I  M  L  P  A  L  C  V  P  Y  I  D  K      840

2521 TTTCACTCAGYCATTCTCTTTTGGGTCCSGCCCAAGGTAAGAACC 2565
841  F  H  S  X  I  L  F  W  V  X  P  K  V  R  T      855

FIG.5D

```
  1  GCATGCAAAC ATCTACACAA TTAGCAAGGG CAATCCATAT TTTGTCTTTT
 51  CGCGCCCTGG AAAGGCCTAA GTAATGTCGT AAACGCATTC TATCTGTACT
101  TCAACTCTCC TCTGTGCATT GGTTTGTGCA AATCACATTT TACGATACTG
151  CCAGATTTAT GCAAAAAGAG AAAACCAAGG GACCAGAACA AAGCAAAATT
201  ACGATAAACT TCGAATTCCT TCGTGCTTGA CTAAGACAAA GGGATGGACG
251  TAGCGATTTT TAGCGGGCCA AGAACTGGTT CCGAAAAAGC ACAGGTACAC
301  CGAACCCTCA GCTAAGGAGG GACAGCACCG ATGCGGAAGG ACAAACTTTC
351  TTTTTGCCTA TCACAGTATC TTATCGAGCT AACTATTTTC GACACACATG
401  AAAAAGCAGA AATATTAACG AAAAAGAAAA GAAAGACCAT GTCATGTACG
451  GGCAATCAGA ATCTGTAACA AGCGCCATTT TTTTTTCTGT ATCGGGCCCT
501  CCTTACTGCT CTCCTTCCGT GTAACGCGTT ATGAAACTCT AATCCTACTA
551  TCGGCGACTC TCTCGAAATT TTTCTTAACG CGTCCTTGTA CTGCGTCTAA
601  CGCTTTTGCC ACTTGGATTT CTATTATAGG AAATAGTCTC ACTTACTGGG

F I G. 6A
```

| | | | | |
|---|---|---|---|---|
| 651 | CGACGAATTT | TCGCGTTTTG | ATGAAGCACA | GGAAGAATTT | CTTTTTTTTT |
| 701 | TGGCTTCTTC | TGGTTCCGTT | TTTTACGCGC | ACAAATCTAA | AAAAAGAAAT |
| 751 | AATTATAACC | TAGTCTCGAA | AATTTTCATC | GATCCATTCG | TTCCTTTTTT |
| 801 | TCGATTTTTT | CAGATCAAAA | TTCTTGTTTC | TTTCTTTGTC | TTAGTTTATA |
| 851 | TTAAAAGATA | TTTTGATTTT | ACTCCTGAAC | TATTTATTCT | TTCTAAGAAG |
| 901 | GCCAGAACAC | TACAGCTGTT | TTAACCGACT | ACGAAGTTCT | CCATTCTCGA |
| 951 | ACACTAGCCT | TCATTACCA | AACAGGAACT | AGCGTATATC | ATTAGTCCTT |
| 1001 | ATTCGAAAAG | AGATTGGTAG | ATATTTATTG | TAGTTTGTGA | GAAGGAGAAA |
| 1051 | ATACTGTCAT | TGGACTGATA | GTTAGAGGAC | ATTAACCTCT | CTTACGTTCG |
| 1101 | CTCAAAAAAA | TTAAAATAAG | CAAGTAGCTG | AAATCAAGTC | TTTCATACAA |
| 1151 | CGGTCAGACC | ATGAACACTG | ATCAACAACC | TTATCAGGGC | CAAACGGACT |
| 1201 | ATACCCAGGG | ACCAGGTAAC | GGGCAAAGTC | AGGAACAAGA | CTATGACCAA |
| 1251 | TATGGCCAGC | CTTTGTATCC | TTCACAAGCT | GATGGTTACT | ACGATCCAAA |

FIG. 6B

```
1301  TGTCGCTGCT GGTACTGAAG CTGATATGTA TGGTCAACAA CCACCAAACG
1351  AGTCTTACGA CCAAGACTAC ACAAACGGTG AATACTATGG TCAACCGCCA
1401  AATATGGCTG CTCAAGACGG TGAAAACTTC TCGGATTTTA GCAGTTACGG
1451  CCCTCCTGGA ACACCTGGAT ATGATAGCTA TGGTGGTCAG TATACCGCTT
1501  CTCAAATGAG TTATGGAGAA CCAAATTCGT CGGGTACCTC GACTCCAATT
1551  TACGGTAATT ATGACCCAAA TGCTATCGCT ATGGCTTTGC CAAATGAACC
1601  TTATCCCGCT TGGACTGCTG ACTCTCAATC TCCCGTTTCG ATCGAGCAAA
1651  TCGAAGATAT CTTTATTGAT TTGACCAACA GACTCGGGTT CCAAAGAGAC
1701  TCCATGAGAA ATATGTTTGA TCATTTTATG GTTCTCTTGG ACTCTAGGTC
1751  CTCGAGAATG TCTCCTGATC AAGCTTTACT ATCTTTACAT GCCGACTACA
1801  TTGGTGGCGA TACTGCTAAC TATAAAAAAT GGTATTTTGC TGCTCAGTTA
1851  GATATGGATG ATGAAATTGG TTTTAGAAAT ATGAGTCTTG GAAAACTCTC
1901  AAGGAAGGCA AGAAAAGCTA AGAAGAAAAA CAAGAAAGCA ATGGAAGAGG
```

FIG. 6C

```
1951  CCAATCCCGA AGACACTGAA GAAACTTTAA ACAAAATTGA AGGCGACAAC
2001  TCCCTAGAGG CTGCTGATTT TAGATGGAAG GCCAAGATGA ACCAGTTGTC
2051  TCCCCTGGAA AGAGTTCGTC ATATCGCCTT ATATCTGTTA TGTTGGGGTG
2101  AAGCTAATCA AGTCAGATTC ACTGCTGAAT GTTTATGTTT TATCTACAAG
2151  TGTGCTCTTG ACTACTTGGA TTCCCCTCTT TGCCAACAAC GCCAAGAACC
2201  TATGCCAGAA GGTGATTTCT TGAATAGAGT CATTACGCCA ATTATCATT
2251  TCATCAGAAA TCAAGTTTAT GAAATTGTTG ATGGTCGTTT TGTCAAGCGT
2301  GAAAGAGATC ATAACAAAAT TGTCGGTTAT GATGATTTAA ACCAATTGTT
2351  CTGGTATCCA GAAGGTATTG CAAAGATTGT TCTTGAAGAT GGAACAAAAT
2401  TGATAGAACT CCCATTGGAA GAACGTTATT TAAGATTAGG CGATGTCGTC
2451  TGGGATGATG TATTCTTCAA AACATATAAA GAGACCCGTA CTTGGTTACA
2501  TTTGGTCACC AACTTCAACC GTATTTGGGT TATGCATATC TCCATTTTTT
2551  GGATGTACTT TGCATATAAT TCACCAACAT TTTACACTCA TAACTATCAA
```

FIG. 6D

```
2601  CAATTGGTCG ACAACCAACC TTTGGCTGCT TACAAGTGGG CATCTTGCGC
2651  ATTAGGTGGT ACTGTCGCAA GTTTGATTCA AATTGTCGCT ACTTTGTGTG
2701  AATGGTCATT CGTTCCAAGA AAATGGGCTG GTGCTCAACA TCTATCTCGT
2751  AGATTCTGGT TTTTATGCAT CATCTTTGGT ATTAATTTGG GTCCTATTAT
2801  TTTTGTTTTT GCTTACGACA AAGATACAGT CTACTCCACT GCTGCACACG
2851  TTGTTGCTGC TGTTATGTTC TTTGTTGCGG GTTGTTTACG TCATATATGA AAAAATCTAC
2901  TCCATTATGC CATTGGGGGG GTTGCATCTC AAACATTCAC TGCTGCATTT GCCCCTCTAC
2951  AAGGCGTTAT GTTGCATCTC AAACATTCAC TGCTGCATTT GCCCCTCTAC
3001  ATGGGTTAGA TAGATGGATG TCCTATTTAG GTTTTATCTT TGAGAGATCC
3051  GCCAAATATT CAGAATCGTA CTACTTTTTA CTGCAATGAG GAATACTGGT
3101  AATTAGAATT TTGTCCACCA CTGCAATGAG GTGTACAGGT GAATACTGGT
3151  GGGGTGCCGGT ACTTTGTAAA GTGCAACCCA AGATTGTCTT AGTTTGGTT
3201  ATCGCTACCG ACTTCATTCT TTTCTTCTTG GATACCTACT TATGGTACAT
```

FIG. 6E

```
3251  TATTGTGAAT ACCATTTCT CTGTTGGAA ATCTTTCTAT TTAGGTATTT
3301  CTATCTTAAC ACCATGGAGA AATATCTTCA CAAGATTGCC AAAAAGAATA
3351  TACTCCAAGA TTTGGCTAC TACTGATATG GAAATTAAAT ACAAACCAAA
3401  GGTTTTGATT TCTCAAGTAT GGAATGCCAT CATTATTTCA ATGTACAGAG
3451  AACATCTCTT AGCCATCGAC CATGTACAAA AATTACTATA TCATCAAGTT
3501  CCATCTGAAA TCGAAGGTAA AAGAACTTTG AGAGCTCCTA CCTTCTTTGT
3551  TTCTCAAGAT GACAATAATT TTGAGACTGA ATTTTTCCCT AGGGATTCAG
3601  AGGCTGAGCG TCGTATTTCT TTCTTTGCTC AATCTTTGTC TACTCCAATT
3651  CCCGAACCAC TTCCAGTTGA TAACATGCCA ACGTTCACAG TATTGACTCC
3701  TCACTACGCG GAAAGAATTC TGCTGTCATT AAGAGAAATT ATTCGTGAAG
3751  ATGACCAATT TTCTAGAGTT ACTCTTTTAG AATATCTAAA ACAATTACAT
3801  CCCGTTGAAT GGGAATGTTT TGTTAAGGAT ACTAAGATTT TGGCTGAAGA
3851  AACCGCTGCC TATGAAGGAA ATGAAAATGA AGCTGAAAAG GAAGATGCTT
```

FIG. 6F

```
3901  TGAAATCTCA AATCGATGAT TTGCCATTTT ATTGTATTGG TTTTAAATCT
3951  GCTGCTCCAG AATATACACT TCGTACGAGA ATTTGGGCTT CTTTGAGGTC
4001  GCAGACTCTA TATCGTACCA TTTCAGGGTT CATGAATTAT TCAAGAGCTA
4051  TCAAATTACT GTATCGTGTG GAAAATCCTG AAATTGTTCA AATGTTTGGT
4101  GGTAATGCTG AAGGCTTAGA AAGAGAGCTA GAAAAGATGG CAAGAAGAAA
4151  GTTTAAATTT TTGGTCTCTA TGCAGAGATT GGCTAAATTC AAACCACATG
4201  AACTGGAAAA TGCTGAGTTT TTGTTGAGAG CTTACCCAGA CTTACAAATT
4251  GCCTACTTGG ATGAAGAGCC ACCTTTGACT GAAGGTGAGG AGCCAAGAAT
4301  CTATTCCGCT TTGATTGATG GACATTGTGA AATTCTAGAT AATGGTCGTA
4351  GACGTCCCAA GTTTAGAGTT CAATTATCTG GTAACCCAAT TCTTGGTGAC
4401  GGTAAATCTG ATAACCAAAA CCATGCTTTG ATTTTTTACA GAGGTGAATA
4451  CATTCAATTA ATTGATGCCA ACCAAGATAA CTACTTGGAA GAATGTCTGA
4501  AGATTAGATC TGTATTGGCT GAATTGAGG AATTGAACGT TGAACAAGTT
```

FIG. 6G

```
4551  AATCCATATG CTCCCGGTTT AAGGTATGAG GAGCAAACAA CTAATCATCC
4601  TGTTGCTATT GTTGGTGCCA GAGAATACAT TTTCTCTGAA AACTCTGGTG
4651  TGCTGGGGTA TGTGGCCCGCT GGTAAAGAAC AAACTTTTGG TACATTATTT
4701  GCGCGTACTT TATCTCAAAT TGGTGGTAAA TTGCATTATG GTCATCCGGA
4751  TTTCATTAAT GCTACGTTTA TGACCACTAG AGGTGGTGTT TCCAAAGCAC
4801  AAAAGGGTTT GCATTAAAC GAAGATATTT ATGCTGGTAT GAATGCTATG
4851  CTTCGTGGTG GTCGTATCAA GCATTGTGAG TATTATCAAT GTGGTAAAGG
4901  TAGAGATTTG GGTTTCGGTA CAATTCTAAA TTTCACTACT AAGATTGGTG
4951  CTGGTATGGG TGAACAAATG TTATCTCGTG AATATTATTA TCTGGGTACC
5001  CAATTACCAG TGGACCGTTT CCTAACATTC TATTATGCCC ATCCTGGTTT
5051  CCATTTGAAC AACTTGTTCA TTCAATTATC TTTGCAAATG TTTATGTTGA
5101  CTTTGGTGAA TTTATCTTCC TTGGCCCATG AATCTATTAT GTGTATTTAC
5151  GATAGGAACA AACCAAAAAC AGATGTTTTG GTTCCAATTG GGTGTTACAA
```

FIG. 6H

```
5201  CTTCCAACCT GCGGTTGATT GGGTGAGACG TTATACATTG TCTATTTCA
5251  TTGTTTTCTG GATTGCCTTC GTTCCTATTG TTGTTCAAGA ACTAATTGAA
5301  CGTGGTCTAT GGAAAGCCAC CCAAAGATTT TTCTGCCACC TATTATCATT
5351  ATCCCCTATG TTCGAAGTGT TTGCGGGCCA AATCTACTCT TCTGCGTTAT
5401  TAAGTGATTT AGCAATTGGT GGTGCTCGTT ATATATCCAC CGGTCGTGGT
5451  TTTGCAACTT CTCGTATACC ATTTTCAATT TTGTATTCAA GATTTGCAGG
5501  ATCTGCTATC TACATGGGTG CAAGATCAAT GTTAATGTTG CTGTTCGGTA
5551  CTGTCGCACA TTGGCAAGCT CCACTACTGT GGTTTTGGGC CTCTCTATCT
5601  TCATTAATTT TTGCGCCTTT CGTTTTCAAT CCACATCAGT TTGCTTGGA
5651  AGATTTCTTT TTGGATTACA GGGATTATAT CAGATGGTTA TCAAGAGGTA
5701  ATAATCAATA TCATAGAAAC TCGTGGATTG GTTACGTGAG GATGTCTAGG
5751  GCACGTATTA CTGGGTTTAA ACGTAAACTG GTTGGGCGATG AATCTGAGAA
5801  AGCTGCTGGT GACGCAAGCA GGGCTCATAG AACCAATTTG ATCATGGCTG
```

FIG. 6I

```
5851  AAATCATACC CTGTGCAATT TATGCAGCTG GTTGTTTTAT TGCCTTCACG
5901  TTTATTAATG CTCAAACCGG TGTCAAGACT ACTGATGATG ATAGGGTGAA
5951  TTCTGTTTTA CGTATCATCA TTTGTACCTT GGCGCCAATC GCCGTTAACC
6001  TCGGTGTTCT ATCCTTCTGT ATGGGTATGT CATGCTGCTC TGGTCCCTTA
6051  TTTGGTATGT GTTGTAAGAA GACAGGTTCT GTAATGGCTG GAATTGCCCA
6101  CGGTGTTGCT GTTATTGTCC ACATTGCCTT TTTCATTGTC ATGTGGGTTT
6151  TGGAGAGCTT CAACTTTGTT AGAATGTTAA TCGGAGTCGT TACTTGTATC
6201  CAATGTCAAA GACTCATTTT TCATTGCATG ACAGCGTTAA TGTTGACTCG
6251  TGAATTTAAAA AACGATCATG CCAATACAGC CTTCTGGACT GGTAAGTGGT
6301  ATGGTAAAGG TATGGGTTAC ATGGCTTGGA CCCAGCCAAG TAGAGAATTA
6351  ACCGCCAAGG TAATTGAGCT TTCAGAATTT GCAGCTGATT TTGTTCTAGG
6401  TCATGTGATT TTAATCTGTC AACTGCCACT CATTATAATC CCAAAAATAG
6451  ATAAATTCCA CTCGATTATG CTATTCTGGC TAAAGCCCTC TCGTCAAATT
```

FIG. 6J

```
6501  CGTCCCCCAA TTTACTCTCT GAAGCAAACT CGTTTGCGTA AGCGTATGGT
6551  CAAGAAGTAC TGCTCTTTGT ACTTTTTAGT ATTGGCTATT TTTGCAGGAT
6601  GCATTATTGG TCCTGCTGTA GCCCTCTGCTA AGATCCACAA ACACATTGGA
6651  GATTCATTGG ATGGCGTTGT TCACAATCTA TTCCAACCAA TAAATACAAC
6701  CAATAATGAC ACTGGTTCCC AAATGTCAAC TTATCAAAGT CACTACTATA
6751  CTCATACGCC ATCATTAAAG ACCTGGTCAA CTATAAAATA ATACAATCAA
6801  TACTTGCTTG AACGCTTGAT TTTACTGATA TTCTATCCAA AAGCAAGTAG
6851  ACCAGAAACT CTCAAGATGT TGCAAATACC GTTCGATGTT TTTGGTTTAG
6901  ATTGTTTTAA TGTTGATGCT TTTTTACTTA TTTTTGGAAG CGTCTTTTTA
6951  ATTTAGTTTT ATATTATAGG TATATGAATG TGTTTATGCC AATAAGGGTT
7001  TTTTTGTACA GTTATGTGAT TATAAACAGT CTTTTGTCTA GTTTTTTTCA
7051  CCAGTATCGG CCCTCTATTA TAAAAAACGG AGCAGCTTTC GGTGTCAGTA
7101  ATTCTGAAAA AATTGTGTC ACTCTGATTG TAAATGAATT AATTTAGCTA
```

FIG. 6K

```
7151  GATAGTTGCG  AGCCCCAACG  AGAAGATTGT  CAGACAAAGA  CAACATTCAA
7201  CAACCTACAT  CCGTTACTAT  TCGTTAACTC  GAGGTACTTG  AAACTTTCA
7251  GTTAAGTATG  AACAAGAAAC  AAAATTTTTA  CGCAGCCATT  ATTGTGGCTA
7301  TTTTCTTTG   TTGCAATTG   TCTCATGGCT  CTTCAGTGT   CAGCTTTGAA
7351  AAAACCCCTG  CTATTAAAAT  TGTAGGAAAC  AAATTCTTTG  ACTCTGAGAG
7401  TGGGAACAG   TTCTTCATCA  AGGGCATTGC  TTACCAATTG  CAGAGAAGTG
7451  AAGAGGAGCT  TAGCAATGCA  AATGGGGCTT  TTGAGACAAG  TTATATTGAT
7501  GCCTTAGCGG  ACCCAAAAAT  ATGCTTAAGA  GATATTCCAT  TTTGAAAAT
7551  GCTAGGAGTG  AACACACTGC  GTGTTTATGC  AATAGATCCG  ACAAAATCAC
7601  ATGATATATG  TATGGAAGCT  CTATCTGCCG  AAGGAATGTA  CGTCCTATTA
7651  GATCT
```

FIG. 6L

```
  1 MNTDQQPYQG QTDYTQGPGN GQSQEQDYDQ YGQPLYPSQA DGYDPNVAA
 51 GTEADMYGQQ PPNESYDQDY TNGEYYGQPP NMAAQDGENF SDFSSYGPPG
101 TPGYDSYGGQ YTASQMSYGE PNSSGTSTPI YGNYDPNAIA MALPNEPYPA
151 WTADSQSPVS IEQIEDIFID LTNRLGFQRD SMRNMFDHFM VLLDSRSSRM
201 SPDQALLSLH ADYIGGDTAN YKKWYFAAQL DMDDEIGFRN MSLGKLSRKA
251 RKAKKKNKKA MEEANPEDTE ETLNKIEGDN SLEAADFRWK AKMNQLSPLE
301 RVRHIALYLL CWGEANQVRF TAECLCFIYK CALDYLDSPL CQQRQEMPE
351 GDFLNRVITP IYHFIRNQVY EIVDGRFVKR ERDHNKIVGY DDLNQLFWYP
401 EGIAKIVLED GTKLIELPLE ERYLRLGDVV WDDVFFKTYK ETRTWLHLVT
451 NFNRIWVMHI SIFWMYFAYN SPTFYTHNYQ QLVDNQPLAA YKWASCALGG
501 TVASLIQIVA TLCEWSFVPR KWAGAQHLSR RFWFLCIIFG INLGPIIFVF
551 AYDKDTVYST AAHVAAVMF FVAVATIFF SIMPLGGLFT SYMKKSTRRY
601 VASQTFTAAF APLHGLDRWM SYLVWVTVFA AKYSESYYFL VLSLRDPIRI
```

FIG. 7A

```
 651  LSTTAMRCTG EYWGAVLCK VQPKIVLGLV IATDFILFFL DTYLWYIIVN
 701  TIFSVGKSFY LGISILTPWR NIFTRLPKRI YSKILATTDM EIKYKPKVLI
 751  SQVWNAIIIS MYREHLLAID HVQKLLYHQV PSEIEGKRTL RAPTFFVSQD
 801  DNNFETEFFP RDSEAERRIS FFAQSLSTPI PEPLPVDNMP TFTVLTPHYA
 851  ERILLSLREI IREDDQFSRV TLLEYLKQLH PVEWECFVKD TKILAEETAA
 901  YEGNENEAEK EDALKSQIDD LPFYCIGFKS AAPEYTLRTR IWASLRSQTL
 951  YRTISGFMNY SRAIKLLYRV ENPEIVQMFG GNAEGLEREL EKMARRKFKF
1001  LVSMQRLAKF KPHELENAEF LLRAYPDLQI AYLDEEPPLT EGEEPRIYSA
1051  LIDGHCEILD NGRRRPKFRV QLSGNPILGD GKSDNQNHAL IFYRGEYIQL
1101  IDANQDNYLE ECLKIRSVLA EFEELNVEQV NPYAPGLRYE EQTTNHPVAI
1151  VGAREYIFSE NSGVLGDVAA GKEQTFGTLF ARTLSQIGGK LHYGHPDFIN
1201  ATFMTRGGV SKAQKGLHLN EDIYAGMNAM LRGGRIKHCE YYQCGKGRDL
1251  GFGTILNFTT KIGAGMGEQM LSREYYYLGT QLPVDRFLTF YYAHPGFHLN
```

FIG. 7B

```
1301  NLFIQLSLQM  FMLTLVNLSS  LAHESIMCIY  DRNKPKTDVL  VPIGCYNFQP
1351  AVDWVRRYTL  SIFIVFWIAF  VPIVVQELIE  RGLWKATQRF  FCHLLSLSPM
1401  FEVFAGQIYS  SALLSDLAIG  GARYISTGRG  FATSRIPFSI  LYSRFAGSAI
1451  YMGARSMLML  LFGTVAHWQA  PLLWFWASLS  SLIFAPFVFN  PHQFAWEDFF
1501  LDYRDYIRWL  SRGNNQYHRN  SWIGYVRMSR  ARITGFKRKL  VGDESEKAAG
1551  DASRAHRTNL  IMAEIIPCAI  YAAGCFIAFT  FINAQTGVKT  TDDDRVNSVL
1601  RIIICTLAPI  AVNLGVLFFC  MGMSCCCSGPL  FGMCCKKTGS  VMAGIAHGVA
1651  VIVHIAFFIV  MWVLESFNFV  RMLIGVVTCI  QCQRLIFHCM  TALMLTREFK
1701  NDHANTAFWT  GKWYGKGMGY  MAWTQPSREL  TAKVIELSEF  AADFVLGHVI
1751  LICQLPLIII  PKIDKFHSIM  LFWLKPSRQI  RPPIYSLKQT  RLRKRMVKKY
1801  CSLYFLVLAI  FAGCIIGPAV  ASAKIHKHIG  DSLDGVVHNL  FQPINTTNND
1851  TGSQMSTYQS  HYYTHTPSLK  TWSTIK
```

FIG. 7C

```
  1  GAATTCCCCT CGCAACACTG AAAGATGCCA TTGTCAAAGG TGAAATTGCC
 51  GCGTGGCCCC TAGATCCTGC TCGTGAACGA TGGACGCGGC CTGCGCTATT
101  CATCAGGGCT ACTCAATCGC ATTATGTGGT AGACGAGTAT CTTCCGATCA
151  TCGGCGCGTT CTTTCCACGC TTTGAAACAC GTGACATCGA TGCGGGTCAC
201  TGGGTAAATG CGGAGAAGCC TGGGGAATGT GCCGAAAGCA TCGTCGATTT
251  TGTGGAGCGG CACGAGGATT AAAGGCAAGC GCCCCGGAGC AAGGTGCCAG
301  TAGCACCAGT CGGTGGCTGT GCGCTTGCCG TAGCACATGA CATACGGACT
351  ATTGTGTGAG TGGTGATGGG GTGTAGGCAG TGCCACACCA GTTTAAAGGC
401  CTAGTAACGG CAAATCGCCA AAAGAGATGA TGCTGATGCA TACGATAAGA
451  TCGTCAGTTT CACGTTCGCG GTTCGAACAT GGAATTGTGG CTAAAGAAAT
501  TTGGGCGGTA TGATGCAAAT GAGGTGTACG TATGTATATA TAGCAAAGAG
551  TAGAATAAAA TGAGATAAAG CCTCGTTCGT TCTCTCCATT TCTTCCCTGT
601  TTCTCCTTTA TTTTCTCTAC TGCTTATTTC GAGTTCACCA GAGAACAAGA
```

FIG. 8A

```
 651  GAGCAGGAAC GCAAAGAGTG TGTGACACGA AATTCAAGAT ACAAAAATAA
 701  AAGCTTACGT TGTGTATTTC AACTGGTGTG CTAAGAATAG AGTTTCATAA
 751  AGTACTGCAT TTATTCATAT ATTATTTTTG TTATTTGTAT ATATACTTCA
 801  CACTTAGAGT TCTACTAAAA GTCTACCCAG CACGCATCCT TCGTTTATTT
 851  TTACATCTCT CTTTTGCTTT TCCTTTTTTT TTTTGGTGCT TGCTAGATAC
 901  TACTGAAGAT CAAAGGTTAC AAAGAACGCC GCATATATTT TCTGCAGGCA
 951  TATTAAAGAA GTTACAAAAG GATTAATCGA AGCGCTGTTT GGATACACTC
1001  CTGTAAAGAG AAGAAAAGGA AAAAAATAAA AAGTGGACAA TAAATAATTA
1051  TTAAACTGTC ATAGTTATGT CCTACAACGA TCCAAACTTG AATGGACAGT
1101  ATTACAGTAA CGGTGATGGG ACTGGTGACG GTAATTACCC TACGTACCAA
1151  GTGACACAGG ATCAAAGTGC GTACGATGAG TACGGTCAGC CAATCTATAC
1201  ACAAAACCAA CTGGATGATG GTTATTATGA TCCAAACGAA CAATACGTTG
1251  ACGGTACACA ATTCCCTCAG GGACAAGATC CTTCACAAGA CCAAGGTCCT
```

FIG. 8B

```
1301  TATAATAACG ATGCTAGTTA CTATAACCAA CCCCCCAATA TGATGAACCC
1351  GTCTTCTCAA GATGGAGAGA ACTTCTCAGA TTTTAGCAGC TATGGTCCCC
1401  CATCCGGCAC TTATCCTAAC GATCAATATA CTCCTTCTCA AATGAGTTAT
1451  CCTGATCAAG ATGGTTCTTC AGGGGCCTCA ACCCCCTATG GAAATGGTGT
1501  CGTTAATGGT AATGGCCAGT ACTACGACCC TAATGCTATT GAAATGGCTT
1551  TACCAAATGA TCCATATCCC GCATGGACCG CAGATCCCCA GTCTCCCCTG
1601  CCCATCGAAC AAATCGAAGA TATCTTCATA GATTAACAA ATAAATTCGG
1651  TTTTCAGAGA GATTCCATGA GAAATATGTT TGACCATTTT ATGACCCTTT
1701  TGGACTCTAG ATCTTCTAGG ATGTCTCCAG AACAGGCCCT TTTATCATTA
1751  CATGCAGACT ACATAGGTGG AGATACGGCC AACTACAAAA AATGGTACTT
1801  TGCCGCTCAA CTTGATATGG ATGATGAAAT TGGTTTCAGG AATATGAAGT
1851  TGGGTAAGCT ATCAAGAAAG GCAAGAAAGG CTAAGAAGAA AAATAAAAAA
1901  GCCATGCAAG AGGCTAGTCC TGAAGACACT GAGGAGACTT TAAATCAAAT
```

FIG. 8C

```
1951  TGAGGGTGAT AACTCATTAG AAGCTGCGGA TTTTAGATGG AAGTCAAAGA
2001  TGAATCAACT TTCTCCATTT GAAATGGTTC GTCAAATTGC CTTGTTTTTA
2051  TTATGTTGGG GCGAGGCAAA TCAAGTCAGA TTTACCCCGG AGTGTCTTTG
2101  TTTCATTTAT AAATGCGCCT CTGATTACTT AGATTCTGCA CAATGTCAAC
2151  AACGTCCTGA TCCCTTGCCT GAAGGTGATT TTTGAATAG AGTTATTACT
2201  CCTCTTTATC GTTTTATTAG GAGCCAGGTT TACGAAATCG TGGATGGTCG
2251  ATACGTGAAG AGTGAAAAAG ATCATAACAA AGTTATTGGG TATGATGATG
2301  TCAATCAATT ATTCTGGTAT CCAGAAGGTA TAGCAAAAAT TGTCATGGAA
2351  GATGGAACCA GGTTGATTGA TTTGCCAGCA ATGTCTTCTT GAGGAGCGTT ATTTGAAATT
2401  GGGAGAAATT CCCTGGGATG ATGTCTTCTT TAAAACTTAC AAAGAAACAC
2451  GTTCCTGGTT ACATTAGTT ACCAACTTCA ATCGTATTTG GATCATGCAC
2501  ATCTCAGTAT ATTGGATGTA TTGTGCTTAC AATGCTCCAA CTTTTATAC
2551  TCACAACTAT CAACAATTGG TCGACAATCA GCCTTTGGCA GCTTATAAAT

F I G. 8D
```

```
2601  GGGCCACTGC AGCATTAGGT GGTACTGTGG CAAGTTTGAT TCAAGTTGCC
2651  GCTACTTTGT GCGAGTGGTC ATTCGTTCCT AGAAAATGGG CGGGTGCTCA
2701  ACATTTGTCC CGTAGATTCT GGTTCTTGTG TGTCATTATG GGTATTAATT
2751  TGGGGCCTGT GATATTTGTT TTCGCTTATG ATAAGGACAC AGTATATTCT
2801  ACTGCCGCTC ATGTCGTTGG AGCAGTTATG TTTTTGTTG CTGTGGCAAC
2851  ACTTGTTTTC TTTTCCGTAA TGCCATTGGG TGGATTATTT ACATCGTATA
2901  TGAAAAAGTC CACAAGAAGT TATGTTGCCT CACAGACCTT CACCGCATCT
2951  TTTGCTCCAT TGCATGGTTT AGACAGGTGG ATGTCTTATT TGGTTTGGGT
3001  AACCGTTTTT GCTGCTAAAT ATGCAGAGTC ATATTTTTTT CTAATACTGT
3051  CACTAAGAGA TCCAATTAGG ATTTTATCTA CTACATCAAT GAGATGTACT
3101  GGTGAATACT GGTGGGGTAA TAAGATTTGT AAGGTCCAGC CAAAGATTGT
3151  TTTAGGTTTA ATGATTGCGA CTGACTTCAT TTTGTTCTTT TTGGATACCT
3201  ACTTGTGGTA TATCGTTGTT AACACTGTTT TCTCGGTCGG AAAATCGTTC
```

FIG. 8E

```
3251  TATTTGGGTA TTTCTATCTT AACTCCATGG AGAAATATTT TCACTAGATT
3301  GCCAAAAAGA ATTTATTCTA AGATCTTGGC TACTACTGAT ATGGAAATAA
3351  AATATAAACC GAAAGTACTA ATTTCTCAGA TTTGGAATGC TATCATTATC
3401  TCCATGTACA GAGAACATTT ATTAGCCATA GACCATGTAC AAAAATTGTT
3451  ATATCATCAG GTTCCGTCCG AAATTGAAGG TAAGAGGACT TTGAGAGCAC
3501  CAACTTTCTT TGTTCCCAA  GATGACAATA ATTTGAGAC  TGAATTTTTC
3551  CCTAGAGATT CAGAAGCTGA GCGCCGTATT TCATTTTTG  CCCAATCTCT
3601  ATCCACTCCA ATTCCAGAAC CACTACCAGT TGACAACATG CCAACATTTA
3651  CTGTATTAAC TCCCCATTAC GCCGAGAGGA TTCTATTATC ATTGAGAGAA
3701  ATTATTCGTG AAGATGATCA ATTTTCAAGA GTTACTCTTT TGGAATACCT
3751  GAAGCAATTA CACCCGGTAG AATGGGACTG TTTTGTTAAG GATACGAAAA
3801  TTCTTGCTGA AGAAACGGCC GCATATGAAA ACAATGAAGA TGAACCTGAA
3851  AAGGAAGACG CTCTGAAATC TCAAATTGAT GATTTACCTT TCTATTGTAT
```

FIG. 8F

```
3901  TGGTTTCAAA  TCTGCTGCAC  CAGAATACAC  CTTACGTACG  AGAATCTGGG
3951  CCTCTTTAAG  GTCGCAAACT  TTGTATCGCA  CAATCTCGGG  GTTTATGAAT
4001  TATTCGAGGG  CCATAAAATT  ACTTTATCGT  GTGGAAAATC  CAGAAATCGT
4051  TCAAATGTTC  GGTGGTAATG  CTGATGGATT  AGAAAGAGAA  CTGGAAAAAA
4101  TGGCAAGGCG  AAAATTCAAA  TTCTTGGTTT  CGATGCAAAG  ATTGGCCAAG
4151  TTTAAACCAC  ATGAACTAGA  AAATGCTGAG  TTCCTGTTGA  GAGCTTATCC
4201  GGACTTGCAA  ATTGCCTACC  TGGATGAAGA  ACCTCCCTTA  AACGAAGGCG
4251  AAGAGCCAAG  AATTTACTCG  GCCTTAATTG  ATGGTCATTG  TGAGATTTTA
4301  GAGAATGGTC  GTAGACGTCC  CAAATTTAGA  CAGATAATCA  CCGGTAATCC
4351  AATTCTTGGT  GATGGTAAAT  CAGATAATCA  AAATCATGCT  TTGATTTTTT
4401  ACAGAGGTGA  GTATATTCAA  TTGATTGATG  CTAATCAAGA  CAATTACTTG
4451  GAAGAGTGTT  TGAAAATCAG  GTCTGTCTTA  GCAGAATTTG  AAGAATTGGG
4501  AATTGAGCAA  ATTCATCCTT  ATACTCCTGG  TTTAAAATAT  GAGGACCAAT
```

FIG. 8G

```
4551  CCACAAATCA  TCCTGTTGCA  ATTGTCGGCG  CTAGAGAATA  TATTTCTCA
4601  GAAAACTCTG  GTGTTCTTGG  TGATGTAGCG  GCTGGTAAAG  AACAAACTTT
4651  TGGTACATTA  TTTGCCCGTA  CTTTGGCACA  GATTGGTGGT  AAATTGCATT
4701  ATGGTCATCC  AGATTTTATT  AATGCGACAT  TCATGACTAC  TAGGGGTGGT
4751  GTTTCCAAAG  CACAAAAGGG  TCTACATTTA  AATGAAGATA  TTTATGCCGG
4801  TATGAATGCC  GTACTTCGGG  GTGGTCGTAT  CAAGCATTGC  GAATATTATC
4851  AGTGTGGTAA  AGGTAGAGAT  TTAGGTTTTG  GTACAATTTT  GAATTTCACT
4901  ACTAAGATCG  GTGCTGGTAT  GGGTGAACAA  ATGTTATCTC  GTGAATACTA
4951  TTATTTGGGT  ACGCAATTAC  CTATTGACCG  TTTTTTAACA  TTTTATTATG
5001  CGCATCCAGG  GTTTCACTTG  AATAACTTAT  TTATTCAATT  GTCTCTGCAG
5051  ATGTTCATGT  TAACTTTAGT  GAACTTGCAT  GCTTTGGCTC  ATGAATCCAT
5101  TCTGTGTGTT  TACGATAGGG  ATAAGCCAAT  TACTGATGTT  TTGTATCCAA
5151  TTGGTTGTTA  CAACTTTCAT  CCTGCGATTG  ATTGGGTGAG  ACGTTATACA
```

FIG. 8H

```
5201  CTCTCTATTT  TCATCGTCTT  TTGGATTGCT  TTTGTCCCTA  TTGTCGTTCA
5251  GGAATTAATC  GAGCGTGGTC  TGTGGAAGGC  GACACAAAGA  TTTTCCGTC
5301  ACATTTTATC  TCTATCTCCA  ATGTTTGAAG  TCTTTGCTGG  CCAAATCTAT
5351  TCTTCAGCAC  TGTTAAGTGA  TATCGCTGTG  GGTGGTGCTC  GTTATATTTC
5401  AACAGGTCGT  GGCTTTGCTA  CATCTCGTAT  ACCTTTCTCT  ATTCTTTATT
5451  CAAGATTTGC  GGGTTCAGCC  ATTTATATGG  GATCAAGATC  AATGTTGATG
5501  TTATTATTTG  GTACCGTGGC  ACATTGGCAA  GCTCCACTAT  TATGGTTTTG
5551  GGCATCATTA  TCAGCCTTAA  TCTTTGCACC  ATTCATTTTC  AATCCACATC
5601  AATTTGCTTG  GGAAGATTTT  TTCCTAGACT  ACAGAGATTA  TATCAGATGG
5651  CTGTCAAGAG  GTAATAATAA  GTACCACAGG  AACTCATGGA  TTGGTTATGT
5701  AAGAATGTCG  AGGTCTCGTG  TTACTGGTTT  CAAGCGCAAA  CTGGGTGGTG
5751  ATGAGTCTGA  AAAATCTGCA  GGCGATGCAA  GCAGGGCTCA  TAGAACCAAT
5801  TTAATTATGG  CTGAAATTAT  ACCGTGTGCG  ATTTACGCAG  CAGGTTGTTT
```

FIG. 8I

```
5851  TATTGCCTTC ACGTTTATTA ATGCACAAAC TGGTGTCAAG ACTACTGATG
5901  AAGATAGAGT AAATTCCACC TTACGTATCA TCATTTGCAC CTTGGCGCCT
5951  ATTGTTATCG ATATTGGTGT TTTATTCTTC TGTATGGGTT TGTCATGCTG
6001  CTCTGGCCCT TTGTTGGGCA TGTGCTGCAA GAAAACTGGT TCTGTTATGG
6051  CAGGGATCGC TCACGGTATC GCTGTGTGTG TCCATATTGT CTTTTTCATT
6101  GTCATGTGGG TTTTAGAGGG TTTTAGTTTT GTTAGGATGT TGATTGGCGT
6151  TGTTACATGT ATACAATGTC AAAGGTTGAT TTTTCACTGT ATGACTGTAC
6201  TGTTGCTGAC CCGTGAGTTC AAGAATGATC ACGCTAATAC TGCCTTTTGG
6251  ACAGGCAAAT GGTACAGCAC CGGTTTAGGA TATATGGCAT GGACTCAACC
6301  GACAAGGGAA TTGACTGCAA AAGTCATTGA GCTTTCCGAG TTTGCAGCGG
6351  ATTTGTTTT GGGGCATGTA ATTTGATCT TCCAACTACC AGTCATTTGT
6401  ATTCCAAAGA TAGATAAGTT TCACTCCATC ATGTTATTTT GGTTAAAACC
6451  ATCCCGTCAA ATCCGTCCTC CTATTTACTC TTTGAAACAA GCACGCCTAC
```

FIG. 8J

```
6501  GTAAACGTAT GGTTAGGAGG TATTGCAGCT TGTACTTTTT GGTACTGATC
6551  ATATTCGCGG GATGCATCGT TGGCCCTGCC GTTGCTTCAG CACATGTTCC
6601  AAAAGACCTT GGATCTGGGT TGACGGGTAC TTTCCATAAC TTGGTTCAAC
6651  CAAGGAACGT ATCTAACAAT GATACAGGGT CCCAGATGTC TACTTATAAG
6701  AGTCATTATT ACACTCATAC GCCATCCTTA AAGACCTGGT CTACGATCAA
6751  ATGATTTTTT TAGTTTACAA TCTATTTTTG TTTCTAAGCA AGTTTATCAC
6801  GCAAATACAT AAGTATATTT TTACTTTCTA TTCTTCCTAG TTTATATTTA
6851  TTTCATTGTA ACTTTCTTAG AAGCTCGGTC CTCTCGCTAT ATAGTAGGAT
6901  CTGCAACATA TTTGGATGTG GGTGGGCGTT CTCCTTCTTT TTTAGATGTA
6951  AGGTCCAACA CGTATAACAG GTGATACACA TAGAAAGACA CGTGGAAATA
7001  ACAGTCATTT ACGAATATTT AAAACCTGAG CAACTCCGTC AAATTTGATC
7051  TTAATCTTTT CTGGGGCCCC
```

FIG. 8K

1    MSYNDPNLNG QYYSNGDGTG DGNYPTYQVT QDQSAYDEYG QPIYTQNQLD
51   DGYYDPNEQY VDGTQFPQGQ DPSQDQGPYN NDASYYNQPP NMMNPSSQDG
101  ENFSDFSSYG PPSGTYPNDQ YTPSQMSYPD QDGSSGASTP YGNGVVNGNG
151  QYYDPNAIEM ALPNDPYPAW TADPQSPLPI EQIEDIFIDL TNKFGFQRDS
201  MRNMFDHFMT LLDSRSSRMS PEQALLSLHA DYIGGDTANY KKWYFAAQLD
251  MDDEIGFRNM KLGKLSRKAR KAKKKNKKAM QEASPEDTEE TLNQIEGDNS
301  LEAADFRWKS KMNQLSPFEM VRQIALFLLC WGEANQVRFT PECLCFIYKC
351  ASDYLDSAQC QQRPDPLPEG DFLNRVITPL YRFIRSQVYE IVDGRYVKSE
401  KDHNKVIGYD DVNQLFWYPE GIAKIVMEDG TRLIDLPAEE RYLKLGEIPW
451  DDVFFKTYKE TRSWLHLVTN FNRIWIMHIS VYWMYCAYNA PTFYTHNYQQ
501  LVDNQPLAAY KWATAALGGT VASLIQVAAT LCEWSFVPRK WAGAQHLSRR
551  FWFLCVIMGI NLGPVIFVFA YDKDTVYSTA AHVVGAVMFF VAVATLVFFS
601  VMPLGGLFTS YMKKSTRSYV ASQTFTASFA PLHGLDRWMS YLVWVTVFAA

FIG. 9A

```
 651  KYAESYFFLI LSLRDPIRIL STTSMRCTGE YWWGNKICKV QPKIVLGLMI
 701  ATDFILFFLD TYLWYIVVNT VFSVGKSFYL GISILTPWRN IFTRLPKRIY
 751  SKILATTDME IKYKPKVLIS QIWNAIIISM YREHLLAIDH VQKLLYHQVP
 801  SEIEGKRTLR APTFFVSQDD NNFETEFFPR DSEAERRISF FAQSLSTPIP
 851  EPLPVDNMPT FTVLTPHYAE RILLSLREII REDDQFSRVT LLEYLKQLHP
 901  VEWDCFVKDT KILAEETAAY ENNEDEPEKE DALKSQIDDL PFYCIGFKSA
 951  APEYTLRTRI WASLRSQTLY RTISGFMNYS RAIKLLYRVE NPEIVQMFGG
1001  NADGLERELE KMARRKFKFL VSMQRLAKFK PHELENAEFL LRAYPDLQIA
1051  YLDEEPPLNE GEEPRIYSAL IDGHCEILEN GRRRPKFRVQ LSGNPILGDG
1101  KSDNQNHALI FYRGEYIQLI DANQDNYLEE CLKIRSVLAE FEELGIEQIH
1151  PYTPGLKYED QSTNHPVAIV GAREYIFSEN SGVLGDVAAG KEQTFGTLFA
1201  RTLAQIGGKL HYGHPDFINA TFMTTRGGVS KAQKGLHLNE DIYAGMNAVL
1251  RGGRIKHCEY YQCGKGRDLG FGTILNFTTK IGAGMGEQML SREYYYLGTQ
```

FIG. 9B

1301 LPIDRFLTFY YAHPGFHLNN LFIQLSLQMF MLTLVNLHAL AHESILCVYD
1351 RDKPITDVLY PIGCYNFHPA IDWVRYTLS IFIVFWIAFV PIVVQELIER
1401 GLWKATQRFF RHILSLSPMF EVFAGQIYSS ALLSDIAVGG ARYISTGRGF
1451 ATSRIPFSIL YSRFAGSAIY MGSRSMLMLL FGTVAHWQAP LLWFWASLSA
1501 LIFAPFIFNP HQFAWEDFFL DYRDYIRWLS RGNNKYHRNS WIGYVRMSRS
1551 RVTGFKRKLV GDESEKSAGD ASRAHRTNLI MAEIIPCAIY AAGCFIAFTF
1601 INAQTGVKTT DEDRVNSTLR IIICTLAPIV IDIGVLFFCM GLSCCSGPLL
1651 GMCCKKTGSV MAGIAHGIAV VVHIVFFIVM WVLEGFSFVR MLIGVVTCIQ
1701 CQRLIFHCMT VLLLTREFKN DHANTAFWTG KWYSTGLGYM AWTQPTRELT
1751 AKVIELSEFA ADFVLGHVIL IFQLPVICIP KIDKFHSIML FWLKPSRQIR
1801 PPIYSLKQAR LRKRMVRRYC SLYFLVLIIF AGCIVGPAVA SAHVPKDLGS
1851 GLTGTFHNLV QPRNVSNNDT GSQMSTYKSH YYTHTPSLKT WSTIK

FIG. 9C

```
  1 TACTGTATCGGTTTCAAGTCTGCTGCTCCCGAGTACACGCTTCGCACCCGTATTTGGTCC
 60
    1 Y C I G F K S A A P E Y T L R T R I W S   20

61 TCGCTGCGTTCGCAAACTCTTTACAGAACTGTATCCGGGATGATGAACTATAGCAGAGCT
120
   21 S L R S Q T L Y R T V S G M M N Y S R A   40

121 ATCAAGCTCCTCTACCGTGTGGAGAACCCGGAAGTCGTCCAGATGTTCGGTGGTAATTCT
180
   41 I K L L Y R V E N P E V V Q M F G G N S   60

181 GAGAAGCTGGAACATGAGCTCGAGAGGATGGCCCGTCGCAAGTTCAAGATCTGTGTTTCA  240
   61 E K L E H E L E R M A R R K F K I C V S   80

241 ATGCAGCGGGTATGCCAAATTCACAAAGAAGAACGTGAGAACACAGAGTTCCTCCTCCGA  300
   81 M Q R Y A K F T K E E R E N T E F L L R  100

301 GCCTACCCCGACCTGCAGATTGCCTATCTCGATGAGGAACCTCCAGCCAACGAGGGTGAA  360
  101 A Y P D L Q I A Y L D E E P P A N E G E  120

361 GAGCCGCGTCTCTACTCTGCTTTGATTGATGGACACTGTGAGCTGCTCGAGAATGGCATG
420
  121 E P R L Y S A L I D G H C E L L E N G M  140
```

FIG. 10A

```
421  CGGAAGCCCAAGTTCAGGATCCAGTCTCTCCGGAAACCCGATCCTTGGTGACGGCAAGTCT  480
141   R  K  P  K  F  R  I  Q  L  S  G  N  P  I  L  G  D  G  K  S    160

481  GACAACCAAAACCACTCGATCATTTTCTACCGCGGTGAATACATTCAGGTCATTGATGCC  540
161   D  N  Q  N  H  S  I  I  F  Y  R  G  E  Y  I  Q  V  I  D  A    180

541  AACCAAGACAACTATCTCGAAGAGTGCTTGAAAATCCGAAGCGTTCTTGCTGAGTTTGAG  600
181   N  Q  D  N  Y  L  E  E  C  L  K  I  R  S  V  L  A  E  F  E    200

601  GAATTGACCACCGACAATGTCTCGCCTTACACTCCTGGGCGTTGCCTCTTCCCTCTGAAGCT  660
201   E  L  T  T  D  N  V  S  P  Y  T  P  G  V  A  S  S  S  E  A    220

661  CCTGTTGCTATCCTTGGTGCCCGTGAATACATTTCTCAGAGAACATTGGTGTACTTGGT  720
221   P  V  A  I  L  G  A  R  E  Y  I  F  S  E  N  I  G  V  L  G    240

721  GACGTTGCCGCCGGTAAAGAACAGACATTGGTACCCTGTTGCTCGTACTCTTGCTCAG  780
241   D  V  A  A  G  K  E  Q  T  F  G  T  L  F  A  R  T  L  A  Q    260

781  ATTGGGCGGAAAGCTCCATTATGGTCACCCTGATTCCTGAATGGTATCTTCATGACTACC  840
261   I  G  G  K  L  H  Y  G  H  P  D  F  L  N  G  I  F  M  T  T    280
```

FIG. 10B

841
AGAGGTGGTATCTCCAAGGCTCAAAAAGGTCTACACCTTAACGAGGATATCTACGCTGGT 900
281  R  G  G  I  S  K  A  Q  K  G  L  H  L  N  E  D  I  Y  A  G    300

901 ATGAACGCCATGGTTCGTGGTGGCCGCATCAAGCACTGCGAGTACTTCCAGTGTGGTAAG 960
301  M  N  A  M  V  R  G  G  R  I  K  H  C  E  Y  F  Q  C  G  K    320

961 GGTCGTGATCTTGGTTTCGGTTCCATTCTAATTTCACCACTAAGATTGGCACTGGTATG 1020
321  G  R  D  L  G  F  G  S  I  L  N  F  T  T  K  I  G  T  G  M    340

1021
GGTGAGCAAATGCTATCAAGAGAGTACTACTACTKGGGTACTCAACTGCCACTCGACCGA 1080
341  G  E  Q  M  L  S  R  E  Y  Y  Y  X  G  T  Q  L  P  L  D  R    360

1081
TTCCTGTCCTTTACTATGYTCACCCTGGATTCCACATCAACACATGTTTATTATGTTG 1140
361  F  L  S  F  Y  Y  X  H  P  G  F  H  I  N  N  M  F  I  M  L    380

1141
TCTGTGCAAATGTTCATGATTGTTCTGATCAACCTGGGGCCCTGAAGCACGAAACCATC 1200
381  S  V  Q  M  F  M  I  V  L  I  N  L  G  A  L  K  H  E  T  I    400

1201
AACTGCAACTACAACTCCGACCTGCCCATTACCGATCCACTTATGCCAACGTTCTGCGCG 1260
401  N  C  N  Y  N  S  D  L  P  I  T  D  P  L  M  P  T  F  C  A    420

FIG. 10C

```
1261
CCTCTCACTCCTATCATCAACTGGGTCAACCGCTGTGTTATTTCGATTTCATCGTTTC  1320
421  P  L  T  P  I  I  N  W  V  N  R  C  V  I  S  I  F  I  V  F   440

1321
TTCATTCGTTGTTCCTTTGGCGTCTGTTCAAGAATTGACTGAAAGAGGACTCTGGCGTATG  1380
441  F  I  S  F  V  P  L  A  V  Q  E  L  T  E  R  G  L  W  R  M   460

1381 GCAACGCGTCTGGCCAAACATTTCGGATCTTCTCCTTCATGTTCGAGGTGTTGTTTGT
1440
461  A  T  R  L  A  K  H  F  G  S  F  S  F  M  F  E  V  F  V  C   480

1441
CAAATCTATTCCAACGCTGTGCACCAAAACTGTCTTCGGTGGAGCGCGCTACATCGCT  1500
481  Q  I  Y  S  N  A  V  H  Q  N  L  S  F  G  G  A  R  Y  I  A   500

1501  ACCGGTCGTGGTTTCGCAACTGCTCGTATCCCATTCGGCGTTCTGTACTCTCGGGTTGCG
1560
501  T  G  R  G  F  A  T  A  R  I  P  F  G  V  L  Y  S  R  F  A   520

1561
GGACCTTCAATTACACCGGTTCCGTTCCGTCTGCTGATCATGCTGCTCTTCTCAACCTCAACT  1620
521  G  P  S  I  Y  T  G  F  R  L  L  I  M  L  L  F  S  T  S  T   540

1621  ACCTGGACTGCCTCTCTCATTGGTTCTGGGTCTCTCTCTCTCGCCCTTTGCATCTCCCCA
1680
541  T  W  T  A  S  L  I  W  F  W  V  S  L  L  A  L  C  I  S  P   560
```

FIG. 10D

```
1681
TTCCTTTTCAACCCTCACCAGTTGCCTGGAACGACTTCTTCATCGATTACCGTGACTAC 1740
561  F L F N P H Q F A W N D F F I D Y R D Y    580

1741 ATCCGATGGCTTTCGCGGCGGTAACTCTCGCTCACACGGCATCCTCATGGATTGGCTTCTGC
1800
581  I R W L S R G N S R S H A S S W I G F C    600

1801 CGTTTGTCGCGTACTCGGATCACTGGTACAAGCGCAAGCTTCTCGGTGTGCCGTCGGAG
1860
601  R L S R T R I T G Y K R K L L G V P S E    620

1861
AAAGGATCAGGTGACGTTCCCAGAGCTCGTATTACCAACATTTTCTTCAGCGAAATTGTC 1920
621  K G S G D V P R A R I T N I F F S E I V    640

1921 GCTCCTCTAGTCCTCGTTGCTGTTACCCTCGTTCCATACCTCTACATCAATTCTCGGACT
1980
641  A P L V L V A V T L V P Y L Y I N S R T    660

1981
GGTGTGAGCGCTGATGTGGACGGGGGCAATGACCCTCACGATGCCATTTGCCTATTGCC 2040
661  G V S A D V D G G N D P H D A I L R I A    680

2041 ATTGTAGCATTTGGACCTATTGGTATCAATGCCGGTGTTGCTGTTTTCTTGGTATG
2100
681  I V A F G P I G I N A G V A A V F F G M    700
```

FIG. 10E

```
2101 GCATGCTGCATGGGTCCCATCCTGAGCATGTGCTGCAAGAAGTTCGGTGCTGTGTTGGCG
     2160
 701 A C C M G P I L S M C C K K F G A V L A   720

2161 GCTATTGCCCACGGCGATTGCTGTGATCATCTTGCTTGTCATCTTTGAAGTCATGTTCTTC
     2220
 721 A I A H A I A V I I L L V I F E V M F F   740

2221
CTCGAACACTGGTCTTGGCCCCGGTGCGTCATGGGCATGATCGCCATGGGTGCCATTCAA  2280
 741 L E H W S W P R C V M G M I A M G A I Q   760

2281
CGTTTCGTCTACAAACTTATTATCGCGCTCGCTCTTACCCGAGAGTTCAAGCATGACCAG  2340
 761 R F V Y K L I I A L A L T R E F K H D Q   780

2341
TCGAACATCGCATGGTGGACTGGAAAAATGGTACAACAACATGGGGTTGGGACTCTCTCTCTCAA  2400
 781 S N I A W W T G K W Y N M G W D S L S Q   800

2401
CCGGGCCGAGAGTTCCTCTGCAAGATCACGGAGTTGGGCTATTTCTCAGCAGACTTCGTC  2460
 801 P G R E F L C K I T E L G Y F S A D F V   820

2461
ATTGGTCATCTCCTATTGTTCATTATGCTGCCCGCTCTTTGTGTTCCTTACATTGACAAG  2520
 821 I G H L L L F I M L P A L C V P Y I D K   840
```

FIG. 10F

2521 TTTCACTCAGYCATTCTCTTTTGGGTCCSGCCCAAGGTAAGAACC 2565
841  F  H  S  X  I  L  F  W  V  X  P  K  V  R  T  855

FIG. 10G

```
          10         20         30         40         50         60
           *          *          *          *          *          *
GGT ACC ATC TAC TGG ATG TAC ACT GCT TAC AAC TCC CCA ACC TTG TAT ACT AAA CAT TAT 70         80         90        100        110        120
           *          *          *          *          *          *
GTC CAA ACC ATA AAT CAA CAA CCA CTT GCT TCG TCA AGA TGG GCT GCT TGT GCC ATT GGT 130        140        150        160        170        180
           *          *          *          *          *          *
GGT GTT CTT GCT TCA TTT ATT CAA ATT CTT GCC ACA CTT TTC GAA TGG ATT TTC GTG CCT 190        200        210        220        230        240
           *          *          *          *          *          *
AGA GAA TGG GCC GGT GCT CAA CAT TTG AGT CGT CGT ATG CTA TTT TTG GTG TTA ATT TTC 250        260        270        280        290        300
           *          *          *          *          *          *
TTA CTC AAT TTG GTT CCA CCA GTT TAT ACA TTC AAA TTA CCA AAA TTG GTG ATT TAT TCG 310        320        330        340        350        360
           *          *          *          *          *          *
AAA TCG GCA TAT GCT GTG TCG ATT GTT GGA TTT TTC ATT GCT GTG GCC ACT TTA GTA TTC 370        380        390        400        410        420
           *          *          *          *          *          *
TTT GCC GTC ATG CCA TTG GGT GGT TTA TTC ACT TCA TAC ATG AAC AAG AGA TCA AGA AGA 430        440        450        460        470        480
           *          *          *          *          *          *
TAT ATT GCA TCA CAA ACA TTT ACT GCC AAC TAC ATT AAA TTG AAA GGT TTA GAT ATG TGG 490        500        510        520        530        540
           *          *          *          *          *          *
TAT ATT GCA TCA CAA ACA TTT ACT GCC AAC TAC ATT AAA TTG AAA GGT TTA GAT ATG TGG 550        560        570        580        590        600
           *          *          *          *          *          *
ATG TCT TAT TTG TTA TGG TTT TTG GTT TTC CTT GCC AAA TTG GTT GAA TCT TAT TTC TTC
```

FIG.11A

```
       610         620         630         640         650         660
        *           *           *           *           *           *
TTG ACT TTG TCT TTA AGA GAT CCT ATT AGA AAC TTG TCG ACC ATG ACA ATG AGA TGT GTT 670         680         690         700         710         720
        *           *           *           *           *           *
GGT GAA GTT TGG TAC AAA GAT ATT GTT TGT AGA AAC CAA GCC AAG ATT GTC TTG GGG TTG 730         740         750         760         770         780
        *           *           *           *           *           *
ATG TAT CTT GTT GAT TTG TTA TTG TTC TTT TTG GAT ACT TAT ATG TGG TAC ATT ATT TGT 790         800         810         820         830         840
        *           *           *           *           *           *
AAC TGT ATC TTC TCC ATT GGT CGT TCA TTC TAT TTG GGT ATT TCC ATT TTG ACT CCT TGG 850         860         870         880         890         900
        *           *           *           *           *           *
AGA AAC ATT TTC ACC AGA TTG CCA AAG AGA ATT TAT TCC AAG ATT TTA GCT ACC ACG GAA 910         920         930         940         950         960
        *           *           *           *           *           *
ATG GAA ATC AAA TAT AAA CCT AAA GTT TTG ATT TCA CAA ATT TGG AAT GCC ATT GTT ATT 970         980         990        1000        1010        1020
        *           *           *           *           *           *
TCC ATG TAC AGA GAA CAC TTG TTA GCC ATT GAT CAC GTT CAA AAA TTA TTG TAT CAT CAA 1030        1040        1050        1060        1070        1080
        *           *           *           *           *           *
GTC CCA TCT GAA ATT GAA GGT AAG AGA ACT TTG AGA GCT CCA ACT TTC TTT GTT TCT CAA 1090        1100        1110        1120        1130        1140
        *           *           *           *           *           *
GAT GAC AAC AAT TTT GAA ACG GAA TTT TTC CCA AGA AAT TCT GAA GCT GAA AGA AGA ATT 1150        1160        1170        1180        1190        1200
        *           *           *           *           *           *
TCA TTT TTC GCT CAA TCT TTG GCT ACA CCA ATG CCA GAA CCA TTA CCA GTT GAT AAT ATG
```

FIG.11B

```
     1210          1220          1230          1240          1250          1260
      *             *             *             *             *             *
CCA ACT TTT ACT GTT TTT ACT CCT CAT TAT TCG GAA AAG ATT TTG TTA TCT TTG AGA GAA 1270          1280          1290          1300          1310          1320
      *             *             *             *             *             *
ATC ATT AGA GAA GAT GAT CAA TTC TCA AGA GTG ACA TTA TTG GAA TAT TTG AAA CAA TTA 1340          1350          1360          1370          1380          1390
      *             *             *             *             *             *
CAT CCA GTT GAA TGG GAT TGT TTT GTT AAG GAC ACC AAG ATT TTG GCT GAA GAA ACT GCT 1400          1410          1420          1430          1440          1450
      *             *             *             *             *             *
GCT TAT GAA AAT GGT GAT GAT TCT GAA AAA TTA TCT GAA GAT GGA TTG AAA TCC AAG ATT 1460          1470          1480          1490          1500          1510
      *             *             *             *             *             *
GAT GAT TTA CCA TTC TAT TGT ATT GGT TTC AAG TCT GCC GCC CCT GAA TAT ACT TTA AGA 1520          1530          1540          1550          1560          1570
      *             *             *             *             *             *
ACA AGA ATT TGG GCT TCA TTG AGA TCC CAA ACT TTG TAC AGA ACT GTA TCT GGG TTT ATG 1580          1590          1600          1610          1620          1630
      *             *             *             *             *             *
AAT TAT GCC AGA GCC ATT AAA TTG TTA TAC AGA GTG GAA AAC CCA GAA TTG GTT CAA TAT 1640          1650          1660          1670          1680          1690
      *             *             *             *             *             *
TTC GGT GGT GAT CCT GAA GGA TTA GAA TTA GCT TTA GAA AGA ATG GCC AGA AGA AAG TTT 1700          1710          1720          1730          1740          1750
      *             *             *             *             *             *
AGA TTT TTG GTT TCT ATG CAA AGA TTG TCT AAA TTC AAA GAT GAT GAA ATG GAA AAT GCT 1760          1770          1780          1790          1800          1810
      *             *             *             *             *             *
GAG TTC TTA TTG CGT GCT TAC CCT GAT TTG CAA ATT GCT TAC TTG GAT GAA GAA CCG GCT
```

FIG.11C

```
             1820         1830         1840         1850         1860         1870
               *            *            *            *            *            *
         TTG AAT GAG GAC GAG GAA CCA AGA GTA TAC TCT GCC TTG ATT GAT GGT CAT TGT GAA ATG 1880         1890         1900         1910         1920         1930
               *            *            *            *            *            *
         TTA GAA AAT GGT AGA CGT CGT CCT AAA TTC AGA GTT CAA TTG TCT GGT AAT CCA ATT TTG 1940         1950         1960         1970         1980         1990
               *            *            *            *            *            *
         GGT GAT GGT AAA TCT GAT AAT CAA AAT CAT GCG GTT ATT TTC CAT AGA GGT GAA TAT ATT 2000         2010         2020         2030         2040         2050
               *            *            *            *            *            *
         CAA TTG ATT GAT GCT AAT CAA GAT AAT TAT TTG GAA GAA TGT TTG AAG ATT AGA TCA GTT 2060         2070         2080         2090         2100         2110
               *            *            *            *            *            *
         TTG GCT GAA TTT GAA GAA ATG AAT GTT GAA CAT GTT AAT CCA TAT GCA CCA AAT TTG AAA 2120         2130
               *            *
         TCT GAA GAT AAT AAC ACC AAG AAG GAT CC
```

FIG.11D

|  | 10 | 20 | 30 | 40 | 50 | 60 |
|---|---|---|---|---|---|---|
| Gly Thr | Ile Tyr | Trp Met Tyr | Thr Ala Tyr | Asn Ser Pro | Thr Leu Tyr | Thr Lys His Tyr |

|  | 70 | 80 | 90 | 100 | 110 | 120 |
|---|---|---|---|---|---|---|
| Val Gln Thr | Ile Asn Gln | Gln Pro Leu | Ala Ser Ser | Arg Trp Ala | Ala Cys Ala | Ile Gly |

|  | 130 | 140 | 150 | 160 | 170 | 180 |
|---|---|---|---|---|---|---|
| Gly Val Leu | Ala Ser Phe | Ile Gln Ile | Leu Ala Thr | Leu Phe Glu | Trp Ile Phe | Val Pro |

|  | 190 | 200 | 210 | 220 | 230 | 240 |
|---|---|---|---|---|---|---|
| Arg Glu Trp | Ala Gly Ala | Gln His Leu | Ser Arg Arg | Met Leu Phe | Leu Val Leu | Ile Phe |

|  | 250 | 260 | 270 | 280 | 290 | 300 |
|---|---|---|---|---|---|---|
| Leu Leu Asn | Leu Val Pro | Pro Val Tyr | Thr Phe Gln | Ile Thr Lys | Leu Val Ile | Tyr Ser |

|  | 310 | 320 | 330 | 340 | 350 | 360 |
|---|---|---|---|---|---|---|
| Lys Ser Ala | Tyr Ala Val | Ser Ile Val | Gly Phe Phe | Ile Ala Val | Ala Thr Leu | Val Phe |

|  | 370 | 380 | 390 | 400 | 410 | 420 |
|---|---|---|---|---|---|---|
| Phe Ala Val | Met Pro Leu | Gly Gly Leu | Phe Thr Ser | Tyr Met Asn | Lys Arg Ser | Arg Arg |

|  | 430 | 440 | 450 | 460 | 470 | 480 |
|---|---|---|---|---|---|---|
| Tyr Ile Ala | Ser Gln Thr | Phe Thr Ala | Asn Tyr Ile | Lys Leu Lys | Gly Leu Asp | Met Trp |

|  | 490 | 500 | 510 | 520 | 530 | 540 |
|---|---|---|---|---|---|---|
| Met Ser Tyr | Leu Leu Trp | Phe Leu Val | Phe Leu Ala | Lys Leu Val | Glu Ser Tyr | Phe Phe |

|  | 550 | 560 | 570 | 580 | 590 | 600 |
|---|---|---|---|---|---|---|
| Leu Thr Leu | Ser Leu Arg | Asp Pro Ile | Arg Asn Leu | Ser Thr Met | Thr Met Arg | Cys Val |

FIG.12A

|     | 610 | 620 | 630 | 640 | 650 | 660 |
|-----|-----|-----|-----|-----|-----|-----|
| Gly | Glu | Val | Trp | Tyr | Lys | Asp | Ile | Val | Cys | Arg | Asn | Gln | Ala | Lys | Ile | Val | Leu | Gly | Leu |

Gly Glu Val Trp Tyr Lys Asp Ile Val Cys Arg Asn Gln Ala Lys Ile Val Leu Gly Leu 670  680  690  700  710  720
Met Tyr Leu Val Asp Leu Leu Leu Phe Phe Leu Asp Thr Tyr Met Trp Tyr Ile Ile Cys 730  740  750  760  770  780
Asn Cys Ile Phe Ser Ile Gly Arg Ser Phe Tyr Leu Gly Ile Ser Ile Leu Thr Pro Trp 790  800  810  820  830  840
Arg Asn Ile Phe Thr Arg Leu Pro Lys Arg Ile Tyr Ser Lys Ile Leu Ala Thr Thr Glu 850  860  870  880  890  900
Met Glu Ile Lys Tyr Lys Pro Lys Val Leu Ile Ser Gln Ile Trp Asn Ala Ile Val Ile 910  920  930  940  950  960
Ser Met Tyr Arg Glu His Leu Leu Ala Ile Asp His Val Gln Lys Leu Leu Tyr His Gln 970  980  990  1000  1010  1020
Val Pro Ser Glu Ile Glu Gly Lys Arg Thr Leu Arg Ala Pro Thr Phe Phe Val Ser Gln 1030  1040  1050  1060  1070  1080
Asp Asp Asn Asn Phe Glu Thr Glu Phe Phe Pro Arg Asn Ser Glu Ala Glu Arg Arg Ile 1090  1100  1110  1120  1130  1140
Ser Phe Phe Ala Gln Ser Leu Ala Thr Pro Met Pro Glu Pro Leu Pro Val Asp Asn Met 1150  1160  1170  1180  1190  1200
Pro Thr Phe Thr Val Phe Thr Pro His Tyr Ser Glu Lys Ile Leu Leu Ser Leu Arg Glu

FIG.12B

```
        1210        1220        1230        1240        1250        1260
         *           *           *           *           *           *
Ile Ile Arg Glu Asp Asp Gln Phe Ser Arg Val Thr Leu Leu Glu Tyr Leu Lys Gln Leu 1270        1280        1290        1300        1310        1320
         *           *           *           *           *           *
His Pro Val Glu Trp Asp Cys Phe Val Lys Asp Thr Lys Ile Leu Ala Glu Glu Thr Ala 1330        1340        1350        1360        1370        1380
         *           *           *           *           *           *
Ala Tyr Glu Asn Gly Asp Asp Ser Glu Lys Leu Ser Glu Asp Gly Leu Lys Ser Lys Ile 1390        1400        1410        1420        1430        1440
         *           *           *           *           *           *
Asp Asp Leu Pro Phe Tyr Cys Ile Gly Phe Lys ser Ala Ala Pro Glu Tyr Thr Leu Arg 1450        1460        1470        1480        1490        1500
         *           *           *           *           *           *
Thr Arg Ile Trp Ala Ser Leu Arg Ser Gln Thr Leu Tyr Arg Thr Val Ser Gly Phe Met 1510        1520        1530        1540        1550        1560
         *           *           *           *           *           *
Asn Tyr Ala Arg Ala Ile Lys Leu Leu Tyr Arg Val Glu Asn Pro Glu Leu Val Gln Tyr 1570        1580        1590        1600        1610        1620
         *           *           *           *           *           *
Phe Gly Gly Asp Pro Glu Gly Leu Glu Leu Ala Leu Glu Arg Met Ala Arg Arg Lys Phe 1630        1640        1650        1660        1670        1680
         *           *           *           *           *           *
Arg Phe Leu Val Ser Met Gln Arg Leu Ser Lys Phe Lys Asp Asp Glu Met Glu Asn Ala 1690        1700        1710        1720        1730        1740
         *           *           *           *           *           *
Glu Phe Leu Leu Arg Ala Tyr Pro Asp Leu Gln Ile Ala Tyr Leu Asp Glu Glu Pro Ala
```

FIG.12C

```
            1750        1760        1770        1780        1790        1800
             *           *           *           *           *           *
Leu Asn Glu Asp Glu Glu Pro Arg Val Tyr Ser Ala Leu Ile Asp Gly His Cys Glu Met 1810        1820        1830        1840        1850        1860
             *           *           *           *           *           *
Leu Glu Asn Gly Arg Arg Arg Pro Lys Phe Arg Val Gln Leu Ser Gly Asn Pro Ile Leu 1870        1880        1890        1900        1910        1920
             *           *           *           *           *           *
Gly Asp Gly Lys Ser Asp Asn Gln Asn His Ala Val Ile Phe His Arg Gly Glu Tyr Ile 1930        1940        1950        1960        1970        1980
             *           *           *           *           *           *
Gln Leu Ile Asp Ala Asn Gln Asp Asn Tyr Leu Glu Glu Cys Leu Lys Ile arg Ser Val 1990        2000        2010        2020        2030        2040
             *           *           *           *           *           *
Leu Ala Glu Phe Glu Glu Met Asn Val Glu His Val Asn Pro Tyr Ala Pro Asn Leu Lys 2050        2060
             *           *
Ser Glu Asp Asn Thr Lys Lys Asp Pro
```

FIG.12D

List of Strains

| Strain Name | Relevant Properties | MY No. | ATCC |
|---|---|---|---|
| YFK0688-14B | MATalpha *fks1-1* (506s) | none | |
| YFK0931-03B | MATalpha cnb1::LYS2 fks1-1/pDL1 (506s) | none | |
| YFK0931-07B | MATa cnb1::LYS2 fks1-1/pDL1 (506s) | none | |
| YFK0931-10C | MATa cnb1::LYS2 fks1-1/pDL1 (506s) | none | |
| YFK0932-01C | MATalpha cnb1::LYS2 fks1-1/pDL1 (506s) | none | |
| YFK0996-11B | MATa fks1-1 pcr1(fks2-1)/pDL1 (506s 560R) | none | |
| YFK0996-23D | MATa pcr1(fks2-1) cnb1::LYS2 | none | |
| YFF2720 | MATalpha fks2::TRP1 | none | |
| YFF2721 | MATalpha fks2::TRP1 | none | |
| YFK0978 (YM148) | MATa cnb1::LYS2 fks1-1 pcr1(fks2-1)/pDL1 (506s 560R) | MY2256 | xxx |
| YFK1088-23B | MATa pcr1(fks2-1) (560R) | MY2257 | xxx |
| YFK1088-16D | MATalpha pcr1(fks2-1) (560R) | MY2258 | xxx |
| YFK1087-20B | MATalpha fks1-1 pcr1(fks2-1) (506s 560R) | MY2259 | xxx |
| YFK1087-20A | MATa fks1-1 pcr1(fks2-1) (506s 560R) | MY2260 | xxx |

F I G. 13

DNA ENCODING 1,3 BETA-D GLUCAN SYNTHASE SUBUNITS

CROSS-RELATED TO OTHER APPLICATIONS

This is a continuation-in-part of U.S. Ser. No. 08/135,149 filed Oct. 12, 1993, now abandoned, and a continuation-in-part of U.S. Ser. No. 08/135,148 filed Oct. 12, 1993, now abandoned and a continuation-in-part of U.S. Ser. No. 08/135,150 filed Oct. 12, 1993, now abandoned, each of which is expressly incorporated by reference.

SUMMARY OF THE INVENTION

DNA molecules encoding proteins involved in biosynthesis of 1,3-beta-D glucan are identified, cloned, expressed and used in in vitro assays to screen for antifungal compounds, including compounds that affect cell wall biosynthesis. The invention includes the purified DNA molecules, assays employing the DNA molecules, proteins encoded by the DNA molecules, cells expressing the DNA molecules and altered forms of the molecule.

BRIEF DESCRIPTION OF THE DRAWINGS

FIG. 1 is a restriction map of plasmid pFF119.

FIG. 2 is a restriction map of plasmid pFF334.

FIGS. 5A–5D show the DNA sequence and putative amino acid translation of part of the fksA gene. The DNA sequence depicted is SEQ. ID. NO.:5. The amino acid sequence depicted is SEQ. ID. NO.:6.

FIGS. 6A–6L show the FKS1 DNA sequence. The DNA sequence depicted is SEQ. ID. NO.:1.

FIGS. 7A–7C show the amino acid sequence of FKS1 protein. The amino acid sequence depicted is SEQ. ID. NO.:2.

FIGS. 8A–8K show the FKS2 DNA sequence. The DNA sequence depicted is SEQ. ID. NO.:3.

FIGS. 9A–9C show the amino acid sequence of FKS2 protein. The amino acid sequence depicted is SEQ. ID. NO.:4.

FIGS. 10A–10G show the DNA and amino acid sequences of fksA. The DNA sequence depicted is SEQ. ID. NO.:5. The amino acid sequence depicted is SEQ. ID. NO.:6.

FIGS. 11A–11D show the DNA sequence of an FKS1 homolog isolated from *Candida albicans*. The DNA sequence depicted is SEQ. ID. NO.:7.

FIGS. 12A–12D show the amino acid sequence of an FKS1 homolog of *C. albicans*. The amino acid sequence depicted is SEQ. ID. NO.:8.

FIG. 13 is a partial list of yeast strains.

BACKGROUND OF THE INVENTION

Figure 3:
FIG. 3 is a restriction map of 11.0 kb EcoRI insert of pGS3.

DNA molecules encoding proteins involved in biosynthesis of 1,3-beta-D glucan are identified, cloned, expressed and used in in vitro assays to screen for antifungal compounds, including compounds that affect cell wall biosynthesis. The invention includes but is not limited to the purified DNA molecules, assays employing the DNA molecules, proteins encoded by the DNA molecules, cells expressing the DNA molecules and altered forms of the molecule.

The present application is directed to purified DNA fragments that contain a gene which reverses the mutant phenotypes of several different strains of *Saccharomyces cerevisiae*. The gene is called FKS1, for FK506 sensitivity gene 1, and is also known as ETG1 (echinocandin target gene 1). Echinocandins are acyl-substituted cyclic hexapeptides that inhibit the synthesis of 1,3-beta-D-glucan in many fungi. FKS2 is a homolog of FKS1. FKS1 was cloned from a genomic library of *Saccharomyces cerevisiae*. The properties of FKS1 suggest that it encodes a subunit of 1,3-β-D glucan synthase. Proteins encoded by FKS1 or homologs thereof represent possible targets for drug therapy for fungal disease. The invention includes homologs such as FKS2, which also encodes a target of the echinocandins, and closely-related genes from pathogenic fungi such as *Aspergillus fumigatus, Candida albicans* and *Cryptococcus neoformans*.

The invention comprises a gene which reverses the drug-related phenotypes of distinct mutants of *S. cerevisiae*. Several mutant strains were identified by their altered sensitivity to specific classes of fungal cell wall inhibitors, while another mutant strain is hypersensitive to the immunosuppressive compounds FK506 and cyclosporin A.

Understanding the mode of action of novel therapeutic compounds employs a variety of experimental approaches involving both biochemistry and genetics. One approach is to try to isolate organisms resistant or sensitive to test compounds. Such mutants can then sometimes be used to isolate genes encoding the drug targets. A general description of some of the relevant areas of yeast biology and the mutant organisms follows.

FK506 and cyclosporin A (CsA) are potent immunosuppressants that inhibit an intermediate $Ca^{2+}$-dependent step in T cell activation and block interleukin-2 (IL-2) production (for a review, see Sigal et al., 1992, *Ann. Rev. Immunol.*, 10:519–560). FK506 binds to a family of proteins known as FK506 binding proteins (FKBP) while CsA binds to members of another family of proteins called cyclophilins. The resulting drug-receptor complex (FKBP-FK506 or cyclophilin-CsA) binds and inhibits calcineurin, a $Ca^{2+}$-and calmodulin-dependent protein phosphatase, suggesting that inhibition of calcineurin may be a mechanism of immunosuppression (Liu et al., 1991. *Cell,* 66:807–815).

FK506 and CsA are also antibiotics that inhibit the growth of certain strains of yeast and fungi. The antifungal properties of these drugs and the existence of FKBP, cyclophilins and calcineurins in yeast and fungi have prompted genetic examinations of the mode of action of the drugs in these organisms.

Using FK506 as a screening agent, hypersensitive mutants were isolated. The fks1-1 mutation discovered in this screen was used to clone the FKS1 gene. A homolog of FKS1 (FKS2) was also discovered and cloned. Examples describing the discovery of this mutation, its use, and the cloning of FKS1, FKS2 and homologs of these genes are provided below.

CsA supersensitive mutants have been reported, but their relationship to FKS1 or FKS2, if any, was not disclosed (Koser, P. K. et al., 1991. *Gene*, 108:73–80).

The fungal cell wall is a complex structure involved in a variety of vital cellular processes. Vegetative growth, morphogenesis, uptake and secretion of macromolecules and protection against osmotic changes are affected by changes in the composition and integrity of the cell wall. It might be expected that antifungal compounds which act via the inhibition of cell wall synthesis, a process essential to fungi and absent from mammalian cells, would produce an ideal combination of fungicidal activity and low mammalian toxicity.

Efforts from a large number of laboratories have been directed towards the identification of such agents, although compounds of this type have not yet been introduced into clinical practice. The walls of fungi are composed of a number of polymers: chitin, alpha- and beta-glucans, and mannoproteins are all potential targets for antifungal therapy.

A major class of beta-glucan inhibitors is comprised of several lipopeptide antibiotics including aculeacin A, echinocandin B and the pneumocandins. These compounds are all cyclic hexapeptides containing a non-polar fatty acid side chain. Fungicidal activity of the natural products is largely limited to yeasts. Echinocandins are fungicidal by virtue of their ability to inhibit whole cell synthesis of 1,3-beta-D glucan, which disrupts the integrity of the cell wall and causes whole yeast cells to lyse. Echinocandins inhibit in vitro polymerization of glucose into 1,3-beta-D glucan, a reaction that can be catalyzed by mixed membrane fractions from several types of fungi, such as *C. albicans, Aspergillus fumigatus* and *Neurospora crassa.*

A second structural class of beta-glucan synthesis inhibitors, the papulacandins and chaetiacandin, contain a glycoside component connected to an aromatic ring system and two long chain fatty acids. These compounds have the same mode of action as the echinocandins. Chemical modification efforts in addition to natural product discovery programs have been aimed at the identification of a clinically useful echinocandin, papulacandin, or chaetiacandin. It is likely that analogues will eventually be incorporated into clinical use.

Matsumoto et al., reported that *Pneumocystis carinii*, a major cause of pneumonia-related death in AIDS patients in the United States, has beta-glucan in the wall of its cyst form (Matsumoto, Y., et al., 1989. *J. Protozool.*, 36:21S–22S). Inhibitors of beta-glucan synthesis, such as papulacandins and echinocandins, might therefore have efficacy in treating *P. carinii* infections. Schmatz et al., reported that in a rat model of *P. carinii* pneumonia, L-671,329 (an echinocandin) and L-687,781 (a papulacandin) were both effective in reducing the number of cysts in the lungs of infected rats (D. M. Schmatz et al., 1990. *PNAS*, 87:5950–5954). These results suggest that beta-glucan synthesis is a viable target for therapeutics useful in the treatment of *P. carinii* infections.

There have been several efforts to isolate bona fide drug resistant strains of *S. cerevisiae* affected in beta-glucan synthesis. Mutants that have been isolated include acu1 (Mason, M., et al., 1989. *Yeast Cell Biology meeting*, Aug. 15–Aug. 20, 1989, Cold Spring Harbor Laboratory, Cold Spring Harbor, N.Y. Abstract #154); acr1/2/3/4 (Font de Mora, J., et al., 1991. *Antimicrob. Agents Chemother.*, 35:12 2596–2601); and pap1 (Duran, A., et al., 1992. *In: Profiles in Biotechnology* (T. G. Villa and J. Abalde, Eds.) Servicio de Publicaciones, Universidad de Santiago, Spain. pp. 221–232). One disadvantage of these attempts was the poor potency of aculeacin and papulacandin against *S. cerevisiae*.

In the present work, a more potent echinocandin (L-733, 560) was used as a selective agent, and mutants specifically affected in glucan synthesis were isolated. The first mutant discovered in this screen (strain R560-1C) was used to clone the FKS1 gene. A second mutant identified in the search for L-733,560-resistant strains was found to be echinocandin-resistant and supersensitive to the chitin synthase inhibitor nikkomycin Z. Chitin, like beta-glucan, is a polysaccharide essential for the structural integrity of the fungal cell wall. Nikkomycin Z inhibits cell growth and the in vitro polymerization of chitin. The second mutant was also used to clone the FKS1 gene.

DETAILED DESCRIPTION OF THE INVENTION

DNA molecules encoding proteins involved in biosynthesis of 1,3-beta-D glucan is identified, cloned, expressed and used in in vitro assays to screen for antifungal compounds, including compounds that affect cell wall biosynthesis. The invention includes but is not limited to the purified DNA molecules, assays employing the DNA molecules, proteins encoded by the DNA molecules, cells expressing the DNA molecules and altered forms of the molecule.

The present invention relates to the isolation, characterization, expression, and sequence of a DNA molecule encoding *S. cerevisiae* FK506 sensitivity gene1 (FKS1), which is also known as ETG1, and homologs of FKS1, which include but are not limited to FKS2. The FKS1 gene is obtained from a strain of *S. cerevisiae* which is capable of producing FKS1 protein. Such strains of yeast are well-known in the art and include, but are not limited to, *S. cerevisiae* W303-1A, S288C, GRF88, and YFK007.

The FKS2 gene was found in Southern blots of *S. cerevisiae* genomic DNA as a band hybridizing to a probe consisting of FKS1 DNA.

Although one cannot predict that a particular mutant which is resistant or hypersensitive to these drugs may be isolated, nevertheless, the techniques of isolation of drug hypersensitive or resistant mutants are similar to those used in the isolation of auxotrophic, temperature-sensitive, and UV-sensitive mutants as described in *MYG* (infra). The FKS1 gene or homologs of FKS1 may be isolated from a chromosomal DNA library by a variety of methods including: (1) complementation of a mutation (fks1-1) rendering cells hypersensitive to the immunosuppressant drugs FK506, cyclosporin A, or other calcineurin inhibitors; (2) complementation of a mutation (fks1-2) rendering cells resistant to echinocandins; or (3) complementation of a mutation (fks1-4) rendering cells hypersensitive to nikkomycin Z. (*GYG*, infra, pp. 195–230).

The FKS1 gene or its homologs may be isolated from chromosomal DNA by preparing a library of DNA fragments in a DNA cloning vector and screening individual clones for the presence of FKS1. For example, a library of *S. cerevisiae* genomic DNA from strain GRF88 in the plasmid YCp50 can be obtained from the American Type Culture Collection, 12301 Parklawn Drive, Rockville, Md. 20852, as ATCC 37415.

A plasmid library may be prepared by isolating chromosomal DNA from pure cultures of the microorganisms. Such microorganisms include, but are not limited to, *S. cerevisiae* strains W303-1A, S288C, GRF88, and MY2146 (YFK007). The chromosomal DNA is fragmented, for example, by partial digestion with one or more restriction endonuclease enzymes, such as BamHI, ClaI, BclI, BglII, KpnI, Sau3AI, or XhoI, with Sau3AI being preferred. The digested DNA fragments are separated by size, and the size specific fragments, about 2 to 15 kb in length, are inserted into a cloning vector.

Cloning vector as used herein is defined as a DNA sequence which allows the incorporation of specific experimental DNA, with the combined DNA being introduced into a host cell that can exist in a stable manner and express the protein dictated by the experimental DNA. The foreign DNA combined with the vector DNA constitutes a recombinant DNA molecule which is derived from recombinant technology. Cloning vectors include, but are not limited to, plasmids, bacteriophage, viruses, and cosmids.

The cloning vector is cut with a restriction endonuclease such as SalI, treated with phosphatase and the DNA fragments are ligated with a DNA ligase, with T4 DNA ligase being preferred. The cloning vectors are used to transform host cells competent for the uptake of DNA. Host cells for cloning, DNA processing, and expression include but are not limited to bacteria, yeast, fungi, insect cells and mammalian cells, with the preferred host being *Escherichia coli*. The most preferred hosts are *E. coli* K-12 strains RR1, HB101, JM109, DH11S, or DH5a. When about $5 \times 10^4$ independent genomic DNA fragments are ligated into a cloning vector, this is called a library. A true library is likely to contain a representation of the entire genome. Examples of such libraries are described in Rose et al., (*GYG*, infra).

Competent host cells which take up and stably maintain a recombinant DNA molecule in the transformation procedure can be identified by their ability to grow on LB medium supplemented with a plasmid-selective drug. For plasmid vectors containing the ampicillin resistance gene, ampicillin is the preferred selective drug. To obtain a full representation of the library, transformation mixtures are spread on the surface of many agar plates and incubated under appropriate conditions. Transformant cells can be resuspended from the surface of agar plates in a small volume of liquid medium, with 10 ml of LB medium being preferred. The cell suspension is used to inoculate a larger volume of LB liquid, supplemented with the selective drug, and incubated overnight at 37° C. Plasmid DNA is then extracted from the cells by methods known in the art.

Screens to identify the FKS1 gene or its homologs in the plasmid library can be devised. One strategy requires the use of an echinocandin-resistant mutant of *S. cerevisiae*, such as strain R560-1C (MY2140). Cells are made competent to take up DNA and are then transformed with library DNA. Transformants bearing the FKS1 gene will exhibit a plasmid-dependent decrease in resistance to a selective echinocandin. This expectation is based on information from a genetic analysis of strain R560-1C. When R560-1C is mated to wild-type strains, the heterozygous diploids are intermediate in echinocandin sensitivity compared to the respective parents, suggesting that a single copy of the wild type gene can make the mutant more sensitive to echinocandins.

Aliquots of the transformation mixture are plated on media which are selective for transformants. After incubation to allow growth, colonies are collected, pooled, and stored, preferably by freezing at −80° C. in medium supplemented with 25% glycerol. The titer, defined as the number of colony forming units per milliliter, is determined by methods known in the art.

Identification of transformants that contain the FKS1 gene may be accomplished by plating the library onto agar plates containing plasmid-selective medium such that a countable number of colonies grow on each plate. A portion of each colony is transferred to two agar plates by replica plating: the first plate contains plasmid-selective medium supplemented with a concentration of the selective echinocandin which kills the cells with intermediate sensitivity, and the second contains plasmid-selective medium only. Positive clones are defined as those colonies which grow normally on the plate without echinocandin but grow poorly or not at all on the echinocandin-containing plate.

The echinocandin-sensitive phenotype may be detected by a variety of tests. In one test, cells from a colony are patched directly onto the surface of plates containing different concentrations of the selective echinocandin; cells that grow poorly are scored after two days of incubation.

In a second test, a portion of each colony is transferred by replica plating to an agar plate containing the selective echinocandin at a concentration approximately twice that used in the first test. Positive clones do not grow on these plates.

In a third test, cells from an individual colony are inoculated into plasmid-selective liquid medium and grown to saturation. An aliquot of the saturated culture is used to inoculate fresh liquid medium supplemented with or without the selective echinocandin. After incubation, growth is measured by optical density at a wavelength of 600 nm. Colonies that fail to grow in the presence of echinocandin are scored as positive for increased sensitivity to echinocandin.

In another test, potential clones are assayed in a broth microdilution assay, wherein a range of concentrations of the selective echinocandin are tested. Positive clones are more sensitive to the selective echinocandin than the original resistant mutant.

Tests such as those described above may be used screen a library of genomic DNA so as to identify a recombinant plasmid that contains a functional copy of the FKS1 gene. To determine whether the increase in sensitivity to echinocandin is due to a plasmid-encoded copy of FKS1, positive clones are cured of plasmid DNA and tested for a decrease in sensitivity to echinocandin. If decreased echinocandin resistance is due to the presence of the plasmid, then plasmid loss results in the loss of this phenotype. Echinocandin sensitivity may be measured in a variety of ways, preferably by the broth microdilution assay.

More direct proof that the increase in sensitivity to echinocandin is due to the presence of a plasmid containing the FKS1 gene may be obtained by isolating plasmid DNA from a positive clone. Cells of *E. coli* competent to take up DNA are transformed with the plasmid, and transformants are identified and isolated. Plasmid DNA is isolated from the transformed *E. coli* and then digested with restriction endonucleases to yield fragments of discrete sizes. The size of each fragment can be estimated by conventional methods, such as gel electrophoresis. By digesting the plasmid with a variety of enzymes, a map indicating positions of cleavage is generated; the map is distinct and specific for the cloned fragment. A detailed restriction map is sufficient to identify a particular gene within the genome. Fragments of the cloned gene, generated by digestion with endonucleases, can be purified from agarose gels and ligated into vectors suitable for sequencing by methods known in the art. Such vectors include, but are not limited to pBR322, YEp13, YEp24, pGEM3Zf(+), pGEM5Zf(+), and pGEM7Zf(+), with pGEM3Zf(−), and pGEM7Zf(−) being preferred. Double stranded DNA is prepared from each of the plasmids and used for sequencing.

A second strategy for identifying clones containing the FKS1 gene utilizes its ability to complement an FK506 hypersensitive mutation. An FK506 hypersensitive mutant is transformed with library DNA. Transformants no longer hypersensitive to FK506 are identified by incubating all transformants in the presence of levels of FK506 inhibitory to the growth of the hypersensitive mutant but not to the wild-type strain. Only strains containing DNA comprising the FKS1 gene grow. A similar strategy may be devised using cyclosporin A or any other calcineurin inhibitor to which the mutant is hypersensitive.

A third strategy for identifying clones containing the FKS1 gene utilizes its ability to complement a mutation conferring hypersensitivity to nikkomycin Z. The nikkomycin Z sensitive mutant, such as MS14, is transformed with library DNA. Transformants no longer hypersensitive to nikkomycin Z are identified by incubating all transformants in the presence of levels of nikkomycin Z inhibitory to the growth of the hypersensitive mutant but not to the wild-type strain. Only strains containing DNA containing the FKS1 gene grow.

The FKS2 gene, a homolog of FKS1, may be isolated from chromosomal DNA. Chromosomal DNA is isolated from pure cultures of microorganisms known from Southern hybridization analysis to contain FKS2, using standard methods. The chromosomal DNA is fragmented by digestion with various enzymes. The isolation of FKS2 may be carried out with the use of a probe consisting of a DNA molecule with a region of nucleotide sequence similar to a portion of that of the FKS1 gene. The length of this fragment need only be great enough to confer specificity for FKS2 in a hybridization screen of DNA from an FKS2 containing organism. This fragment may also be longer than the minimum length required to achieve specificity of hybridization. Preferred fragments are the 3.5-kb KpnI FKS1 fragment or the 10-kb PstI-SphI FKS1 fragment.

The FKS1 or FKS2 gene of *S. cerevisiae* may be used to isolate and characterize homologous genes in pathogenic fungi. Southern blot hybridization analyses show that genes closely related to FSK1 and FKS2 exist in the pathogenic fungi. Because the pathogenic fungi, which include but are not limited to strains of *C. neoformans, C. albicans, A. fumigatus, Magnaportha grisea*, and *Ustilago maydis*, have 1,3-beta-D glucan in their cell walls, it is likely that a functional homolog of FKS1 or FKS2 exists in each of these fungi. It is also likely that a functional homolog of FKS1 or FKS2 exists in other organisms that have 1,3-beta-D glucans in their cell walls. Examples of such organisms include, but are not limited to *Pn. carinii*.

FKS1 and FKS2 homologs may be detected by isolating chromosomal DNA from *C. albicans, C. neoformans, A. fumigatus, A. nidulans, M. grisea*, and *U. maydis*. A portion of the chromosomal DNA is cut to completion with a number of restriction enzymes, such as EcoRI, HindIII, EcoRV, ClaI, and XhoI. The digested fragments of DNA are separated by gel electrophoresis. The fragments are then transferred to a solid membrane support such as nitrocellulose or nylon membrane with nylon membrane being the preferred method. The nylon blot is then hybridized with a labeled probe. The probe may be labeled with a radioisotope. The radioisotope of choice is $^{32}$P. A DNA fragment can be radiolabeled either by a nick translation procedure (such as the one described in Rigby et al., (1977) *J. Mol. Biol.*, 113:237–251) or a random priming procedure (such as the one described in Feinberg and Vogelstein (1983) *Anal. Biochem.*, 132:6–13), with the random priming procedure being preferred. The blot is hybridized overnight with a radiolabeled fragment, the 1.4-kb SalI-ClaI FKS1 fragment or the 3.5-kb SalI-ClaI FKS1 fragment or the 1.7-kb PstI-BglII FKS2 fragment being the preferred probes. The following day the blot is washed and then exposed to XAR-5 film and developed. The conditions for washing the blot are such that only genes with a high degree of homology will hybridize with the probe and appear on the autoradiogram. The size and pattern of the digested fragments which hybridize with the probe generate a genomic map. For each organism, the map is sufficient to specifically identify the FKS1 or FKS2 homologs in the chromosome.

Mutations of the FKS1 gene, including, but not limited to, fks1-1 or disruptions or deletions of FKS1, are useful for screening for glucan synthase inhibitors. Such a screen relies on the change in susceptibility of such mutations compared to an FKS1 wild-type strain to glucan synthase inhibitors. Any technique capable of detecting this difference can be used. A zone of inhibition assay on agar plates is particularly useful.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of a modified FKS1 DNA or protein is a compound that possesses a biological activity (either functional or structural) that is substantially similar to the biological activity of the FKS1 DNA or protein. The term "functional derivative" is intended to include the "fragments," "variants," "degenerate variants," "analogs" "homolog" or to "chemical derivatives." The term "fragment" is meant to refer to any polypeptide subset of FKS1 protein. The term "variant" is meant to refer to a molecule substantially similar in structure and function to either the entire protein or to a fragment thereof. A molecule is "substantially similar" to a modified protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire protein or to a fragment thereof.

"Substantial homology" or "substantial similarity", when referring to nucleic acids means that the segments or their complementary strands, when optimally aligned and compared, are identical with appropriate nucleotide insertions or deletions, in at least 75% of the nucleotides. Alternatively, substantial homology exists when the segments will hybridize to a strand or its complement.

The nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods while a chemically synthesized nucleic acid sequence is considered to be substantially purified when purified from its chemical precursors.

Nucleic acid compositions of this invention may be derived from genomic DNA or cDNA, prepared by synthesis or by a combination of techniques.

The natural or synthetic nucleic acids encoding the 1,3-beta-D-glucan synthase subunit of the present invention may be incorporated into expression vectors. Usually the expression vectors incorporating the 1,3-beta-D-glucan synthase subunit will be suitable for replication in a host. Examples of acceptable hosts include, but are not limited to, prokaryotic and eukaryotic cells.

The phrase "recombinant expression system" as used herein means a substantially homogenous culture of suitable host organisms that stably carry a recombinant expression vector. Examples of suitable hosts include, but are not limited to, bacteria, yeast, fungi, insect cells, plant cells and mammalian cells. Generally, cells of the expression system are the progeny of a single ancestral transformed cell.

The cloned 1,3-beta-D-glucan synthase subunit DNA obtained through the methods described herein may be recombinantly expressed by molecular cloning into an expression vector containing a suitable promoter and other appropriate transcription regulatory elements, and transferred into prokaryotic or eukaryotic host cells to produce recombinant 1,3-beta-D-glucan synthase subunit using standard methods.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungi or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant 1,3-beta-D-glucan synthase subunit in mammalian cells. Commercially available mammalian expression vectors which may be suitable for recombinant 1,3-beta-D-glucan synthase subunit expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant 1,3-beta-D-glucan synthase subunit in bacterial cells. Commercially available bacterial expression vectors which may be suitable for recombinant 1,3-beta-D-glucan synthase subunit expression include, but are not limited to pET11a (Novagen), lambda gt11 (Invitrogen), pcDNAII (Invitrogen), pKK223-3 (Pharmacia).

A variety of fungal cell expression vectors may be used to express recombinant 1,3-beta-D-glucan synthase subunit in fungal cells. Commercially available fungal cell expression vectors which may be suitable for recombinant modified 1,3-beta-D-glucan synthase subunit expression include but are not limited to pYES2 (Invitrogen), Pichia expression vector (Invitrogen).

A variety of insect cell expression vectors may be used to express recombinant 1,3-beta-D-glucan synthase subunit in insect cells. Commercially available insect cell expression vectors which may be suitable for recombinant expression of 1,3-beta-D-glucan synthase subunit include but are not limited to pBlue Bac III (Invitrogen), as well as pAcUW1 and pAc5G1 (PharMingen).

An expression vector containing DNA encoding 1,3-beta-D-glucan synthase subunit may be used for expression of modified 1,3-beta-D-glucan synthase subunit in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce 1,3-beta-D-glucan synthase subunit. Identification of recombinant 1,3-beta-D-glucan synthase subunit expressing host cell clones may be done by several means, including but not limited to immunological reactivity with anti-1,3-beta-D-glucan synthase subunit antibodies.

Expression of 1,3-beta-D-glucan synthase subunit DNA may also be performed using in vitro produced synthetic mRNA or native mRNA. Synthetic mRNA or mRNA isolated from 1,3-beta-D-glucan synthase subunit producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

The term "substantial homology", when referring to polypeptides, indicates that the polypeptide or protein in question exhibits at least about 30% homology with the naturally occurring protein in question, usually at least about 65% homology.

The 1,3-beta-D-glucan synthase subunit may be expressed in an appropriate host cell and used to discover compounds that affect 1,3-beta-D-glucan synthase subunit.

The present invention is also directed to methods for screening for compounds which modulate the expression of DNA or RNA encoding 1,3-beta-D-glucan synthase subunit or which modulate the function of 1,3-beta-D-glucan synthase subunit protein. Compounds which modulate these activities may be DNA, RNA, peptides, proteins, or non-proteinaceous organic molecules. Compounds may modulate by increasing or attenuating the expression of DNA or RNA encoding 1,3-beta-D-glucan synthase subunit or the function of 1,3-beta-D-glucan synthase subunit protein. Compounds that modulate the expression of DNA or RNA encoding 1,3-beta-D-glucan synthase subunit or the function of modified 1,3-beta-D-glucan synthase subunit protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing 1,3-beta-D-glucan synthase subunit DNA, antibodies to 1,3-beta-D-glucan synthase subunit, or 1,3-beta-D-glucan synthase subunit protein may be prepared. Such kits are used to detect DNA which hybridizes to 1,3-beta-D-glucan synthase subunit DNA or to detect the presence of 1,3-beta-D-glucan synthase subunit protein or peptide fragments in a sample. Such characterization is useful for a variety of purposes including but not limited to forensic, taxonomic or epidemiological studies.

The DNA molecules, RNA molecules, recombinant protein and antibodies of the present invention may be used to screen and measure levels of 1,3-beta-D-glucan synthase subunit DNA, 1,3-beta-D-glucan synthase subunit RNA or 1,3-beta-D-glucan synthase subunit protein. The recombinant proteins, DNA molecules, RNA molecules and antibodies lend themselves to the formulation of kits suitable for the detection and typing of 1,3-beta-D-glucan synthase subunit. Such a kit would comprise a compartmentalized carrier suitable to hold in close confinement at least one container. The carrier would further comprise reagents such as recombinant 1,3-beta-D-glucan synthase subunit protein or anti-modified 1,3-beta-D-glucan synthase subunit antibodies suitable for detecting 1,3-beta-D-glucan synthase subunit. The carrier may also contain a means for detection such as labeled antigen or enzyme substrates or the like.

Pharmaceutically useful compositions comprising modulators of 1,3-beta-D-glucan synthase subunit activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

Biologically pure samples of *S. cerevisiae* MY2095 (YFK007), *S. cerevisiae* MY2140 (R560-1 C), *S. cerevisiae* MY2147 (YFK532-7C), *S. cerevisiae* MY2148 (YFK798), *S. cerevisiae* MY2256 (YMO148, YFK0978), *S. cerevisiae* MY2257 (YFK1088-23B), *S. cerevisiae* MY2258 (YFK1088-16D), *S. cerevisiae* MY2259 (YFK1087-20B), *S. cerevisiae* MY2260 (YFK1087-20A), and DNA of plasmids pFF119 and pFF334 have been deposited in the permanent collection of the American Type Culture Collection, 12301 Parklawn Drive, Rockville, Md.

The following examples are provided to further define the invention without, however, limiting the invention to the particulars of these examples.

EXAMPLE 1

Recipes for media used in this work include, but are not limited to the following.

a. YEPD medium

| Bacto Yeast Extract | 10 g |
|---|---|
| Bacto-Peptone | 20 g |
| Dextrose | 20 g |
| Distilled Water to 1 liter | |
| Sterilize by autoclaving. | |

For solid YEPD medium, add Bacto-agar to 2% (20 grams) before autoclaving.

b. YPAD medium

| Bacto Yeast Extract | 10 g |
|---|---|
| Bacto-Peptone | 20 g |
| Dextrose | 20 g |
| adenine sulfate | 60–80 mg |
| Distilled Water to 1 liter | |
| Sterilize by autoclaving. | |

For solid YPAD medium, add Bacto-agar to 2% (20 grams) before autoclaving.

c. YPAD/10 mM $CaCl_2$

Dilute 1 part sterile 1M $CaCl_2$ into 100 parts YPAD.

d. YPAG medium

YPAD with glycerol (20 g/liter) in place of dextrose e. SC medium

| Bacto Yeast Nitrogen Base without amino acids | 6.7 g |
|---|---|
| Dextrose | 20 g |
| Complete Amino acid powder | 0.87 g |
| Distilled water to 1 liter | |
| Sterilize by autoclaving. | |

For solid SC medium, add Bacto-agar to 2% (20 grams) before autoclaving.

f. Complete Amino Acid powder

| 0.8 g | Adenine |
|---|---|
| 0.8 | L-Arginine |
| 4.0 | L-Aspartic acid |
| 0.8 | L-Histidine |
| 1.2 | L-Isoleucine |
| 2.4 | L-Leucine |
| 1.2 | L-Lysine |
| 0.8 | L-Methionine |
| 2.0 | L-Phenylalanine |
| 8.0 | L-Threonine |
| 0.8 | L-Tryptophan |
| 1.2 | L-Tyrosine |
| 0.8 | Uracil |
| 6.0 | L-Valine |

Mix with a mortar and pestle.

g. Dropout powders are prepared by omitting one or more components from Complete Amino Acid powder. For example, Trp dropout powder is identical to Complete Amino Acid powder except that L-tryptophan is not added.

h. Solid SC medium containing FK506 is prepared by addition of FK506 to autoclaved SC medium when it had cooled to 50°–52° C. The medium is dispensed into petri dishes and allowed to solidify. Solid SC medium containing L-733,560 is prepared in an analogous fashion.

i. Trp dropout/dextrose medium

| 0.87 g | Trp dropout powder |
|---|---|
| 6.7 g | Yeast Nitrogen Base w/o amino acids |
| 20 g | dextrose |
| 1000 ml | distilled water to volume. |

Adjust to pH 5.8 with 5 M KOH.
Trp dropout plates are made with 20g/1 agar.
Sterilize by autoclaving.

j. Uracil dropout/sorbitol medium

| 0.87 g | Uracil dropout powder |
|---|---|
| 6.7 g | Yeast Nitrogen Base w/o amino acids |
| 20 g | dextrose |
| 182 g | sorbitol |
| 1000 ml | distilled water to volume |

Adjust to pH 5.8 with 5 M KOH.
Sterilize by autoclaving.

k. Uracil dropout/sorbitol agar

Add 20 g/l agar to uracil dropout/sorbitol medium before autoclaving.

l. Uracil dropout/sorbitol soft agar

Add 6 g/l agar to uracil dropout/sorbitol medium before autoclaving.

m. Trp dropout/glycerol

As trp dropout/dextrose but with 20g/l glycerol replacing dextrose.

n. LB medium and LB medium with ampicillin are prepared essentially according to the methods described in Maniatis (infra).

Strains and DNA were isolated and handled by standard procedures (J. Sambrook, E. F. Fritsch, and T. Maniatis, "Molecular Cloning, A Laboratory Manual", second edition, Cold Spring Harbor Laboratory Press, Cold Spring Harbor, N.Y. (1989), referred to as Maniatis; and "Current Protocols in Molecular Biology", F. M. Ausubel et al., editors, John Wiley & Sons, New York (1987), referred to as Current Protocols). Many of the procedures for working with *S. cerevisiae* are described in M. D. Rose, F. Winston, and P. Hieter, "Methods in Yeast Genetics: a Laboratory Course Manual", Cold Spring Harbor Laboratory Press, Cold Spring Harbor, N.Y. (1990), referred to as *MYG*, and in C. Guthrie and G. R. Fink, editors, *Methods in Enzymology*, Volume 194, "Guide to Yeast Genetics and Molecular Biology", Academic Press, Inc., New York (1991), referred to as GYG.

LIST OF STRAINS

| Strain Name | Relevant Properties | MY No. | ATCC |
|---|---|---|---|
| YFK005 | MATalpha FKS1 (wt) | MY2094 | 74059 |
| YFK007 | MATa FKS1 (wt) | MY2095 | 74060 |
| YFK093 | MATa FKS1 fkr3 ($506^R$) | MY2088 | 74055 |
| YFK132 | MATa fks1-1 ($506^s$) | none | |
| YFK531-5A | MATalpha fks1-1 ($506^s$) | none | |
| YFK532-7C | MATa fks1-1 ($506^s$) | MY2147 | |
| YFK532-10B | MATa fks1-1 ($506^s$) | none | |
| YFK798 | MATa fks1-1/YEp-A2B | MY2148 | |
| YFF2409 | MATa fks1-5::HIS3 | none | |
| YFF2411 | MATa fks1-6::HIS3 | none | |
| W303-1A | MATa FKS1 (wt) | MY2141 | |
| W303-1B | MATalpha FKS1 (wt) | none | |
| R560-1C | MATa fks1-2 ($560^R$) | MY2140 | |
| X2180-1A | MATa FKS1 (wt) | MY2136 | |
| MS10 | MATa fks1-3 ($560^R$) | MY2144 | |
| MS14 | MATa fks1-4 ($560^R$, $nik^s$) | MY2145 | |
| D1-22C | MATa fks1-4 ($560^R$, $nik^s$) | none | |

| | | |
|---|---|---|
| GG100-14D | MATalpha FKS1(wt) | none |

PLASMIDS

| Plasmid | Description | Source of cloned DNA |
|---|---|---|
| pFF119 | FKS1 clone in YCp50 | GRF88 |
| pJAM54 | FKS1 clone in YEp24 | YFK093 |
| pMS10 | FKS1 clone in YCp50 | GRF88 |
| pFF250 | 1.7-kb BglII-PstI FKS2 fragment | YFK007 |
| pFF334 | 10-kb EcoRI FKS2 fragment | S288C |

Additional strains and plasmids are shown in the figures.

EXAMPLE 2
Liquid broth microdilution assay

To quantitate the sensitivity of a particular strain of S. cerevisiae to a compound such as FK506, L-733,560, or nikkomycin Z, the following procedure was followed:

Day 1:
Inoculate the strain(s) into 2 ml of SC medium or SC medium substituting a particular dropout powder if selection for an auxotrophic marker (e.g., ura3, his4, etc.) is required. Grow overnight at 30° C. with gentle agitation.

Day 2:
Subculture 20 mcL of each overnight strain into 2 ml of fresh medium; incubate for 4–6 h at 30° C.

Seed a sterile flat bottom 96-well, twelve column microtiter plate with 75 mcL of SD or SD dropout medium in columns 2 through 12. In column 1, seed 150 mcL of the medium.

Dissolve drug of interest at 4× the desired initial concentration. For L-733,560, a 64 mcg/ml solution in sterile SD is prepared. Aliquot 75 mcL of the drug suspension into column 3. Using a multichannel pipettor, transfer 75 mcL from column 3 into column 4, pipet up and down three times to mix, and then transfer 75 mcL from column 4 into column 5. Repeat the serial dilution until column 12 is reached; after mixing, discard 75 mcL to waste.

Label 5 ml sterile tubes with each strain to be tested. Aliquot 2 ml of the appropriate media into each tube. Read the $A_{600}$ of the strains, and dilute the cultures such that the final OD will be 0.0014. For example, if the $A_{600}$ of a strain is 0.7041, subculture 4 mcL into 2 ml of the media.

Inoculate each strain in a given row by adding 75 mcL of the inoculum into columns 2 to 12. Do not add cells to column 1, as column 1 is the blank. Column 2 serves as the no-drug or 100% growth control. The plate is then incubated overnight at 30° C. without shaking.

Day 3:
After approximately 24 hours of incubation, gently agitate the plate to resuspend the cells and read the absorbance at 600 nm wavelength. The % control growth for any given well can be calculated by dividing the absorbance value for that well by the value from column 2 in the same row. If this is done for each column, the data can be plotted as "Percent control growth" vs. "Drug concentration". The resulting dose-response curve can be used to compare the drug sensitivities of various strains.

EXAMPLE 3
Isolation of YFK132, an fks1-1 mutant

S. cerevisiae YFK132 was isolated from S. cerevisiae strain YFK007 (wild-type; MY2095; ATCC 74060) by standard ethylmethane-sulfonate (EMS) mutagenesis procedures (Sherman et al., 1986 in "Laboratory course manual for methods in yeast genetics", Cold Spring Harbor Press). Parental strain YFK007 is sensitive to about 50 mcg/ml of FK506 and is insensitive to 100 mcg/ml CsA. Mutant strain YFK132 is hypersensitive to FK506.

YFK007 was grown overnight in 25 ml of YEPD at 30° C. The cells were harvested by centrifugation, and resuspended in 10 ml of 0.05M potassium phosphate buffer (pH 7) at a density of $3\times10^8$ cells/ml. The cell suspension was diluted to $1.24\times10^8$ cells/ml and divided into two samples To one sample, 0.588 ml of EMS (Sigma Cat. No. M0880) was added. The same volume of distilled water was added to the second sample as a control. Treated cell suspensions were incubated at 25° C. At various times, samples were removed and added to 8 ml of 5% sodium thiosulfate to quench the mutagenesis. Quenched cells were diluted in water, plated on YEPD agar and incubated at 25° C. Cells from EMS-treated and untreated cultures were spread on YEPD plates at various dilutions, and colonies were counted to determine cell viability after the mutagenesis.

YEPD plates containing mutagenized colonies were replica plated onto SC agar containing 0, 1 or 10 mcg/ml of FK506, and incubated at 25° C. Approximately 1,200 colonies were screened. Three cultures that failed to grow on SC medium+FK506 were identified and analyzed further.

One of these cultures, designated YFK132, exhibited an FK506-hypersensitive phenotype (sensitive to 0.1 mcg/ml FK506), was sensitive to 10 mcg/ml CsA, and was slow growing.

EXAMPLE 4
Backcrossing YFK132, an fks1- 1 mutant

To determine whether the phenotypes of YFK132 were the result of a single mutation, tetrad analyses were performed on crosses between mutant and wild-type strains.

YFK132 was crossed to the wild type strain YFK005 and a meiotic segregant from the resulting diploid backcrossed to YFK007 two times to generate strains YFK531-5A, YFK532-7C, and YFK532-10B. The FK506 hypersensitive and slow growth phenotypes of YFK132 cosegregated in all crosses, indicating that these phenotypes resulted from a mutation in a single gene. YFK132 is an fks1-1 mutant of YFK007.

EXAMPLE 5
Testing the echinocandin sensitivity of YFK132

The sensitivity of YFK132 to the echinocandin L-688,786 was determined in a disc-diffusion assay.

YFK132 and its parent (YFK007) were grown in 2.5 ml of liquid SC medium and diluted to $6.25\times10^7$ cells/ml with distilled water. Molten SC medium containing 2% agar (130 ml) was inoculated with 4 ml of diluted culture and immediately poured into 245×245 mm bioassay plates. After the medium had solidified, sterile filter discs containing FK506 (1, 10 and 50 mcg) or L-688,786 (1, 10 and 50 mcg) were placed on the surface of the medium and incubated at 28° C. After 18 hours, zones of growth inhibition were measured.

As shown in the following table, YFK132 is more sensitive to L-688,786 than its parent strain (YFK007).

| Amount of L-688,786/disc | Zone Sizes (mm) | |
|---|---|---|
| (micrograms) | YFK007 | YFK132 |
| 1 | 0 | 8.4 |
| 10 | 8.7 | 16.8 |
| 50 | 8.7 | 18.0 |

EXAMPLE 6
Cloning of FKS1 by complementation of fks1-1

A. General approach

The 1,3-beta-D-glucan synthase gene (FKS1) was cloned by complementation of the FK506 hypersensitive phenotype of YFK532-10B (MATa, ade2-101, his3-Δ200, leu2-Δ1, lys2-801, trp1-Δ1, ura3-52, fks1-1). The general approach to cloning genes by complementation of mutant phenotypes is outlined by M. D. Rose and J. R. Broach (in GYG, pp. 195–230).

Library plasmid DNA was obtained from *E. coli* ATCC 37415. This library was created by M. D. Rose, et al., (*Gene*, 60, 237–243, 1987), by inserting 10- to 20-kb Sau3AI partial-digest fragments of yeast genomic DNA from strain GRF88 into the yeast shuttle vector YCp50.

B. Preparation of electroporatable cells

Cells of YFK532-10B were prepared for transformation by electroporation, essentially as described by D. M. Becker and L. Guarente, (in Guthrie and Fink, supra, pp. 182–187). Recipient cells were grown on agar plates containing YPAG medium supplemented with 0.004% adenine sulfate. Cells from a fully grown patch (1 mm×5 mm) were inoculated into 50 ml of YPAD-25C medium (YPAD supplemented with 25 mM $CaCl_2$) in a 250 ml Erlenmeyer flask and incubated at 30° C. on a rotary shaker (225 rpm, 2"throw). The culture was grown to an optical density of 1.3 at 600 nm and transferred to a sterile 50-ml disposable polypropylene centrifuge tube. Cells were harvested by centrifugation at 3500 rpm for 5 min at 4° C. in a Sorvall RT6000 refrigerated centrifuge. The cell pellet was resuspended with 25 ml ice-cold sterile water by vortexing at full speed, harvested by centrifugation and washed again with 25 ml ice-cold sterile water. The cell pellet was resuspended with 10 ml ice-cold sterile 1M sorbitol. The washed cell suspension was transferred to a sterile 10-ml disposable polypropylene centrifuge tube, and the cells were harvested by centrifugation at 3500 rpm for 10 min at 4° C. The cell pellet was resuspended with 0.1 ml ice-cold sterile 1M sorbitol.

C. Electroporation of recipient cells

A portion (50 mcL) of the washed cell suspension was transferred to a sterile microfuge tube. An aliquot (1 mcL containing ca. 500 ng) of library plasmid DNA (Bank A) was added to the cells, mixed gently, and incubated on ice for about 5 min. The cell suspension was transferred to a cold 0.2-cm sterile electroporation cuvet and pulsed at 1.5 kV, 25 uF, 200 ohm (BioRad Gene Pulser with Pulse Controller). Immediately 3 ml ice-cold sterile 1M sorbitol was added and mixed gently.

Fifteen aliquots (0.2 ml) were transferred to sterile culture tubes. Uracil drop-out/sorbitol soft agar (3.5 ml) containing 1M sorbitol in soft (0.6%) agar at 46° C. was added to each tube to form a mixture, and each mixture poured over a 2% agar plate made with the same sorbitol-containing medium, giving a total of fifteen plates. The procedure was repeated until 210 plates were obtained.

The plates were incubated at 30° C. After 24 hr each plate was overlayered with 3 ml of uracil drop-out/sorbitol soft agar containing 1 mcg/ml FK506 (a 5 mg/ml stock solution of FK506 in ethanol was added to autoclaved medium that had been cooled to 55° C.). The plates were incubated at 30° C. for 6 more days. Cells from transformant colonies were purified by streaking for single colonies on agar plates containing uracil drop-out medium supplemented with 0.1 mcg/ml FK506.

D. Isolation of plasmid pFF119

Colonies of the purified transformants were inoculated into 1.5 ml uracil dropout medium in 16-mm culture tubes and incubated in a tube roller at 30° C. for two days. Plasmid DNA was prepared essentially as described by J. N. Strathem and D. R. Higgins (in Guthrie and Fink, supra, pp. 319–329) according to Method 1 and transformed into competent *E. coli* strain DH11S (Bethesda Research Laboratories). Plasmid DNA was prepared from ampicillin-resistant *E. coli* using the QIAGEN-tip 500 procedure (QIAGEN Inc., Chatsworth, Calif.). The resulting plasmid was designated pFF119.

The ability of pFF119 to complement the fks1-1 mutation was confirmed by spontaneous curing of the plasmid in the original transformant. Curing restored the FK506 hypersensitive phenotype. Retransformation with pFF119 restored FK506 resistance.

E. Localization of the fks1-1 Complementing DNA pFF119 was digested with various combinations of restriction endonucleases and analyzed by agarose gel electrophoresis. The results showed that pFF119 contained an insert of about 15 kb of DNA.

An 11-kb SphI fragment from within the 15-kb region was transferred to the SphI site of plasmid YCplac33 [R. D. Gietz and A. Sugino, *Gene*, 74:527–534 (1988)] in both orientations giving plasmids pFF133 and pFF135. These plasmids were also capable of complementing the FK506 hypersensitive phenotype of the fks1-1 mutation.

Nested subclones of the cloned DNA were created by linearizing pFF133 and pFF135 with BamHI, digesting partially with Sau3AI, and recircularizing the molecules with DNA ligase. Only two of the subclones (pFF172 and pFF173) were capable of complementing fks1-1. The complementing DNA was thus localized to a region with a minimum of 6.0 kb and a maximum 7.8 kb of DNA, between the first SphI site and the second BglII site.

F. Identification of the fks1-1 Complementing DNA as FKS1

An insertion-deletion allele of the fks1-1 complementing DNA was created in the following manner. The 8.8-kb SphI-PstI fragment of pFF133 was inserted between the SphI and PstI sites of the polylinker of the *E. coli* vector pGEM-5Zf(+) (Promega, Madison, Wis.) giving plasmid pFF174. The 1.3-kb BamHI-XhoI HIS3 fragment from plasmid pJJ215 (J. S. Jones and L. Prakash, *Yeast*, 6:363–366 (1990)) was inserted by blunt-end ligation (see *Current Protocols*, p. 3.5.10) between the two KpnI sites of plasmid pFF174 giving plasmids pFF186 (sense orientation) and pFF187 (antisense orientation). The 6.6-kb insertion-deletion fragments were excised by digestion with SstI+SphI and purified by agarose gel electrophoresis. The insertion-deletion mutation was created by one-step gene replacement (see R. Rothstein, *GYG*, pp. 281–301). This disruption was confirmed by Southern blot hybridization analysis of genomic DNA digested with PstI and probed with the 8.8-kb SphI-PstI fragment from plasmid pFF174. The undisrupted parent gives a single 9.8-kb genomic fragment which hybridizes with the probe. A disruption mutant in which HIS3 is inserted in the sense orientation, for example YFF2409, gives 3.9- and 3.7-kb fragments, while an antisense disruption mutant, for example YFF2411, gives 4.9- and 2.7-kb fragments. A haploid strain with the insertion-deletion allele has phenotypes essentially identical to an fks1-1 mutant: it is slow-growing, hypersensitive to FK506, and hypersensitive to L-733,560. Diploids created by crossing insertion-deletion haploids with fks1-1 haploids are slow-growing and hypersensitive to FK506 showing that the insertion-deletion mutation fails to complement the fks1-1 mutation.

These results prove that the two alleles are in the same gene and that pFF119 carries the FKS1 gene. The insertion-deletion mutations are therefore referred to as fks1-5::HIS3 and fks1-6::HIS3.

EXAMPLE 7
Other Strains of *S. cerevisiae* Possess Variants of FKS1

Southern hybridization analysis of genomic DNA isolated from various strains of *S. cerevisiae* and digested with different restriction enzymes revealed that some strains have a variant of FKS1 which has a restriction map which differs slightly from that for the gene in GRF88. Strains with FKS1 genes with restriction maps like that for GRF88 (G. R. Fink) include SC347 (J. Hopper), W303-1B (R. Rothstein), S288C (R. K. Mortirner), and A384A (L. Hartwell). Strains with ones like that for YFK007 include YPH1 (Phil Hieter), YFK005, YFK093, DS94 (E. Craig), and DS95 (E. Craig).

EXAMPLE 8
Isolation of FKS2 by cross-hybridization with FKS1 DNA.

A 2.5-kb PstI genomic fragment crosshybridizing with the FKS1 probe was detected in Southern blots of genomic DNA from *S. cerevisiae*. This fragment was not derived from the FKS1 region of the genome. When genomic DNA was digested with BglII+PstI the fragment was 1.7 kb in size. Genomic DNA was isolated from strain YFK007, digested with BglII+PstI, and fractionated on an agarose gel. The region of the gel containing the crosshybridizing fragment was excised, and DNA was isolated using the QIAEX extraction procedure (QIAGEN Inc.). The extracted DNA was inserted between sites for BamHI and PstI in the polylinker of the plasmid pGEM-3Zf(+), and the ligated DNA was transformed into strain DH11S (Bethesda Research Laboratories). Ampicillin resistant transformants were screened for the presence of the crosshybridizing DNA by colony hybridization (Maniatis, supra). Plasmid DNA was isolated from positive clones and digested with KpnI+PstI. KpnI was used in place of BglII, since the BglII site was lost during the ligation with the vector. The presence of a 1.7-kb fragment crosshybridizing with the FKS1 probe was confirmed by Southern blot hybridization analysis. The resulting plasmid is called pFF250.

The 1.7-kb fragment was used to screen a lambda library (Stratagene, cat. no. 951901) of yeast genomic DNA from strain S288C by plaque hybridization (Maniatis, supra). DNA was isolated from positive clones, digested with various restriction enzymes, and analyzed for hybridizing fragments by Southern blot hybridization. A 10-kb EcoRI fragment carrying the hybridizing region was cloned into the EcoRI site of pBluescript II KS(+) (Stratagene) in both orientations giving plasmids pFF334 and pFF336.

An insertion-deletion mutation of the 1.7-kb BglII-PstI DNA was created by inserting the 0.8-kb PstI TRP1 fragment from pJJ246 (J. S. Jones and L. Prakash, *Yeast*, 6:363–366 (1990)) between the AflII and BbsI sites by blunt end ligation. The 2.1-kb disruption fragment was excised with PstI+KpnI. The insertion-deletion mutation was inserted by one-step gene replacement into the chromosome of a heterozygous fks1-5::HIS3/+ and homozygous trp1/trp1 diploid. Genomic DNA from Trp$^+$ transformants was digested with BglII+HindIII+PstI. The undisrupted locus gives a 1.7-kb hybridizing fragment, while the insertion-deletion mutation gives 1.4- and 0.7-kb fragments.

A transformant heterozygous at the locus of the insertion-deletion mutation was sporulated and dissected on YPAD. Trp$^+$ His$^-$ spores were viable. However, Trp$^+$ His$^+$ spores were inviable. The insertion-deletion mutation thus defines a new locus FKS2, and the insertion-deletion mutation of this locus (fks2::TRP1) is synthetically lethal with fks1-5::HIS3. These results are interpreted to mean that the products of FKS1 and FKS2 have overlapping functions and that when the function of each is inactivated, either through genetic disruption or by inhibition of their gene products with L-733,560, cells are not viable.

EXAMPLE 9
Construction of a plasmid DNA library containing the FKS1 gene

A genomic DNA library containing the FKS1 gene was constructed in the plasmid YEp24 by standard methods (Rose and Broach, 1991, *Methods in Enzymology*, 194:195–230).

High molecular weight genomic DNA was prepared from yeast strain YFK093 (MY2088, ATCC 74055), partially digested with Sau3AI and size-fractionated over a sucrose gradient. A fraction of Sau3AI-digested DNA ranging from 10–15 kb was partially-filled in with Klenow fragment of DNA polymerase I using dATP and dGTP.

The multicopy vector (YEp24) was digested with SalI, and partially-filled in with Kienow fragment of DNA polymerase I using dCTP and dTTP. After the fill-in reactions, the DNAs were phenol extracted once and ethanol precipitated. Partially-filled in genomic and vector DNAs were ligated and transformed into HB101 cells by selecting for ampicillin resistance.

Two independent libraries were generated by pooling clones generated by separate transformations. One library contained ca. 34,100 transformants while the second library contained ca. 15,000 transformants. The frequency of recombinants in these libraries was judged to be ~95% by restriction enzyme digestions.

EXAMPLE 10
Isolation of R560-1C, a mutant of *S. cerevisiae* resistant to L-733,560

Strain W303-1A was transformed by the spheroplast method (*MYG*) with yeast genomic libraries obtained from D. Botstein (1982. *Cell*, 28:145–154). Transformants selected on uracil dropout medium were pooled and stored at −80° C. in 20% glycerol. After determining the titer (colony forming units(CFU)/ml), aliquots of the stocks were spread at ≅5×10$^3$ CFU per plate onto uracil dropout medium containing the semisynthetic echinocandin L-733,560 at 0.5 mcg/ml or 1.25 mcg/ml. This concentration of L-733,560 is sufficient to select for resistant clones. Twenty-seven drug resistant colonies were isolated. The resistance phenotype of these clones was quantitated in a liquid MIC assay. Briefly, L-733,560 was serially diluted across the wells of a sterile microtiter plate such that the concentration in each row ranged from 16 to 0.03 mcg/ml in 2-fold increments after an equal volume of a cell suspension in liquid uracil dropout medium was added. After 24 h at 30° C., plates were read in a spectrophotometer at a wavelength of 600 nm, and the percent of control growth in each well (relative to a no-drug control well) was calculated. The resulting dose-response curve was used to determine the resistance relative to the parent strain. One clone was 16–32-fold more resistant than the parent strain; the others were 2 to 4-fold more resistant. The most resistant clone, R560-1, was characterized further.

Because this strain was isolated as a transformant from the genomic library, it was expected that resistance would be due to the gene residing on the plasmid contained in R560-1. To test this, the strain was cured of the plasmid by selection with the 5-fluoroorotic acid method (*MYG*). Loss of the plasmid and its resident URA3 gene renders cells resistant to 5-fluoroorotic acid, and the uracil auxotrophy was confirmed by the absence of growth on uracil dropout medium. Surprisingly, the drug resistance of the cured derivative (R560-1C) was unchanged by the loss of the plasmid. This results suggests that R560-1C is a spontaneous echinocandin-resistant mutant of strain W303-1A. R560-1C was challenged with other beta-glucan synthase inhibitors such as L-688,786, L-646,991 (cilofungin), and L-687,781 (papulacandin) in a liquid MIC assay. The results illustrate that the resistance phenotype is not specific to L-733,560 but also includes structurally related and unrelated inhibitors of 1,3-beta-D beta-glucan synthesis. To determine whether the phenotypes of R560-1C were the result of a single mutation, tetrad analyses were performed on diploids formed by crossing mutant and wild-type strains. R560-1C was mated to the wild type strain W303-1B, sporulated, dissected, and the sensitivity to L-733,560 quantitated by liquid MIC assay. Drug resistance segregated 2:2 in these tetrads, proving that resistance is due to a mutation in a single gene. This mutation is called fks1-2.

EXAMPLE 11

Cloning the FKS1 gene by complementation of the fks1-2 mutation in R560-1C

Using information from the genetic analysis of R560-1C, a screen was devised to clone the wild type allele of fks1-2. When R560-1C was mated to the wild type strain W303-1B, the resulting heterozygous diploids were intermediate in sensitivity to L-733,560, suggesting that a single copy of the wild type FKS1 gene would make the mutant more sensitive to echinocandins. By cloning a library of S. cerevisiae DNA into R560-1C, transformants could be screened for plasmid-dependent intermediate sensitivity to L-733,560. Broth microdilution and replica plating methods discriminated between heterozygous diploids and R560-1C at 4 mcg/ml L-733,560.

The S. cerevisiae total genomic library of Example 9 was transformed into S. cerevisiae R560-1C by the spheroplast method (Maniatis, supra). Ura+ clones were selected on uracil dropout medium, scraped from the plates, pooled, and stored frozen at −80° C. in 20% glycerol. Aliquots of the library were plated onto uracil dropout medium at 200–300 CFU/plate. After incubation at 30° C. for 24 h, the colonies on each plate were replica plated to: 1) uracil dropout medium plates supplemented with 4 mcg/ml L-733,560; and 2) uracil dropout medium plates. Putative clones were identified by poor growth on the drug supplemented plate and strong growth on the drug-free plate. Three additional tests were used to establish which potential clones were truly drug sensitive. In one test, putative clones were inoculated into liquid uracil dropout medium in mirotiter plates and grown for 24 h at 30° C. Using a Dynatech inoculator, cells from each well were inoculated into: 1) uracil dropout medium supplemented with 4 mcg/ml L-733,560; and 2) uracil dropout medium. Growth was quantitated spectrophotometrically, and poor growth in drug supplemented medium was scored as positive. In a second test for drug resistance, colonies were patched directly to uracil dropout medium plates supplemented with 4 mcg/ml L-733, 560 and scored for poor growth after 24 h at 30° C. In the third assay, putative clones were patched to uracil dropout medium plates, grown for 24 h at 30° C., then replica plated to uracil dropout medium supplemented with 10mcg/ml L-733,560. Growth was scored after 24 h at 30° C.

Nine putative clones were positive in all assays for intermediate drug sensitivity. One strain (S277) was nearly as sensitive to L-733,560 as the wild type strain. To quantitate the drug sensitivity of clone S277, a liquid MIC assay was performed. The drug-sensitive clone (S277) was significantly more sensitive than the mutant (R560-1C), and nearly as sensitive as the wild type strain (W303-1A). To verify that the intermediate drug sensitivity of S277 was due to the cloned gene it contained, the plasmid was cured by the 5-fluoroorotic acid method. An MIC assay revealed that loss of the plasmid resulted in a reversal of the intermediate sensitivity to L-733,560, such that the plasmid-cured clone was as resistant to drug as the original resistant mutant (R560-1C). Finally, retransforming R560-1C with plasmid DNA isolated from S277 yielded Ura+ clones which were identical to the original drug sensitive clone (S277) in their intermediate sensitivity to L-733,560.

Plasmid DNA was isolated from the drug sensitive clone (S277) and transformed into E. coli by methods described in Maniatis. Two plasmids with different size inserts were isolated and characterized by restriction endonuclease mapping; one (pJAM53) had a 14 kb insert, and the second (pJAM54) had an 8 kb insert. Restriction mapping illustrated that the insert in pJAM54 was entirely contained within the 14 kb fragment of pJAM53. Both plasmids conferred intermediate sensitivity to L-733,560, as judged by liquid MIC assays, when they were introduced by transformation into strain R560-1C.

EXAMPLE 12

Overexpression of calcineurin in the fks1-1 mutant

Individual phage clones containing the calcineurin genes were identified from a yeast genomic DNA library of strain S288C in lambda-DASH (Stratagene, cat. no. 943901) by hybridization to probes synthesized from yeast genomic DNA by PCR (Foor et al., Nature, 360:682–684 (1992)). The CNA2 and CNB1 genes were mapped to 4.3-kb BglII and 1.3-kb EcoRV DNA fragments within isolated phage clones, respectively. The CNB1 fragment was inserted into the SmaI site of pBluescript II KS(+) in the lacZ orientation and transferred as a BamHI-EcoRI fragment to the TRP1-selectable multicopy yeast shuttle vector YEplac112 (Gietz & Sugino, 1988, supra), giving plasmid YEp-B. The CNA2 fragment was inserted into the BamHI site of YEp-B giving YEp-A2-B. This plasmid was transformed by electroporation into the fks1-1 strain YFK531-5A giving strain YFK798.

EXAMPLE 13

A. Use of YFK532-7C, an fks1-1 mutant strain, for screening for glucan synthase inhibitors Strain YFK532-7C, an fks1-1 mutant, is at least a thousand fold more sensitive to FK506 and CsA (known calcineurin inhibitors) than is strain YFK007, an FKS1 wild-type strain. YFK007 and YFK532-7C can be used to screen for calcineurin inhibitors.

Strain YFK532-7C is also 8–10 fold more sensitive than strain YFK007 to glucan synthase inhibitors of both the echinocandin and papulacandin classes. Therefore, these strains can be used to screen for glucan synthase inhibitors.

Counter screening strains were devised for identifying calcineurin inhibitors. Overexpression of yeast calcineurin in the fks1-1 mutant (strain YFK798) constitutes the most general of these. Any inhibitor targetting calcineurin shows either zone diameter reduction or a decrease in zone clarity (sometimes both). Glucan synthase inhibitors show neither effect and thus can be distinguished from calcineurin inhibitors.

For positively identifying glucan synthase inhibitors, screening with strain R560-1C and its parent W303-1A was instituted in a manner identical to that described for calcineurin inhibitors. Complete loss of a zone, or marked reduction in size, on R560-1C versus W303-1A indicates a glucan synthase inhibitor. No zones are seen with calcineurin inhibitors using this pair of strains.

B. Description of the laboratory procedure

The initial screen consists of a two-plate differential zone size determination comparing the sensitivity of fks1-1 yeast mutant (YFK532-7C, hypersensitive to FK506 and CsA) to that of the FKS1 wild-type strain (YFK007). Each strain is grown at 28°–30° C. in YPAD/10 mM $CaCl_2$ medium with shaking at 220 rpm (to mid or late log phase). The cultures are diluted 1:10 with water, and the OD values of the dilutions are measured at 600 nm (against a blank of YPAD/10 mM $CaCl_2$ similarly diluted 1:10 in water). The OD value is multiplied by 10 to estimate the OD of the culture. Portions (100 ml) of YPAD/10 mM $CaCl_2$ medium containing 1.5% agar, equilibrated at 45° C. in a water bath, are seeded with culture such that the final cell density in the agar would have an OD value of 0.015 (i.e., $3 \times 10^6$ cfu/ml; a sample calculation is provided below). The seeded agar is poured into 500 $cm^2$ Nunc plates. Once the agar plates have solidified, 10 mcL aliquots of samples containing test compounds, such as fermentation extracts, are dissolved in water, 100% methanol or ethanol, or up to 50% DMSO and are placed on each member of the two-plate set in 11 by 8 arrays.

The plates are incubated for 48 h at 28°–30° C. Diameters of the zones are read to the outermost edge and recorded in mm. The clarity of the zone is reported as clear (no designation), hazy (h), or very hazy (vh). Very hazy zones are best seen by viewing the plate under an elevated light placed between the assay dish and a dark wall.

STANDARDS

1. L-679,934 (FK506) Dissolve in methanol.
2. L-644,588 (cyclosporin A) (Sandimmune) is sold in a Cremaphor vehicle at a concentration of 100 mg/ml. Dilutions may be made in 50% methanol or 50% ethanol with vigorous mixing at each step. The cremaphor remains very cloudy in these dilutions but the cyclosporin is bioavailable.
3. L-733,560 Dissolve in methanol.
4. L-687,781 (dihydropapulacandin) Dissolve in methanol.
5. L-636,947 (aculeacin) Dissolve in methanol.
Store all standards at –20° C.
Sample calculation of inoculum dilution Overnight yeast cultures will have OD values ranging from 7 to 10 (i.e., 0.7 to 1.0 for 1:10 dilutions). A culture with an OD of 8.9 is diluted 1:593 to give a suspension with an OD of 0.015. Therefore, a 100-ml portion of YPAD/10 mM $CaCl_2$ agar would be inoculated with 169 ml of culture.

|  | Primary Screen Zone size (mm) | | |
|---|---|---|---|
| Controls | YFK007 (wild type) | YFK532-7C (fks1-1) | YFK798 (fks1-1 + CN) |
| 20 ng FK506 | none | 15–17 | 13 vh edges |
| 10 mcg CsA | none | 18–20 | 15 vh edges |
| 10 mcg L733,560 | 16–18 | 22–24 | 22–24 |
| 20 mcg aculeacin | 22–24 | 27–30 | 27–30 |
| 20 mcg papulacandin | 20–22 | 26–28 | 26–28 |

|  | Secondary Screen Zone size (mm) | |
|---|---|---|
| Controls | W303-1A | R560-1C |
| 20 ng FK506 | none | none |
| 10 mcg CsA | none | none |
| 10 mcg L733,560 | 16–18 | 8 vh |
| 20 mcg aculeacin | 18–22 | 17–20 |
| 20 mcg papulacandin | 15–18 | 14–16 |

Results in primary screen

A zone at least 2 mm larger on YFK532-7C than YFK007 indicates the presence of either a calcineurin or glucan synthase inhibitor.

A zone that is reduced or hazier on YFK798 compared that seen on YFK532-7C indicates that the unknown is a calcineurin inhibitor.

A zone that is reduced on R560-1C compared with W303-1A indicates that a glucan synthase inhibitor is present.

EXAMPLE 14

Glucan Synthase Assay

Cell free extracts were prepared from mutant and wild type cells grown to logarithmic phase as previously described (Kang and Cabib, PNAS, 83:5808–5812, 1986). After homogenization with glass beads, the unbroken cells and debris were removed by a low speed centrifugation (1,000×g for 5 min). The supernatant fluids were centrifuged at 100,000×g for 60 min and the pellets were washed with 2.5 ml (per gram of wet cells) of buffer containing 0.05M potassium phosphate (pH 7.5), 0.5 mM DTT, and 1.0 mM PMSF. The washed pellet was resuspended in the same buffer containing 5% glycerol. This served as the microsomal membranes source containing both chitin and glucan synthase enzymatic activities. The standard 1,3-beta-D glucan synthase reaction was initiated by mixing 35 mcg protein in cocktail I, which included TEK buffer (125 mM Tris chloride, pH 7.5, 31 mM KF, and 1 mM EDTA), 25% PBS, pH 7.0, 3.31 mcM GTP-gamma-S, and 0.25% BSA in a total volume of 69 mcL, with cocktail II, which included 4 units alpha-amylase, 25 mcg UDP-glucose, and 1 microCi UDP-$^3$H-glucose, in a total volume of 11 mcL. Following 150 minutes of incubation at 30° C., the incorporation of UDP-$^{14}$C-glucose into glucan was measured after precipitation with trichloroacetic acid.

EXAMPLE 15

Chitin synthase assay 125 mcg of the above extracts were trypsin activated and mixed with an equal volume (50 mcL) chitin synthase reaction cocktail, which included 0.5M Tris, pH 7.5, 40 mM MgCl, 320 microM GlcNAc, $^{14}$C-UDP-GlcNAc substrate mix, and 0.8% digitonin. After 30 minutes of incubation at 30° C., the incorporated $^{14}$C-glucose was precipitated with 10% trichloroacetic acid, collected onto Whatman glass microfiber GF/A disks and counted.

EXAMPLE 16

Isolation of the echinocandin-resistant mutants MS10 (MY2144) and MS14 (MY2145)

MS10 and MS14, were isolated as echinocandin resistant mutants in two different experiments.

In the first experiment, approximately 45 mcg (40 mcL of 1.12 mcg/ml solution) of the semisynthetic echinocandin L-733,560 was spread over the surface of each of four plates containing YNBD solid medium (YNBD medium is the same as the SC medium but lacking amino acids). The solution was allowed to air-dry before $1 \times 10^6$ cells of the S. cerevisiae strain X2180-1A freshly grown overnight on YNBD broth was plated onto each plate. Following growth at 28° C. for four days, three colonies capable of growth in presence of L-733,560 were picked as echinocandin-resistant mutants. One of those mutants was designated MS14.

The second experiment was performed as described above with the following modifications: The concentration of L-733,560 used was approximately 22.5 mcg/plate. The inhibitor was added to 20 ml of YNBD media that had been melted and then cooled to 50° C. Four plates prepared; then $1 \times 10^6$ cells of *S. cerevisiae* strain X2180-1A was spread over the surface of each plate. Following growth at 28° C. for 4 days, 12 resistant colonies were isolated. One of those mutants was designated MS 10.

Based on these experiments the mutation frequency of the mutant MS14 is $1.3 \times 10^{-6}$, while the mutation frequency of the mutant MS10 is $3 \times 10^{-6}$.

EXAMPLE 17
Characterization of MS10 and MS14 Mutants

MS10 and MS14 did not exhibit multiple drug resistance when tested against a panel of more than 30 inhibitors affecting cell wall, membrane, sterol, and protein synthesis. Cells of the yeast strains MY2144 and MY2145 carrying the respective MS10 and MS14 mutations were grown overnight in YPAD and SC media. From the overnight cultures, cells were diluted 1:10 in the same media and allowed to further grow for 4–6 hrs. The drug resistance/sensitivity tests were conducted by the disc diffusion assay on plates containing 20 ml of solid YPAD or SC media and $3 \times 10^6$ cells. The cells were added to premelted media that was cooled to 50° C. before pouring onto plates. Sterile filter discs containing different drugs were placed on the surface of the plates followed by incubation at 28° C. for 1–2 days. Sizes of the zones of growth inhibition were measured as an indication of relative drug resistance/sensitivity. The MS14 mutant is supersensitive to the chitin synthesis inhibitor nikkomycin Z and resistant to the echinocandin L-733-560.

The dominance/recessiveness relationships of the mutations in MS10 and MS14 were determined by comparing the drug resistance phenotype of haploid and diploid cells using both the disc diffusion and the broth microdilution assays. The results of those assays show that the nikkomycin Z-supersensitivity of the MS14 cells is recessive while the echinocandin-resistance phenotype is semi-dominant. In contrast, the echinocandin-resistance phenotype of the MS10 cells is dominant.

The data in the following table are the minimum concentration of the various drugs required to inhibit the growth of each the mutants and their parent X2180-1A.

| | MIC | | |
|---|---|---|---|
| Strain | L-733,560 (uM) | Papulacandin (mcg/ml) | Nikkomycin Z (mcg/ml) |
| X2180-1A | 0.045 | 5.5 | >100 |
| MY2144 (fks 1-3) | 0.75 | 15 | >100 |
| MY2145 | 2.0 | 5.5 | 0.2 |

EXAMPLE 18
Mutant plucan and chitin synthesis enzymatic activities

Crude enzyme preparations associated with cell membranes were tested for glucan and chitin synthesis activities. The sensitivity of the mutant 1,3-beta-D glucan synthase to L-733,560 and papulacandin was tested along with the sensitivity of the chitin synthases to nikkomycin Z.

Results of these experiments revealed that both MS10 and MS14 have normal levels of 1,3-beta-D glucan synthase that are highly resistant to L-733,560 but only marginally resistant to papulacandin. The chitin synthase is not affected in its sensitivity to nikkomycin Z. The data in the following table show the $IC_{50}$s for the glucan synthase inhibitors (L-733,560 and papulacandin) and the chitin synthase inhibitor (nikkomycin Z) in 1,3-beta-D glucan synthase and chitin synthase assays, respectively. Equal amounts of membrane proteins were used to prime each reaction.

| | $IC_{50}$ | | |
|---|---|---|---|
| Strain | L-733,560 (uM) | Papulacandin (mcg/ml) | Nikkomycin Z (mcg/ml) |
| X2180-1A | 6.1 | 5.08 | 0.74 |
| MY2144 (fks 1-3) | 38.0 | 11.1 | 0.60 |
| MY2145 (fks 1-4) | 65.0 | 11.5 | 0.64 |

EXAMPLE 19
Cloning of a gene complementing nikkomycin Z supersensitivity.

A genetic cross was set up between MS14 (echinocandin-resistant and nikkomycin Z-sensitive) and the wild-type strain GG100-14D (echinocandin-sensitive and nikkomycin Z-resistant). The resultant diploid cells were sporulated and tetrads were dissected followed by phenotypic and drug resistance analysis of the meiotic segregants. The results demonstrated that the two phenotypes of echinocandin-resistance and nikkomycin Z supersensitivity co-segregate, suggesting a single gene mutation is responsible for the two phenotypes.

The strain D1-22C is a meiotic segregant from the above cross. This strain is echinocandin-resistant, nikkomycin Z-supersensitive and Ura⁻. Cells of strain D1-22C were transformed with the yeast DNA genomic library constructed in the centromere-based vector YCp50 (M. Rose et al., *Gene*, 60:237–243, 1987). This is the same DNA library that was used in Example 6. Double selection for uracil-prototrophy and nikkomycin Z-supersensitivity was conducted by plating the transformants on Ura dropout plates containing 75 mcg/ml of nikkomycin Z. Only colonies that can grow in absence of uracil and in the presence of nikkomycin Z will grow. Hence, this assay selected for transformants that have received the recombinant plasmids carrying DNA fragments capable of complementing the nikkomycin Z supersensitivity phenotype. Out of 20 uracil-prototrophic nikkomycin Z-resistant colonies isolated by this scheme, 3 clones were also sensitive to the echinocandin L-733,560. One of those three transformants is the strain designated 9-3B an contains a plasmid with the complementing gene. The plasmid in this strain was designated pMS14 since it complements the MS14 phenotypes in the transformed mutant cells (strain D1-22C). The pMS14 plasmid was rescued from the yeast cells (clone 9-3B), propagated in *E. coli* and retransformed into strain D1-22C. Three transforrnants were tested for resistance/sensitivity to L-733,560 and nikkomycin Z by the broth microdilution assay. In the 3 transformants tested, the echinocandin-resistance and the nikkomycin Z sensitivity, were reversed.

EXAMPLE 20
Allelism relationship between the mutations in MS10 and MS14

A uracil auxotroph carrying the echinocandin-resistance mutation from MS10 was constructed by crossing MS10 with GG100-14D. An echinocandin-resistant meiotic segregant was transformed with the single copy recombinant plasmid pMS14 and transformants were tested for susceptibility to echinocandins by the broth microdilution assay. All three transformants tested showed sensitivity to L-733, 560. In contrast, mutant cells transformed with the control plasmid YCp50 remained echinocandin-resistant. Thus, the recombinant plasmid pMS14, complementing both the echinocandin resistance and nikkomycin sensitivity phenotypes of the mutation from MS14 also complements the echinocandin resistant phenotype of MS10. This result suggests that the two mutations represent two different alleles of the same gene.

EXAMPLE 21

A. pJAM54 complements the mutations from MS10 and MS14

Yeast cells containing the mutations from either MS10 or MS14 were transformed with the multiple copy plasmid pJAM54 (containing FKS1). Like pMS14, pJAM54 complemented the two phenotypes of echinocandin resistance and nikkomycin sensitivity caused by the mutation from MS14. pJAM54 also complements the echinocandin resistance phenotype of strain MS10.

B. Cross-hybridization between pMS14 and pJAM54

The plasmid pJAM54 (a multicopy plasmid containing FKS1) and the single copy plasmid pMS14 were digested with restriction enzymes and analyzed by Southern hybridization analysis using an FKS1 internal fragment as a hybridization probe. Both Southern and restriction enzyme analysis showed that pJAM54 and pMS14 contain the same gene, namely FKS1. The mutation in MS10 is therefore referred to as fks1-3, and the mutation in MS14 is referred to as fks1-4.

EXAMPLE 22

Isolation of FKS1 and FKS2 homologs from Cryptococcus neoformans

To determine whether FKS1 homologs exist in the *C. neoformans* B-3502 chromosome, a sample of total genomic DNA from this strain was digested with HindIII, and fragments were separated on a 0.8% agarose gel. The gel was probed with the AflII-XhoI fragment from pJAM54 by the method of Southern, and washed under high stringency conditions. A fragment approximately 15 kb in length was visible on the autoradiogram. Most likely, this fragment contains all or a portion of the FKS1 homolog in *C. neoforrnans* B-3502.

Similar Southern blot hybridization experiments are carried out with an FKS2 fragment as the probe.

A phagemid cDNA library of poly (A)+ RNA from *C. neoformans* B-3502 is constructed essentially according to the method of Edman et al., (1990. *Mol. Cell Biol.*, 10(9) :4538–4544). *E. coli* XL-1B is co-infected with the phagemid library and a helper phage (R408) such that approximately 500 plaques are formed per agar plate. Plaques are lifted to nitrocellulose and probed by standard methods, using a fragment of FKS1 as a probe. After washing, filters are exposed to film, and the autoradiograph is used to identify specific phagemid clones which hybridize with FKS1. Plasmid DNA is then isolated from the cDNA transfectants, propagated, and analyzed by digestion with restriction endonucleases.

To isolate FKS2 homologs similar experiments are carried out with an FKS2 probe.

EXAMPLE 23

Isolation of FKS1 and FKS2 homologs from Pneumocystis carinii

Whole rat lungs from *P. carinii*-infected male Sprague-Dawley rats are homogenized with a Brinkmann homogenizer and DNA is isolated as described (P. A. Liberator, et al., 1992. *J. Clin. Micro.*, 30(11): 2968–2974). Two to five micrograms of purified DNA are digested with a restriction endonuclease such as EcoRI, and the fragments are separated on an agarose gel. DNA is transferred to a solid support such as nitrocellulose and probed by the method of Southern (Southern, E. M. 1975. *J. Mol. Biol.*, 98:503–517) for fragments with homology to FKS1. By washing the blot at a reduced stringency, weakly homologous genes can be identified.

Similar Southern blot hybridization experiments are carried out with an FKS2 fragment as the probe.

The *P. carinii* FKS1 homologs are cloned by preparing a mini-library from the region of the agarose gel where the hybridizing fragment was visualized on the Southern blot. Following phenol:$CHCl_3$ extraction to remove contaminants, DNA fragments from this area of the gel are ligated into an appropriate plasmid vector and transformed into *E. coli*. The *E. coli* clones bearing the mini-library are spread onto agar plates and probed for inserts homologous to FKS1 by in situ colony lysis. DNA from individual transformants is transferred to nitrocellulose, hybridized to a radiolabelled FKS1 DNA fragment, washed, and exposed to film. Colonies containing an insert with homology to FKS1 are visualized on the film; plasmid DNA is then isolated from positive clones, propagated, and analyzed. DNA sequence analysis by standard methods is used to establish the extent of homology to FKS1, and functional homology may be demonstrated by expression in *S. cerevisiae* disrupted for FKS1.

To isolate FKS2 homologs similar experiments are carried out with an FKS2 probe.

EXAMPLE 24

A. Cloning of Aspergillus homologs of FKS1 and FKS2

Genomic DNA was isolated from *A. nidulans* FGSCA4, also known as the Glasgow wild-type, and *A. nidulans* MF5668 by methods known to the art (Tang et al., (1992) *Mol. Microbiol.*, 6:1663–1671). The chromosomal DNA was cut to completion with several restriction enzymes and the digested fragments of DNA were separated by electrophoresis. The fragments of *A. fumigatus* DNA were transferred to Zeta-Probe GT quaternary amine derivatized nylon membrane which is manufactured by BioRad and the fragments of *A. nidulans* DNA were transferred to Nytran nylon membrane (S&S; Southern, (1975) *J. Mol. Biol.*, 98:503–517). Duplicate blots of the *A. nidulans* DNA were prepared. All of the blots were hybridized with $^{32}P$ probes radiolabeled by random priming (Feinberg and Vogelstein (1983) *Anal. Biochem.*, 132:6–13). The probe for the *A. fumigatus* blot was a radiolabeled 1.25-kb SalI-ClaI fragment isolated from pJAM54 which contains the FKS1 gene. One *A. nidulans* blot was also hybridized to this probe and the other *A. nidulans* blot was hybridized to a radiolabeled 1.7-kb KpnI-PstI fragment from pFF250 which contains a portion of the FKS2 gene. The blots were hybridized overnight under stringent conditions and washed by stringent methods (Maniatis et al., supra). The blots were then exposed to XAR-5 film and developed by conventional methods (Laskey and Mills (1977) *FEBS Letters*, 82:314–316). Both probes hybridized to fragments of each Aspergillus DNA tested. The blots illustrate that *A. nidulans* genomic DNA is homologous to both the *S. cerevisiae* 1.25 kb SalI-ClaI fragment from the FKS1 gene and the 1.7-kb KpnI-PstI fragment from the FKS2 gene. *A. fuimigatus* DNA is also homologous to the *S. cerevisiae* 1.25 kb SalI-ClaI fragment from the FKS1 gene.

To clone the *A. nidulans* homologs, two cosmid libraries of *A. nidulans* genomic DNA have been obtained from the Fungal Genetics Stock Center. Cosmid vectors are modified plasmids that contain "cos" sequences required for packaging DNA into bacteriophage lambda particles (Maniatis et al., supra). Cosmids also contain an origin of replication and a drug resistance marker and can be introduced into *E. coli* by standard transformation procedures and propagated as plasmids. Cos sequences enable 35- to 45-kb fragments of foreign DNA that are ligated to the vector to be packaged into lambda particles and to subsequently circularize upon infection of *E. coli*. Two complete cosmid libraries were constructed in the vectors LORIST2 and pWE15 by Brody et al., (*Nucleic Acids Research*, 19:3105–3109). Cosmid pWE15 contains a ColE1 origin of replication whereas LORIST2 contains a bacteriophage lambda origin of replication. DNA sequences that are unstable in one vector are often stable in the other (Evans et al., (1987). *Methods in Enzymnol.*, Berger and Kimmel Eds. Academic Press, New York. Vol. 152:604–610). Clones from the cosmid libraries are transferred to Nytran membranes and screened by methods known to the art (Maniatis et al.). The probes are the fragments from the FKS1 and FKS2 genes described above. If FKS1 and FKS2 homologs are absent from the cosmid libraries or the sequences are unstable, additional libraries are screened. If the homologs are absent from preexisting libraries or if only part of the gene is isolated, an *A. nidulans* genomic Sau3AI partial library is constructed in the Stratagene Vector Lambda Dash using a cloning kit obtained from the manufacturer and methods of the art (Maniatis).

Similar methodology is used to clone the *A. fumigatus* homologs of FKS1 and FKS2.

B. Isolation of *A. nidulans* homolog (fksA) of *S. cerevisiae* FKS1 and FKS2 by cross hybridization fksA is the designation for an *Aspergillus nidulans* homolog of FKS1 and FKS2. Homology at the DNA level was demonstrated between the *S. cerevisiae* FKS1 and FKS2 genes and genomic DNA of *A. nidulans*. This homology forms the basis of a strategy to clone *Aspergillus* homologs.

An *A. nidulans* genomic library constructed in the Stratagene cosmid vector pWE15 (Brody et al., 1991, *Nucleic Acids Research*, 19:3105–3109) was obtained from the Fungal Genetics Stock Center. This cosmid library consists of 2,832 individual cosmid containing *E. coli* transformants divided amongst 30 microtiter plates. One thousand four hundred eighty-eight transformants were transferred to Zeta-Probe GT quaternary amine derivatized nylon membranes (manufactured by BioRad) as colony blots.

The colony blots of the microtiter plates (96 colonies/plate; 1 blot/plate) were made as follows: individual cosmids were grown in LB broth (Maniatis, supra) in microtiter dishes overnight and were subsequently inoculated onto LB agar containing 50 micrograms per ml ampicillin. After seven hours of growth, two colony lifts were made from each plate and the filters were transferred to fresh plates. The colonies were grown an additional four hours and fixed to the filters. The filters were treated with 0.5N NaOH, neutralized with 1M Tris pH 7.5/1.5M NaCl, washed in 1M Tris pH 7.5/1.5M NaCl/0.2% SDS, and washed again in 1M Tris pH 7.5/1.5M NaCl. Duplicate blots were hybridized with a radiolabeled ($^{32}$P) 4.0 kb KpnI FKS1 fragment isolated from pJAM54 and a 1.7 kb PstI-KpnI fragment isolated from pFF250. All $^{32}$P probes were radiolabeled by random priming (Feinberg and Vogelstein (1983) *Anal. Biochem*, 132:6–13). The blots were hybridized using conditions recommended for Zeta membranes by the manufacturer Biorad. One colony was initially detected with only the FKS2 probe. This cosmid was designated pGS1, and hybridization to the FKS1 and FKS2 genes was subsequently confirmed by DNA slot blot analysis with purified cosmid DNA. Cosmid DNA was isolated from cultures grown for ten hours in LB medium and purified with a Qiagen plasmid maxi kit. Duplicate DNA slot blots were prepared by applying 1.5 micrograms of each sample to a Zeta-Probe GT quaternary amine derivatized nylon membrane (BioRad) with a Minifold II slot blot apparatus according to the directions of the manufacturer (Schleicher and Schuell). The samples were pGS1 DNA, vector pWE15 DNA, and DNA from a nonhybridizing cosmid. The slot blots were hybridized as described for the colony blots. Both the FKS1 and FKS2 probes hybridized specifically to the pGS1 DNA, and not to DNA from cosmid vector pWE15 or DNA isolated from a nonhybridizing colony.

The insert of cosmid pGS 1 was estimated to be ~30 kb by restriction endonuclease digestion and agarose gel electrophoresis and was released from the vector by digestion with either NotI or EcoRI. Specific restriction fragments from pGS1 with homology to FKS2 were identified by Southern blot hybridization using the same hybridization conditions. An 11.0 kb EcoRI fragment that hybridized to FKS2 was subcloned into vector Bluescript (Stratagene) to construct subclone pGS3. A restriction map was determined by restriction endonuclease digestion and agarose gel electrophoresis of the restriction fragments and is shown in FIG. 3. The region of pGS3 homologous to FKS2 was localized by Southern hybridization of blots of restriction fragments to the FKS2 probe. The 568 bp PstI-EcoRV fragment was determined to be internal to the hybridizing region and specific for fksA based on the following evidence: the 1.7 kb PstI fragment bordering on the left and the 2.4 kb EcoRV fragment bordering on the right hybridized to FKS2.

As some genomic libraries contain rearranged genes or DNA resulting from ligation of noncontiguous restriction fragments, Southern blot hybridization with the *S. cerevisiae* FKS2 gene and a homologous probe was performed to determine if cosmid pGS1 and its derivative, pGS3, were colinear with the *A. nidulans* genome. The homologous probe was the 568 bp fksA specific PstI-EcoRV fragment isolated from pGS2. Plasmid pGS2 was constructed by subcloning a 6.0 kb SalI fragment of pGS1 into Bluescript (Stratagene). *A. nidulans* genomic DNA was digested with SalI, EcoRI, EcoRV, KpnI, and EcoRI/SstII. The hybridization data indicated that the appropriate-sized restriction fragments of genomic DNA were found for enzymes proximal to the EcoRV site of the internal PstI-EcoRV fragment, but restriction fragments of genomic DNA corresponding to restriction sites distal of this EcoRV site were not found. Cosmid pGS1 and its derivative pGS3 are colinear with the *A. nidulans* genome from the left-hand EcoRI site to the second EcoRV site of the restriction map of pG53 shown in FIG. 3.

Figure 4:
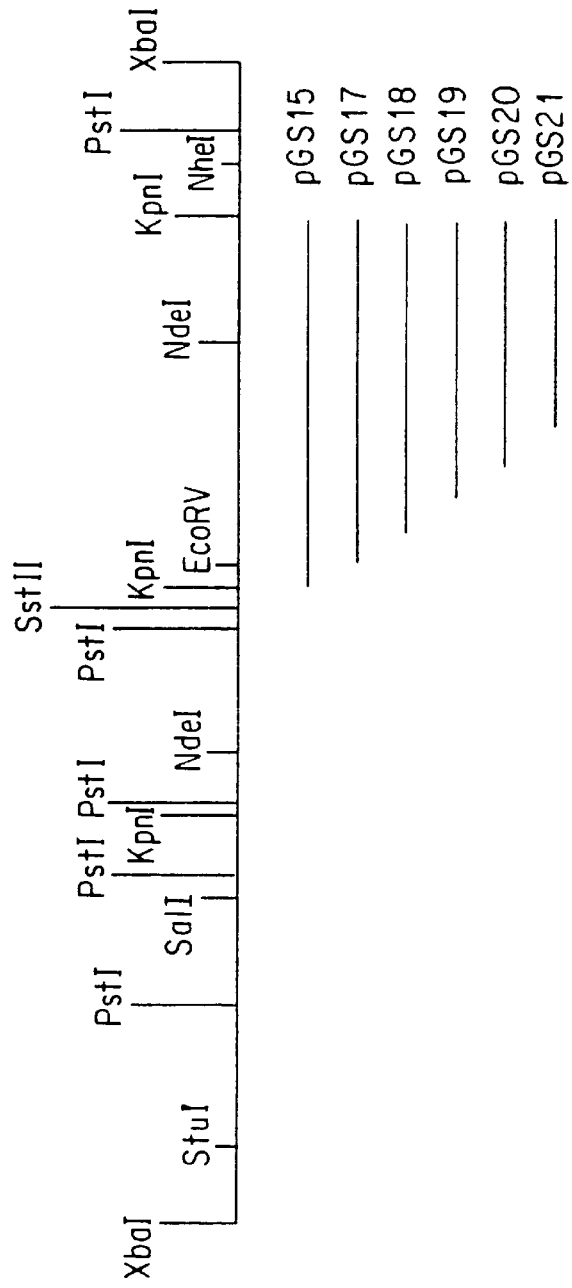
FIG. 4 is a restriction map of 11.0 kb XbaI insert of pGS6. The bold line designates the part of the fksA gene that was sequenced. The insert of pGS15 is shown and its derivatives containing the nested deletions (pGS17–pGS21).

To ensure isolation of a cosmid clone containing the entire *A. nidulans* fksA gene, another library was screened. An *A. nidulans* cosmid library constructed in vector pLORIST2 (Brody et al., 1991, *Nucleic Acids Research*, 19:3105–3109) was obtained from the Fungal Genetics Stock Center. The library was screened exactly as described for the isolation of pGS1, except that the probe was the *A. nidulans* internal 568 bp PstI-EcoRV fragment. One cosmid clone, p11G12, out of 2880 cosmids screened, hybridized strongly with the probe. DNA slot blot analysis with purified cosmid DNA confirmed hybridization to the *A. nidulans* homologous probe as well as to the FKS2 probe. The homologous probe was the 568 bp PstI-EcoRV fragment isolated from pGS4. Plasmid pGS4 was constructed by subcloning the 568p PstI-EcoRV fragment of pGS3 into Bluescript. Colinearity of p11G12 with *A. nidulans* genomic DNA was deter-mined by Southern blot hybridization with the FKS2 probe. The restriction enzymes tested were EcoRV-BglII, EcoRV-KpnI, EcoRV-SalI, PstI, SpeI, and XbaI. The restriction fragments obtained with p11G12 corresponded to those obtained with *A. nidulans* genomic DNA. The data indicated that the 568 bp PstI-EcoRV fragment specific for fksA is flanked on each side by ~7.0 kb of DNA that is colinear with the genome. An 11.0 kb XbaI fragment of p11G12 that hybridized to FKS2 and is colinear with the genome was subcloned into Bluescript to construct pGS6. A restriction map was determined by restriction endonuclease digestion and agarose gel electrophoresis of the restriction fragments and is shown in FIG. 4.

DNA sequence was determined either manually by the method of Sanger et al., (*Proc. Natl. Acad. Sci.*, 74:5463) using a "Sequenase" kit manufactured by United States Biochemical or using the Applied Biosystems Model 373A DNA Sequencing System with a "Prism Ready Reaction DyeDeoxy Terminator Cycle Sequencing Kit". Template DNA was obtained from the following plasmids: pGS4, pGS7, pGS6, pGS15, pGS 16, pGS17, pGS 18, pGS19, pGS20, and pGS21. Plasmid pGS7 was constructed by subcloning the 11.0 kb XbaI insert of pGS6 into pBR322. The 3.6 kb KpnI fragment and the 2.2 kb XhoI fragment of pGS6 were subcloned into pGEM7 to construct pGS15 and pGS 16, respectively. A set of nested deletions was constructed in pGS15 by partial Sau3A digestion using a method described by Gewain et al., (1992, *Gene*, 119:149). Briefly, plasmid pGS15 was linearized with BamHI which is in the multicloning site of the vector and the DNA was precipitated and resuspended. One microgram aliquots in 15 microliter reaction mixtures were subjected to partial digestion in 1X Sau3A buffer (New England Biolabs). The enzyme was diluted to 0.75 units/microliter in storage buffer (50 mM KCl, 10 mM TrisHCl, pH 7.4, 0.1 mM EDTA, 1 mM DTT, 200 mg/ml BSA, 50% glycerol) and serially diluted two-fold in storage buffer eight more times. One microliter of each dilution as well as the undiluted control was added to each tube containing 14 microliters and the mixture was incubated at 37° C. for 30 minutes. Reactions were terminated by the addition of 3.4 microliters of stop buffer containing 50 mM EDTA and heated at 65° C. for 20 minutes. The DNA was subjected to electrophoresis and fragments of the appropriate sizes were gel purified with a Qiagen Qiaquick protocol. The fragments were quantitated and religated with 25 ng of DNA per five microliter ligation reaction. The ligations containing the four largest fragments were precipitated and digested with Csp451 in five microliter reactions. The Csp451 site is between the BamHI and the KpnI site of the vector. This digestion was necessary to eliminate any contaminating fragments that did not contain a deletion. All of the DNA samples were transformed into DH5a FIQ, and the appropriate recombinants were identified by restriction endonuclease digestion. The deletions contained in plasmids pGS17, pGS18, pGS19, pGS20 and pGS21 are shown in FIG. 4.

Sequencing of the 568 bp PstI-EcoRV insert of pGS4 was initiated in both directions using KS and SK sequencing primers which bind to the vector (Stratagene). The fksA sequence was used to design primers to extend the sequence in both directions for each strand of the insert. Primers to each end of the sequence of the 568 bp insert of pGS4 were made and used to extend the fksA sequence with pGS7 as template. This information was used to design primers to extend the sequence in both directions using DNA from pGS 15 and pGS 16 as 5 template. Additional 3' sequence was obtained with plasmids pGS17, pGS18, pGS19, pGS20, and pGS21 which contain the nested deletions. Sequencing was initiated using an SP6 primer which binds to the vector (Promega) and in cases where the sequence of the plasmids did not overlap, a primer based on fksA sequence was used to extend the sequence. Primers based on fksA sequence were also used to obtain the sequence of the opposite strand using pGS6 as template. The sequence was assembled and analyzed with the University of Wisconsin Genetics Computer Group (GCG) sequence analysis software package.

The DNA sequence of 2565 nucleotides of fksA was determined with sequence of 1600 nucleotides based on both strands (FIG. 5). A putative open reading frame of 855 amino acids was deduced that exhibits 67% identity to *S. cerevisiae* FKS1 and FKS2 proteins. The amino acid sequences were compared with the GAP™ (GCG) program. The region of FKS2 homologous to fksA extends from amino acid 943 to amino acid 1799, the latter being close to the carboxy terminus. The first half of the fksA putative open reading frame (amino acids 1-427) is most homologous to FKS2 exhibiting 82% identity, whereas the latter half is 53% identical.

Localization of the fksA gene on pGS6 can be determined based on sequence information and transcript mapping. The portion of the fksA gene that has been sequenced begins 311 nucleotides to the left of the fourth PstI site of pGS6 as shown on the restriction map in FIG. 4. Based on the homology obtained between the fksA gene product and the Saccharomyces FKS1 and FKS2 gene products, it can be deduced that the direction of transcription of fksA is from left to right on the restriction map of pGS6 shown in FIG. 4. The fksA gene was further localized on pGS6 by transcript mapping. Total *A. nidulans* RNA was isolated by methods known to the art as described by Timberlake (*Biol. and Mol. Biol. of Plant-Pathogen Interactions*, 1986). The RNA was subjected to electrophoresis in 1.5% agarose, 2.2M formaldehyde, 1X MOPS buffer, transferred to nytran nylon membranes (Schleicher and Schuell) and hybridized according to a protocol of Gelman Sciences (Protocol Number 6, Application Protocols for BioTrace Binding Matrices). Hybridization of the fksA specific 568 bp PstI-EcoRV fragment of pGS4 to the gel blot detected a single transcript. An identical-sized transcript was detected by the two proximal PstI fragments of pGS6, a 1.2 kb PstI fragment and a 0.7 kb PstI fragment, but no transcript was detected with the 1.4 kb PstI-SpeI fragment of pGS3 which is 5' to the 1.2 kb PstI-PstI fragment (the 1.4 kb PstI-SpeI fragment was isolated from pGS9 which was constructed by subcloning the fragment from pGS3 into Bluescript). These data indicate that the fksA transcript begins within the 1.2 kb PstI-PstI fragment. The sequence data indicates that the fksA gene extends beyond the EcoRV site of pGS6. The 1.6 kb NdeI-NheI fragment of pGS6 did not detect a transcript, indicating that the transcript ends before the NdeI site. To summarize, the fksA transcript begins within the 1.2 kb PstI fragment and ends between the EcoRV and second NdeI site of pGS6. It is possible that regulatory sequences of the fksA gene are located 5' of the 1.2 kb PstI fragment.

EXAMPLE 25
Isolation of FKS homologs from phytopathogenic fungi

To clone FKS1 and FKS2 homologs from phytopathogenic fungi such as *Magnaporthe grisea* and *Ustilago maydis*, high molecular weight genomic DNA is isolated by the method described by Atkins and Lambowitz (*Mol. Cell. Biol.*, 5:2272–2278), partially digested by the restriction enzyme, Sau3AI, and cloned into the Stratagene Vector Lambda-Dash using a cloning kit obtained from the manufacturer and methods of the art (Maniatis). The libraries are screened using probes from FKS1 and FKS2 essentially as described above.

EXAMPLE 26

A. Isolation of the pcr1 (fks2-1) mutant

The L-733,560 resistant mutant MY2256 (also known as YFK0978 and YM0148) was isolated from strain YFK0931-07B using standard procedures. Four congenic (fks1-1) parental strains (YFK0931-03B, YFK0931-07B, YFK0931-10C, and YFK0932-01C) were used in the mutant hunt. The genotypes of the four strains are listed below. The strains contain plasmid pDL1 which contains an ARS element, a centromere and the CNB1, SUP11, and URA3 genes.

This mutant hunt was designed to identify mutations in the FKS2 gene that confer echinocandin resistance. Briefly, the parental strains were grown overnight in 5 ml of YPAD10Ca medium (YPAD medium containing 10 mM $CaCl_2$) at 28° C. Cells were diluted to $1 \times 10^3$ cells/ml in YPAD10Ca, and aliquots (0.2 ml) of the cultures were dispensed into 96 individual microtiter wells. The cultures were grown to saturation at 28° C. Cells from five wells were diluted 1:20 and the optical density at 660 nm ($OD_{660}$) was determined to calculate the average cell density for each culture (1 $OD_{660}=3.3\times10^7$ cells/ml).

Forty cultures of each strain were plated on YPAD10Ca medium containing 1 mcg/ml L-733,560. In addition 20 wells of YFK932-1C and YFK931-10C were diluted 1:10 and 1:100 and plated on YPAD10Ca medium containing 1 mcg/ml L-733,560. The plates were incubated at 28° C. Two colonies were picked from each drug plate, clonally purified on -Ura and YPAG medium and grown at 28° C. Two independent clones from each plate were picked to master plates of -Ura and YPAD10Ca media. The master plates were replica plated to standard drop-out medium, YPAD10Ca medium, and to YPAD10Ca medium containing either 1 mcg/ml of FK520, FK506, L-733,560, 10 mg/ml Cyclosporin A, or 0.1 mcg/ml rapamycin. The plates were incubated at 28° C. Temperature sensitivity was determined by replica plating the masters to YPAD medium and incubating the plates at 37° C. The plates were scored after two and three days.

From this experiment, eighteen independent mutants that grew on YPAD10Ca medium containing L-733,560 (1 mcg/ml) were identified from approximately $3.7 \times 10^9$ cells screened. These pcr (pneumocandin resistant) mutants were resistant to L-733,560 and sensitive to the immunosuppressants FK506, FK520, CsA, and rapamycin. One of the mutants (MY2256) also possessed a temperature sensitive phenotype at 37° C. The sensitivities of MY2256 and its parent strain (YFK0931-07B) to L-733,560, FK520, FK506, CsA, and rapamycin were measured, and the results are shown below. As shown in the table below, the mutant is significantly more resistant to L-733,560 than its parent. MY2256 and YFK0931-07B exhibit similar sensitivities to the immunosuppressants tested.

Mixed membrane fractions were prepared from MY2256 and YFKO931-07B and the sensitivity of 1,3-beta-D-glucan synthase activity to L-733,560 was assayed in the partially purified membrane preparations using standard procedures. The specific activities of 1,3-beta-D-glucan synthase activity from YFK0931-07B and MY2256 were 60 and 45 nmoles of UDP-D-[6-$^3$H]Glucose incorporated $mg^{-1}$ $hr^{-1}$. The IC50 of the enzyme activity from the mutant and parental strains were 16–24 mcM and 0.21 mcM, respectively, indicating that 1,3-beta-D-glucan synthase activity in MY2256 is resistant to L-733,560. MY2256 was further characterized.

EXAMPLE 27

Genetic characterization of the pcr1 mutant

MY2256 (MATa fks1-1 pcr1) was crossed to the wild type strain YFK0005 (MATalpha FKS1+PCR1+) to generate strain YFK0996-11B. YFK0996-11B (MATa fks1-1 pcr1) was mated to YFK0688-14B (MATalpha fks1-1 PCR1+), sporulated and dissected. In the 29 four-spore and 12 three-spore tetrads from this cross, the pcr1 phenotype (resistance to L-733,560) segregated $2^r:2^s$ indicating that the pcr1 phenotype is the result of a single mutation. Strains MY2259 (also known as YFK1087-20B, MATalpha fks1-1 pcr1) and MY2260 (also known as YFK1087-20A, MATa fks1-1 pcr1) were generated from this cross. Like the original MY2256 mutant, MY2259 and MY2260 contain the fks1-1 and pcr1 mutations. However, these strains do not contain plasmid pDL1 that was present in the original mutant.

YFK0996-11B (MATa fks1-1 pcr1) was also crossed to YFK0005 (MATalpha FKS1 PCR1). In this cross, the pcr1 and fks1-1 mutations segregate independently. In the 16 four-spore and 20 three-spore tetrads, the segregation pattern of 1 Parental Ditype: 1 Non Parental Ditype : 4 Tetratype tetrads is indicative of two unlinked genes. This cross also demonstrated that the pcr1 phenotype is expressed in an FKS1 background. FKS1 pcr1 spores are resistant to L-733,560 and the calcineurin inhibitors FK520, FK506, and CsA. Strains MY2257 (also known as YFK1088-23B, MATa FKS1 +pcr1), MY2258 (also known as YFK1088-16D, MATalpha FKS1+pcr1), and YFK1088-02D (MATa FKS1 +pcr1) were segregants from this cross. As shown in the table below, these segregants contain the pcr1 mutation in a wild-type FKS1 background and lack plasmid pDL1 present in the original mutant.

To determine if the pcr1 mutation mapped to the FKS2 gene, YFK1088-02D (MATa pcr1) was crossed to YFF2720 (MATalpha fks2::TRP1). In the 31 four-spore and 6 three-spore tetrads from this cross, all segregants demonstrated the parental phenotypes of resistance to L-733,560 (pcr1) and tryptophan auxotrophy (trp1) or sensitivity to L-733,560 and tryptophan prototrophy (fks2::TRP1). These results demonstrate that the pcr1 mutation is tightly linked to the FKS2 gene. In two additional crosses, YFK0996-23D (MATa pcr1 cnb1::LYS2) was mated to YFF2720 (MATalpha fks2::TRP1) and to YFF2721 (MATalpha fks2::TRP1). In the 78 tetrads tested, all of the fks2::TRP1 spores were sensitive to L-733,560 supporting the model that the pcr1 mutation maps to the FKS2 gene. Moreover, all of the cnb1::LYS2 spores from these crosses were sensitive to L-733,560. This would be expected if the mutation maps within the calcineurin-regulated FKS2 gene.

In summary, the pcr1 mutation is a single gene, segregates independently of fks1-1, is expressed in an FKS1 cell, and is tightly linked to the FKS2 gene. Accordingly, the pcr1 allele has been renamed as fks2-1.

B. Quantitating the level and spectrum of drug resistance of the pcr1 (fks2-1) mutant The sensitivities of pcr1(fks2-1) fks1-1 and pcr1(fks2-1) FKS1 strains to L-733,560, L-636,947 (Aculeacin), and L-687,781 (Dihydropapulocandin) were determined in MIC assays. Briefly, strains were grown to stationary phase in 5.0 ml of liquid YPAD medium. MY2256 precultures were grown in liquid YPAD10Ca. MIC assays were performed in flat well microtiter plates in triplicate. Each well of the microtiter plate was filled with 100 mcL of YPAD medium. To the first well, 100 mcL of a 4× solution of drug in YPAD medium was added. To serve as a control, a stock solution of 160 mcL DMSO per mcL of YPAD was made. 100 mcL of this solution was added to the initial well for strains grown in the presence of solvent but the absence of drug. Two-fold serial dilutions of the drug were performed down the plate.

Cultures were diluted to $5 \times 10^5$ cells/ml in YPAD (1 $OD_{660}=3.3 \times 10^7$ cells/ml). 100 mcL of diluted culture was added to each well, resuspended, and incubated at 28° C. After 42 hours, cultures were resuspended and cells densities measured in an SLT Laboratories 340 ATTC microtiter plate reader. The MICs concentrations presented in the table below represent the concentrations of drug that result in less than 10% growth of the strain grown in the absence of drug.

TABLE

| Strain | MIC (ng/ml) | | | | |
|---|---|---|---|---|---|
| | L-733,560 | FK506 | FK520 | CsA | Rapamycin |
| YFK0931-07B | 30 | 30 | 60 | 5000 | 7 |
| MY2256 | 4000 | 60 | 60 | 5000 | 7 |

TABLE

| Genotype/Strains | Tetrad Analysis of pcr1 vs fks1-1 | | |
|---|---|---|---|
| | Parental Ditype | Nonparental Ditype | Tetratype |
| pcr1 fks1-1 × FKS1 YFK0996-11B × YFK0005 | 5 | 1 | 10 four-spored |
| | 1 | 5 | 14 three-spored |
| | 6 | 6 | 24 total |
| | (6) | (6) | (24) expected |

TABLE

| Genotype/Strain | MIC (mcg/ml) | | |
|---|---|---|---|
| | L-733,560 | L-636,947 (Aculeacin) | L-687,781 (Dihydropapulocandin) |
| Wild type YFK0005 | 0.1 | 1 | 40 |
| fks1-1 PCR1 YFK0688-14B | 0.05 | 0.5 | 10 |
| fks1-1 pcr1 (fks2-1) MY2256 YFK0996-11B MY2259 MY2260 | 4 | >40 | >40 |
| FKS1 pcr1 (fks2-1) MY2257 MY2258 | 0.625 | >40 | >40 |

EXAMPLE 28
Cloning and Expression of 1,3-beta-D-glucan synthase subunit cDNA into Bacterial Expression Vectors Recombinant 1,3-beta-D-glucan synthase subunit is produced in a bacterial expression system such as *E. coli*. The 1,3-beta-D-glucan synthase subunit expression cassette is transferred into an *E. coli* expression vector; expression vectors include but are not limited to, the pET series (Novagen). The pET vectors place 1,3-beta-D-glucan synthase subunit expression under control of the tightly regulated bacteriophage T7 promoter. Following transfer of this construct into an *E. coli* host which contains a chromosomal copy of the T7 RNA polymerase gene driven by the inducible lac promoter, expression of 1,3-beta-D-glucan synthase subunit is induced by addition of an appropriate lac substrate (IPTG) is added to the culture. The levels of expressed 1,3-beta-D-glucan synthase subunit are determined by the assays described herein.

EXAMPLE 29
Cloning and Expression of 1,3-beta-D-glucan synthase subunit cDNA into a Vector for Expression in Insect Cells Baculovirus vectors derived from the genome of the AcNPV virus are designed to provide high level expression of cDNA in the Sf9 line of insect cells (ATCC CRL#1711). Recombinant baculovirus expressing 1,3-beta-D-glucan synthase subunit cDNA is produced by the following standard methods (InVitrogen Maxbac Manual): the 1,3-beta-D-glucan synthase subunit cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA (Kitts, P. A., *Nuc. Acid. Res.*, 18, 5667 (1990)) into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., *Texas Agriculture Exp. Station Bulletin No.* 1555). Following plaque purification, 1,3-beta-D-glucan synthase subunit expression is measured.

Authentic 1,3-beta-D-glucan synthase subunit receptor is found in association with the infected cells. Active 1,3-beta-D-glucan synthase subunit is extracted from infected cells by hypotonic or detergent lysis.

Alternatively, the 1,3-beta-D-glucan synthase subunit is expressed in the Drosophila Schneider 2 cell line by cotransfection of the Schneider 2 cells with a vector containing the modified receptor DNA downstream and under control of an inducible metallothionin promoter, and a vector encoding the G418 resistant neomycin gene. Following growth in the presence of G418, resistant cells are obtained and induced to express 1,3-beta-D-glucan synthase subunit by the addition of $CuSO_4$. Identification of modulators of the 1,3-beta-D-glucan synthase subunit is accomplished by assays using either whole cells or membrane preparations.

EXAMPLE 30
Purification of Recombinant 1,3-beta-D-glucan synthase subunit

Recombinantly produced 1,3-beta-D-glucan synthase subunit may be purified by a variety of procedures, including but not limited to antibody affinity chromatography.

Recombinant 1,3-beta-D-glucan synthase subunit antibody affinity columns are made by adding the anti-1,3-beta-D-glucan synthase subunit antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents, and the cell culture supernatants or cell extracts containing solubilized 1,3-beta-D-glucan synthase subunit is slowly passed through the column. The column is then washed with phosphate-buffered saline (PBS) supplemented with detergents until the optical density ($A_{280}$) falls to background; then the protein is eluted with 0.23M glycine-HCl (pH 2.6) supplemented with detergents. The purified 1,3-beta-D-glucan synthase subunit protein is then dialyzed against PBS.

EXAMPLE 31
Cloning and Expression of 1,3-beta-D-glucan synthase subunit in Mammalian Cell System 1,3-beta-D-glucan synthase subunit is cloned into a mammalian expression vector. The mammalian expression vector is used to transform a mammalian cell line to produce a recombinant mammalian cell line. The recombinant mammalian cell line is cultivated under conditions that permit expression of the 1,3-beta-D-glucan synthase subunit. The recombinant mammalian cell line or membranes isolated from the recombinant mammalian cell line are used in assays to identify compounds that bind to the recombinant 1,3-beta-D-glucan synthase subunit.

EXAMPLE 32
Screening Assay

Recombinant cells containing DNA encoding a 1,3-beta-D-glucan synthase subunit, membranes derived from the recombinant cells, or recombinant 1,3-beta-D-glucan synthase subunit preparations derived from the cells or membranes may be used to identify compounds that modulate 1,3-beta-D-glucan synthase subunit activity. Modulation of such activity may occur at the level of DNA, RNA, protein or combinations thereof. One method of identifying compounds that modulate 1,3-beta-D-glucan synthase subunit comprises:

(a) mixing a test compound with a solution containing 1,3-beta-D-glucan synthase subunit to form a mixture;

(b) measuring 1,3-beta-D-glucan synthase subunit activity in the mixture; and (c) comparing the 1,3-beta-D-glucan synthase subunit activity of the mixture to a standard.

EXAMPLE 33
DNA Sequence of FKS1

The DNA sequence of FKS1 was determined and is shown in FIG. 6.

EXAMPLE 34
Amino Acid Sequence of FKS1

The amino acid sequence of FKS1 was determined and is shown in FIG. 7.

EXAMPLE 35
DNA Sequence of FKS2

The DNA sequence of FKS2 was determined and is shown in FIG. 8.

EXAMPLE 36
Amino Acid Sequence of FKS2

The amino acid sequence of FKS2 was determined and is shown in FIG. 9.

EXAMPLE 37

To identify the fks1-1 mutation in strain R560-1C, gapped plasmids lacking a portion of the FKS1 coding sequence were prepared from plasmid pJAM54 by digestion with restriction enzymes (including but not limited to KpnI, SstI, BglII, XhoI) and purification by agarose gel electrophoresis. The gapped plasmids were purified from the gel using standard methods and transformed into strain R560-1C. Sixty Ura$^+$ transformants selected on uracil dropout medium were patched onto the same medium, grown for 24 h at 30° C., then replica plated to uracil dropout medium supplemented with 4 µg/ml L-733,560 and incubated for 2 days at 30° C. Growth of the clones on uracil-free drug-containing plates would suggest that: 1) the gapped plasmid was repaired at the ends of the gap through homologous recombination with the chromosome of strain R560-1C; and 2) the gap spanned the fks1-2 mutation. In contrast, if the gap spanned a region of the chromosome which did not contain the fks1-2 mutation, the repaired plasmid would carry the intact wild-type FKS1 gene, and the transformants would be partially drug-sensitive. Fifty-six of the sixty clones transformed with the KpnI-gapped version of pJAM54 were drug resistant. Plasmid DNA from these clones was isolated, amplified by propagation in E. coli, and transformed into YLIP137, a yeast strain with an insertion—deletion in the chromosomal copy of FKS1. Strain YLIP137 is phenotypically similar to strain YFF2409 described in Example 1, i.e., the chromosomal copy of FKS1 in YLIP137 has been functionally inactivated. The plasmid-borne copy of FKS1 is the only functional copy of FKS1 in these cells; if they are resistant to L-733,560, it must be because the plasmid carries the fks1-2 mutant version of FKS1. Ura$^+$ transformants of YLIP137 were selected on uracil dropout medium, and several clones were analyzed for susceptibility to L-733,560 by liquid MIC assays. All clones were as resistant to the drug as the original R560-1C mutant. We have designated the original gap-repaired plasmid carrying the fks1-2 mutation pJAM67.

The KpnI restriction fragment from plasmid pJAM67 is 3.5 kb in length. To identify a smaller fragment bearing the fks1-2 mutation, the fragments of the FKS1 gene in plasmid pJAM54 were replaced with the corresponding fragment from pJAM67 (fks1-2), transformed the new constructs into YLIP137, and assayed the clones for drug resistance using liquid MIC assays. In this manner, it was determined that the fks1-2 mutation was within a ca. 0.8-kb SalI-NcoI fragment of pJAM67. This fragment was subcloned into an E. coli plasmid suitable for DNA sequencing (pGEM3(z)f).

The sequence of the ca. 0.8-kb SalI-NcoI fragment was determined using the Model XXXX Automated DNA sequencer from Applied Biosystems, Inc, as per the manufacturer's specifications. Sequence data was analyzed using the GCG software package from the Genetics Computing Group, Madison Wis. Comparison of the DNA sequence of the SalI-NcoI fragment (exact length=711 bp) from pJAM67 to that of FKS1 revealed a single change. At nucleotide position 469 of the FKS1 SalI-NcoI fragment, the base is T (thymine); in the fks1-2 DNA fragment, the nucleotide base at the corresponding position is A (adenine). When translated into protein, this change results in the substitution of isoleucine (Fks1-2p) for phenylalanine (Fks1p) at position 639 of the 1877 amino acid protein primary sequence. One hypothesis is that this change is responsible for the L-733,560 resistance of both strain R560-1C and the 1,3-b-D-glucan synthase activity derived from it.

EXAMPLE 38

Total genomic DNA from Candida albicans ATCC10261 was digested to completion with BamHI and KpnI and separated by agarose gel electrophoresis using a 0.8% gel. A portion of the DNA fragments from the gel was transfered to a nitrocellulose filter and probed with a 1.25-kbSalI- ClaI fragment from S. cerevisiae FKS1 by Southern blotting (Maniatis, supra). A ca. 2-kb fragment of Candida DNA hybridized to the probe, and the fragments from the corresponding region of the remainder of the gel were excised, purified by standard methods, and ligated into vector pGEM3(z)f (Stratagene) digested with BamHI and KpnI. The ligation mixture was transformed into competent cells of E. coli, and plasmid-bearing transformants were selected on medium containing ampicillin and pooled. To identify clones which carried a plasmid with the 2-kb *C. albicans* FKS1-homologous DNA, aliquots of the pooled transformants were spread on selective medium, and colonies were transferred to nitrocellulose, lysed by standard methods, and probed with the [$^{32}$P]-labeled 1.25-kb SalI-ClaI fragment isolated from pJAM54. Filters were washed under stringent conditions and exposed to film. Nineteen colonies appeared to give a positive signal on the blot. Using the original colony as a source, cells from each of the potential clones were grown in liquid medium and plasmid DNA was isolated. The DNA was digested with KpnI and BamHI, and fragments separated on 0.8% agarose gels were probed with the radiolabeled 1.25-kb SalI- ClaI fragment from pJAM54 by Southern blotting. Three of the nineteen plasmids contained a ca. 2-kb fragment which hybridized intensely with the probe. The plasmid with the KpnI-BamHI fragment of the *C. albicans* FKS1 homolog has been designated as pGJS 1. The Candida gene gene which is homologous to FKS1 was designated FKS1 can.

The nucleotide sequence of the ca. 2-kb fragment from pGJS1 was determined using standard methods. For the first two sequencing reactions, denatured pGJS I DNA was annealed to the "T7 primer" and "SP6 primer" available from Stratagene. All other reagents, including the enzyme "Sequenase v. 2", were from U.S. Biochemicals and were used according to the manufacturer's specifications. The DNA sequence results from the first reactions were used to design 18-base oligonucleotide primers which were complementary to the "end" of the sequence from these first reactions. These primers were used in the next set of reactions. The process was continued until a contiguous protein-encoding open reading frame could be generated from the data from individual sequencing reactions, using the GCG analysis programs from the Genetics Computing Group (Madison, Wis.).

The predicted peptide sequence of the *C. albicans* FKS homolog (Fksc1p) was compared to the protein sequence of Fks1p from *S. cerevisiae*. Amino acids 1 through 689 of Fksc1p aligned with residues 460 through 1147 of Fks1p, using the GAP program of the Genetics Computing Group. The two peptide sequences were 79% identical and 88% similar to one another over this range. This constitutes a very high degree of homology and suggests that the two proteins are very likely to be functionally similar. In particular, phenylalanine at position 639 of Fks1p, which was identified in the mutant gene fks1-2 as a residue important for wild-type susceptibility to echinocandin inhibition (supra) was identical to phenylalanine 180 of the Fksc1p amino acid sequence given in Figure CD1. It is believed that: 1) FKS1 can encodes an echinocandin-sensitive subunit of the *C. albicans* 1,3-beta-D-glucan synthase; 2) the remainder of the Fksc1p protein sequence will show a similar degree of homology to Fks1p; 3) Mutations in FKS1 can similar but not limited to the fks1-2 mutation will result in decreased susceptibility of both enzyme activity (1,3-beta-D-glucan synthase containing the mutant Fksc1p subunit) and whole cells (*C. albicans* cells expressing the mutant Fksc1p) to echinocandin inhibition.

EXAMPLE 39

The effect of loss of a functional copy of either FKS1 or FKS2 on sensitivity to yeast killer toxin was evaluated. The toxin-susceptibility test requires that the test strain lack the $M_1$ killer virus, since strains containing the virus produce toxin ($K^+$) and are immune ($I^+$) to its action, and it is not possible to distinguish the killer resistant (Kre$^-$) phenotype from the immune ($I^+$) phenotype. The strains constructed with insertion—deletions of either FKS1 (YLIP179 and YLIP183; fks1::HIS3) or FKS2 (YLIP186 and YLIP190; fks2::TRP1) were $K^+I^+$; therefore, the $M_1$ virus had to be cured from the strains before the Kre phenotype could be assayed. YLIP179, YLIP183, YLIP186 and YLIP190 were grown overnight at 37° C. The next day, an aliquot of the overnight culture was transferred to fresh medium (1:1000 dilution) and incubation at 37° C. was continued. After three passages, cells from the culture were streaked onto agar plates, and single colonies were isolated and tested for failure to produce killer toxin in a patch assay. The patch assay was performed by: 1) Adding $1\times10^5$ logarithmic-phase cells of the killer toxin supersensitive strain S6 to molten YPAD agar containing 0.25M citrate buffer, pH 4.7 and 0.03% methylene blue (YPAD Cit MB); 2) Pouring plates and allowing the seeded agar to solidify; 3) Applying a patch of the test strain to the surface of the plate; and 4) Incubating at 25° C. for 24 h and looking for a zone of clearing around the patch. Strains which failed to produce a zone were not expressing active toxin ($K^-$) and were not immune ($I^-$). Derivatives of YLIP179, YLIP183, YLIP186, and YLIP190 cured of the M1-killer virus by this procedure were tested for susceptibility to killer toxin by a modification of the patch assay. Each test strain was seeded in molten YPAD Cit MB agar and a superkiller strain (K12) was applied as the patch. Under these conditions, there is little to no zone in the lawn of cells when the test strain is Kre$^-$. All of the $K^-$ $I^-$ isolates derived from fks1::HIS3 strains and fks2::TRP1 strains were sensitive to the toxin produced by strain K12; control assays with several known Kre$^-$ strains (S706, S708, and S726; described in U.S. Pat. No. 5,194,600, Tables I and VI) performed under the same conditions showed little to no zone. Therefore, loss-of-functions mutations in either FKS1 or FKS2 resulted in cells which were phenotypically distinct from strains with loss of function mutations in any of the KRE genes described in U.S. Pat. No. 5,194,600.

EXAMPLE 40

The susceptibility of two different kre mutants to inhibitors of 1,3-b-D-glucan synthase was measured. Strains S442 (KRE1 KRE5) S708 (kre1-3) and S726 (kre5-1) were grown in liquid YPAD medium to stationary phase then seeded in molten YPAD agar at a final concentration of $1\times10^5$ cells per ml before pouring into petri plates. To test for drug sensitivity, pneumocandin $B_0$, echinocandin B, dihydropapulacandin, and L-733,560 (four known inhibitors of 1,3-beta-D-glucan synthase) were applied to the surface of the plates, and the diameter of each zone of growth inhibition was measured after growth at 30° C. for 24 h. The methodology for this assay is essentially as described above, and strains R560-1C, W303-1A, YLIP179 (fks1::HIS3) and YLIP186 (fks2::TRP1) were tested under the same conditions for comparison. Zone diameter is usually a good indicator of susceptibility to an inhibitor and can be used to score resistance or hypersensitivity relative to a congenic wild-type strain. Using these criteria, R560-1C cells were resistant, YLIP179 cells were hypersensitive, and YLIP186 cells were like the wild-type strain in susceptibility to the four 1,3-beta-D-glucan synthase inhibitors. In contrast, the kre mutants [S708 (kre1-3) and S726 (kre5-1)] were equivalent to their wild-type parent strain (S442) in susceptibility to all four compounds. Therefore, there was no affect of the kre mutations on sensitivity to these 1,3-beta-D-glucan synthase inhibitors, while mutant alleles of FKS1 resulted in either resistance (fks1-2) or hypersensitivity (fks1::HIS3) to these compounds. The results imply that a microbial assay for inhibitors of 1,3-beta-D-glucan synthase based on differential susceptibility of a mutant/wild-type strain pair would not be effective with these kre mutants but could be effective with these fks1 mutants.

What is claimed is:

1. An essentially pure DNA molecule having a nucleotide sequence selected from the group consisting of SEQ. ID. NO.:1, SEQ. ID. NO.:3, SEQ. ID. NO.:5 and SEQ. ID. NO.:7.

2. The DNA molecule of claim 1 which is isolated from a microorganism.

3. The DNA molecule of claim 2, wherein the microorganism is selected from the group consisting of *Aspergillus fumigatus, Aspergillus nidulans, Candida albicans, Cryptococcus neoformans, Pneumocystis carinii* and *Saccharomyces cerevisiae*.

4. The DNA molecule of claim 2, wherein the microorganism is *Saccharomyces cerevisiae*.

5. The DNA molecule of claim 1, wherein the DNA molecule is operably linked to regulatory sequences such that the DNA may be expressed upon introduction into a prokaryotic or eukaryotic cell.

6. An essentially purified protein encoded by the DNA molecule of claim 1.

7. The protein of claim 6 having an amino acid sequence selected from the group consisting of SEQ. ID. NO.:2, SEQ. ID. NO.:4, SEQ. ID. NO.:6 and SEQ. ID. NO.:8.

8. A cell transformed with the DNA molecule of claim 1.

9. A microorganism selected from the group consisting of YFK532-7C, R560-1C, MS14, YFK0978, YFK1088-23B, YFK1088-16D, YFK1087-20B, and YFK1087-20A.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 7655 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:1:

```
GCATGCAAAC  ATCTACACAA  TTAGCAAGGG  CAATCCATAT  TTTGTCTTTT  CGCGCCCTGG      60
AAAGGCCTAA  GTAATGTCGT  AAACGCATTC  TATCTGTACT  TCAACTCTCC  TCTGTGCATT     120
GGTTTGTGCA  AATCACATTT  TACGATACTG  CCAGATTTAT  GCAAAAGAG   AAAACCAAGG     180
GACCAGAACA  AAGCAAAATT  ACGATAAACT  TCGAATTCCT  TCGTGCTTGA  CTAAGACAAA     240
GGGATGGACG  TAGCGATTTT  TAGCGGGCCA  AGAACTGGTT  CCGAAAAAGC  ACAGGTACAC     300
CGAACCCTCA  GCTAAGGAGG  GACAGCACCG  ATGCGGAAGG  ACAAACTTTC  TTTTTGCCTA     360
TCACAGTATC  TTATCGAGCT  AACTATTTTC  GACACACATG  AAAAAGCAGA  AATATTAACG     420
AAAAAGAAAA  GAAAGACCAT  GTCATGTACG  GGCAATCAGA  ATCTGTAACA  AGCGCCATTT     480
TTTTTTCTGT  ATCGGGCCCT  CCTTACTGCT  CTCCTTCCGT  GTAACGCGTT  ATGAAACTCT     540
AATCCTACTA  TCGGCGACTC  TCTCGAAATT  TTTCTTAACG  CGTCCTTGTA  CTGCGTCTAA     600
CGCTTTTGCC  ACTTGGATTT  CTATTATAGG  AAATAGTCTC  ACTTACTGGG  CGACGAATTT     660
TCGCGTTTTG  ATGAAGCACA  GGAAGAATTT  CTTTTTTTT   TGGCTTCTTC  TGGTTCCGTT     720
TTTTACGCGC  ACAAATCTAA  AAAAAGAAAT  AATTATAACC  TAGTCTCGAA  AATTTTCATC     780
GATCCATTCG  TTCCTTTTTT  TCGATTTTTT  CAGATCAAAA  TTCTTGTTTC  TTTCTTTGTC     840
TTAGTTTATA  TTAAAAGATA  TTTTGATTTT  ACTCCTGAAC  TATTTATTCT  TTCTAAGAAG     900
GCCAGAACAC  TACAGCTGTT  TTAACCGACT  ACGAAGTTCT  CCATTCTCGA  ACACTAGCCT     960
TCATTTACCA  AACAGGAACT  AGCGTATATC  ATTAGTCCTT  ATTCGAAAAG  AGATTGGTAG    1020
ATATTTATTG  TAGTTTGTGA  GAAGGAGAAA  ATACTGTCAT  TGGACTGATA  GTTAGAGGAC    1080
ATTAACCTCT  CTTACGTTCG  CTCAAAAAAA  TTAAAATAAG  CAAGTAGCTG  AAATCAAGTC    1140
TTTCATACAA  CGGTCAGACC  ATGAACACTG  ATCAACAACC  TTATCAGGGC  CAAACGGACT    1200
ATACCCAGGG  ACCAGGTAAC  GGGCAAAGTC  AGGAACAAGA  CTATGACCAA  TATGGCCAGC    1260
CTTTGTATCC  TTCACAAGCT  GATGGTTACT  ACGATCCAAA  TGTCGCTGCT  GGTACTGAAG    1320
CTGATATGTA  TGGTCAACAA  CCACCAAACG  AGTCTTACGA  CCAAGACTAC  ACAAACGGTG    1380
AATACTATGG  TCAACCGCCA  AATATGGCTG  CTCAAGACGG  TGAAAACTTC  TCGGATTTTA    1440
GCAGTTACGG  CCCTCCTGGA  ACACCTGGAT  ATGATAGCTA  TGGTGGTCAG  TATACCGCTT    1500
CTCAAATGAG  TTATGGAGAA  CCAAATTCGT  CGGGTACCTC  GACTCCAATT  TACGGTAATT    1560
ATGACCCAAA  TGCTATCGCT  ATGGCTTTGC  CAAATGAACC  TTATCCCGCT  TGGACTGCTG    1620
ACTCTCAATC  TCCCGTTTCG  ATCGAGCAAA  TCGAAGATAT  CTTTATTGAT  TTGACCAACA    1680
GACTCGGGTT  CCAAAGAGAC  TCCATGAGAA  ATATGTTTGA  TCATTTTATG  GTTCTCTTGG    1740
ACTCTAGGTC  CTCGAGAATG  TCTCCTGATC  AAGCTTTACT  ATCTTTACAT  GCCGACTACA    1800
```

```
TTGGTGGCGA  TACTGCTAAC  TATAAAAAAT  GGTATTTTGC  TGCTCAGTTA  GATATGGATG    1860

ATGAAATTGG  TTTTAGAAAT  ATGAGTCTTG  GAAAACTCTC  AAGGAAGGCA  AGAAAAGCTA    1920

AGAAGAAAAA  CAAGAAAGCA  ATGGAAGAGG  CCAATCCCGA  AGACACTGAA  GAAACTTTAA    1980

ACAAAATTGA  AGGCGACAAC  TCCCTAGAGG  CTGCTGATTT  TAGATGGAAG  GCCAAGATGA    2040

ACCAGTTGTC  TCCCCTGGAA  AGAGTTCGTC  ATATCGCCTT  ATATCTGTTA  TGTTGGGGTG    2100

AAGCTAATCA  AGTCAGATTC  ACTGCTGAAT  GTTTATGTTT  TATCTACAAG  TGTGCTCTTG    2160

ACTACTTGGA  TTCCCTCTT   TGCCAACAAC  GCCAAGAACC  TATGCCAGAA  GGTGATTTCT    2220

TGAATAGAGT  CATTACGCCA  ATTTATCATT  TCATCAGAAA  TCAAGTTTAT  GAAATTGTTG    2280

ATGGTCGTTT  TGTCAAGCGT  GAAAGAGATC  ATAACAAAAT  TGTCGGTTAT  GATGATTTAA    2340

ACCAATTGTT  CTGGTATCCA  GAAGGTATTG  CAAAGATTGT  TCTTGAAGAT  GGAACAAAAT    2400

TGATAGAACT  CCCATTGGAA  GAACGTTATT  TAAGATTAGG  CGATGTCGTC  TGGGATGATG    2460

TATTCTTCAA  AACATATAAA  GAGACCCGTA  CTTGGTTACA  TTTGGTCACC  AACTTCAACC    2520

GTATTTGGGT  TATGCATATC  TCCATTTTTT  GGATGTACTT  TGCATATAAT  TCACCAACAT    2580

TTTACACTCA  TAACTATCAA  CAATTGGTCG  ACAACCAACC  TTTGGCTGCT  TACAAGTGGG    2640

CATCTTGCGC  ATTAGGTGGT  ACTGTCGCAA  GTTTGATTCA  AATTGTCGCT  ACTTTGTGTG    2700

AATGGTCATT  CGTTCCAAGA  AAATGGGCTG  GTGCTCAACA  TCTATCTCGT  AGATTCTGGT    2760

TTTTATGCAT  CATCTTTGGT  ATTAATTTGG  GTCCTATTAT  TTTTGTTTTT  GCTTACGACA    2820

AAGATACAGT  CTACTCCACT  GCTGCACACG  TTGTTGCTGC  TGTTATGTTC  TTTGTTGCGG    2880

TTGCTACCAT  CATATTCTTC  TCCATTATGC  CATTGGGGGG  GTTGTTTACG  TCATATATGA    2940

AAAAATCTAC  AAGGCGTTAT  GTTGCATCTC  AAACATTCAC  TGCTGCATTT  GCCCCTCTAC    3000

ATGGGTTAGA  TAGATGGATG  TCCTATTTAG  TTTGGGTTAC  TGTTTTTGCT  GCCAAATATT    3060

CAGAATCGTA  CTACTTTTTA  GTTTATCTT   TGAGAGATCC  AATTAGAATT  TTGTCCACCA    3120

CTGCAATGAG  GTGTACAGGT  GAATACTGGT  GGGGTGCGGT  ACTTTGTAAA  GTGCAACCCA    3180

AGATTGTCTT  AGGTTTGGTT  ATCGCTACCG  ACTTCATTCT  TTTCTTCTTG  GATACCTACT    3240

TATGGTACAT  TATTGTGAAT  ACCATTTTCT  CTGTTGGGAA  ATCTTTCTAT  TTAGGTATTT    3300

CTATCTTAAC  ACCATGGAGA  AATATCTTCA  CAAGATTGCC  AAAAAGAATA  TACTCCAAGA    3360

TTTTGGCTAC  TACTGATATG  GAAATTAAAT  ACAAACCAAA  GGTTTTGATT  TCTCAAGTAT    3420

GGAATGCCAT  CATTATTTCA  ATGTACAGAG  AACATCTCTT  AGCCATCGAC  CATGTACAAA    3480

AATTACTATA  TCATCAAGTT  CCATCTGAAA  TCGAAGGTAA  AAGAACTTTG  AGAGCTCCTA    3540

CCTTCTTTGT  TTCTCAAGAT  GACAATAATT  TTGAGACTGA  ATTTTTCCCT  AGGGATTCAG    3600

AGGCTGAGCG  TCGTATTTCT  TTCTTTGCTC  AATCTTTGTC  TACTCCAATT  CCCGAACCAC    3660

TTCCAGTTGA  TAACATGCCA  ACGTTCACAG  TATTGACTCC  TCACTACGCG  GAAAGAATTC    3720

TGCTGTCATT  AAGAGAAATT  ATTCGTGAAG  ATGACCAATT  TTCTAGAGTT  ACTCTTTTAG    3780

AATATCTAAA  ACAATTACAT  CCCGTTGAAT  GGGAATGTTT  TGTTAAGGAT  ACTAAGATTT    3840

TGGCTGAAGA  AACCGCTGCC  TATGAAGGAA  ATGAAAATGA  AGCTGAAAAG  GAAGATGCTT    3900

TGAAATCTCA  AATCGATGAT  TTGCCATTTT  ATTGTATTGG  TTTTAAATCT  GCTGCTCCAG    3960

AATATACACT  TCGTACGAGA  ATTTGGGCTT  CTTTGAGGTC  GCAGACTCTA  TATCGTACCA    4020

TTTCAGGGTT  CATGAATTAT  TCAAGAGCTA  TCAAATTACT  GTATCGTGTG  GAAAATCCTG    4080

AAATTGTTCA  AATGTTTGGT  GGTAATGCTG  AAGGCTTAGA  AAGAGAGCTA  GAAAGATGG    4140

CAAGAAGAAA  GTTTAAATTT  TTGGTCTCTA  TGCAGAGATT  GGCTAAATTC  AAACCACATG    4200
```

```
AACTGGAAAA  TGCTGAGTTT  TTGTTGAGAG  CTTACCCAGA  CTTACAAATT  GCCTACTTGG  4260
ATGAAGAGCC  ACCTTTGACT  GAAGGTGAGG  AGCCAAGAAT  CTATTCCGCT  TTGATTGATG  4320
GACATTGTGA  AATTCTAGAT  AATGGTCGTA  GACGTCCAA   GTTTAGAGTT  CAATTATCTG  4380
GTAACCCAAT  TCTTGGTGAC  GGTAAATCTG  ATAACCAAAA  CCATGCTTTG  ATTTTTTACA  4440
GAGGTGAATA  CATTCAATTA  ATTGATGCCA  ACCAAGATAA  CTACTTGGAA  GAATGTCTGA  4500
AGATTAGATC  TGTATTGGCT  GAATTTGAGG  AATTGAACGT  TGAACAAGTT  AATCCATATG  4560
CTCCCGGTTT  AAGGTATGAG  GAGCAAACAA  CTAATCATCC  TGTTGCTATT  GTTGGTGCCA  4620
GAGAATACAT  TTTCTCTGAA  AACTCTGGTG  TGCTGGGTGA  TGTGGCCGCT  GGTAAAGAAC  4680
AAACTTTTGG  TACATTATTT  GCGCGTACTT  TATCTCAAAT  TGGTGGTAAA  TTGCATTATG  4740
GTCATCCGGA  TTTCATTAAT  GCTACGTTTA  TGACCACTAG  AGGTGGTGTT  TCCAAAGCAC  4800
AAAAGGGTTT  GCATTTAAAC  GAAGATATTT  ATGCTGGTAT  GAATGCTATG  CTTCGTGGTG  4860
GTCGTATCAA  GCATTGTGAG  TATTATCAAT  GTGGTAAAGG  TAGAGATTTG  GGTTTCGGTA  4920
CAATTCTAAA  TTTCACTACT  AAGATTGGTG  CTGGTATGGG  TGAACAAATG  TTATCTCGTG  4980
AATATTATTA  TCTGGGTACC  CAATTACCAG  TGGACCGTTT  CCTAACATTC  TATTATGCCC  5040
ATCCTGGTTT  CCATTTGAAC  AACTTGTTCA  TTCAATTATC  TTTGCAAATG  TTTATGTTGA  5100
CTTTGGTGAA  TTTATCTTCC  TTGGCCCATG  AATCTATTAT  GTGTATTTAC  GATAGGAACA  5160
AACCAAAAAC  AGATGTTTTG  GTTCCAATTG  GGTGTTACAA  CTTCCAACCT  GCGGTTGATT  5220
GGGTGAGACG  TTATACATTG  TCTATTTTCA  TTGTTTTCTG  GATTGCCTTC  GTTCCTATTG  5280
TTGTTCAAGA  ACTAATTGAA  CGTGGTCTAT  GGAAAGCCAC  CCAAAGATTT  TTCTGCCACC  5340
TATTATCATT  ATCCCTATG   TTCGAAGTGT  TTGCGGGCCA  AATCTACTCT  TCTGCGTTAT  5400
TAAGTGATTT  AGCAATTGGT  GGTGCTCGTT  ATATATCCAC  CGGTCGTGGT  TTTGCAACTT  5460
CTCGTATACC  ATTTTCAATT  TTGTATTCAA  GATTTGCAGG  ATCTGCTATC  TACATGGGTG  5520
CAAGATCAAT  GTTAATGTTG  CTGTTCGGTA  CTGTCGCACA  TTGGCAAGCT  CCACTACTGT  5580
GGTTTTGGGC  CTCTCTATCT  TCATTAATTT  TTGCGCCTTT  CGTTTTCAAT  CCACATCAGT  5640
TTGCTTGGGA  AGATTTCTTT  TTGGATTACA  GGGATTATAT  CAGATGGTTA  TCAAGAGGTA  5700
ATAATCAATA  TCATAGAAAC  TCGTGGATTG  GTTACGTGAG  GATGTCTAGG  GCACGTATTA  5760
CTGGGTTTAA  ACGTAAACTG  GTTGGCGATG  AATCTGAGAA  AGCTGCTGGT  GACGCAAGCA  5820
GGGCTCATAG  AACCAATTTG  ATCATGGCTG  AAATCATACC  CTGTGCAATT  TATGCAGCTG  5880
GTTGTTTTAT  TGCCTTCACG  TTTATTAATG  CTCAAACCGG  TGTCAAGACT  ACTGATGATG  5940
ATAGGGTGAA  TTCTGTTTTA  CGTATCATCA  TTTGTACCTT  GGCGCCAATC  GCCGTTAACC  6000
TCGGTGTTCT  ATTCTTCTGT  ATGGGTATGT  CATGCTGCTC  TGGTCCCTTA  TTTGGTATGT  6060
GTTGTAAGAA  GACAGGTTCT  GTAATGGCTG  GAATTGCCCA  CGGTGTTGCT  GTTATTGTCC  6120
ACATTGCCTT  TTTCATTGTC  ATGTGGGTTT  TGGAGAGCTT  CAACTTTGTT  AGAATGTTAA  6180
TCGGAGTCGT  TACTTGTATC  CAATGTCAAA  GACTCATTTT  TCATTGCATG  ACAGCGTTAA  6240
TGTTGACTCG  TGAATTTAAA  AACGATCATG  CCAATACAGC  CTTCTGGACT  GGTAAGTGGT  6300
ATGGTAAAGG  TATGGGTTAC  ATGGCTTGGA  CCCAGCCAAG  TAGAGAATTA  ACCGCCAAGG  6360
TAATTGAGCT  TTCAGAATTT  GCAGCTGATT  TTGTTCTAGG  TCATGTGATT  TTAATCTGTC  6420
AACTGCCACT  CATTATAATC  CCAAAAATAG  ATAAATTCCA  CTCGATTATG  CTATTCTGGC  6480
TAAAGCCCTC  TCGTCAAATT  CGTCCCCCAA  TTTACTCTCT  GAAGCAAACT  CGTTTGCGTA  6540
AGCGTATGGT  CAAGAAGTAC  TGCTCTTTGT  ACTTTTTAGT  ATTGGCTATT  TTTGCAGGAT  6600
```

-continued

```
GCATTATTGG  TCCTGCTGTA  GCCTCTGCTA  AGATCCACAA  ACACATTGGA  GATTCATTGG   6660

ATGGCGTTGT  TCACAATCTA  TTCCAACCAA  TAAATACAAC  CAATAATGAC  ACTGGTTCCC   6720

AAATGTCAAC  TTATCAAAGT  CACTACTATA  CTCATACGCC  ATCATTAAAG  ACCTGGTCAA   6780

CTATAAAATA  ATACAATCAA  TACTTGCTTG  AACGCTTGAT  TTTACTGATA  TTCTATCCAA   6840

AAGCAAGTAG  ACCAGAAACT  CTCAAGATGT  TGCAAATACC  GTTCGATGTT  TTTGGTTTAG   6900

ATTGTTTTAA  TGTTGATGCT  TTTTTACTTA  TTTTTGGAAG  CGTCTTTTTA  ATTTAGTTTT   6960

ATATTATAGG  TATATGAATG  TGTTTATGCC  AATAAGGGTT  TTTTTGTACA  GTTATGTGAT   7020

TATAAACAGT  CTTTTGTCTA  GTTTTTTTCA  CCAGTATCGG  CCTCTATTTA  TAAAAAACGG   7080

AGCAGCTTTC  GGTGTCAGTA  ATTCTGAAAA  AATTTGTGTC  ACTCTGATTG  TAAATGAATT   7140

AATTTAGCTA  GATAGTTGCG  AGCCCCAACG  AGAAGATTGT  CAGACAAAGA  CAACATTCAA   7200

CAACCTACAT  CCGTTACTAT  TCGTTAACTC  GAGGTACTTG  AAACTTTTCA  GTTAAGTATG   7260

AACAAGAAAC  AAAATTTTTA  CGCAGCCATT  ATTGTGGCTA  TTTTTCTTTG  TTTGCAATTG   7320

TCTCATGGCT  CTTCAGGTGT  CAGCTTTGAA  AAAACCCCTG  CTATTAAAAT  TGTAGGAAAC   7380

AAATTCTTTG  ACTCTGAGAG  TGGGGAACAG  TTCTTCATCA  AGGGCATTGC  TTACCAATTG   7440

CAGAGAAGTG  AAGAGGAGCT  TAGCAATGCA  AATGGGGCTT  TTGAGACAAG  TTATATTGAT   7500

GCCTTAGCGG  ACCCAAAAAT  ATGCTTAAGA  GATATTCCAT  TTTTGAAAAT  GCTAGGAGTG   7560

AACACACTGC  GTGTTTATGC  AATAGATCCG  ACAAAATCAC  ATGATATATG  TATGGAAGCT   7620

CTATCTGCCG  AAGGAATGTA  CGTCCTATTA  GATCT                                7655
```

(2) INFORMATION FOR SEQ ID NO:2:

(i) SEQUENCE CHARACTERISTICS:
    (A) LENGTH: 1876 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:2:

```
Met  Asn  Thr  Asp  Gln  Gln  Pro  Tyr  Gln  Gly  Gln  Thr  Asp  Tyr  Thr  Gln
  1                 5                  10                         15

Gly  Pro  Gly  Asn  Gly  Gln  Ser  Gln  Glu  Gln  Asp  Tyr  Asp  Tyr  Gly
             20                 25                     30

Gln  Pro  Leu  Tyr  Pro  Ser  Gln  Ala  Asp  Gly  Tyr  Tyr  Asp  Pro  Asn  Val
             35                      40                    45

Ala  Ala  Gly  Thr  Glu  Ala  Asp  Met  Tyr  Gly  Gln  Pro  Pro  Asn  Glu
        50                      55                    60

Ser  Tyr  Asp  Gln  Asp  Tyr  Thr  Asn  Gly  Glu  Tyr  Tyr  Gly  Gln  Pro  Pro
 65                      70                   75                      80

Asn  Met  Ala  Ala  Gln  Asp  Gly  Glu  Asn  Phe  Ser  Asp  Phe  Ser  Ser  Tyr
                     85                   90                   95

Gly  Pro  Pro  Gly  Thr  Pro  Gly  Tyr  Asp  Ser  Tyr  Gly  Gly  Gln  Tyr  Thr
              100                 105                    110

Ala  Ser  Gln  Met  Ser  Tyr  Gly  Glu  Pro  Asn  Ser  Ser  Gly  Thr  Ser  Thr
              115                 120                    125

Pro  Ile  Tyr  Gly  Asn  Tyr  Asp  Pro  Asn  Ala  Ile  Ala  Met  Ala  Leu  Pro
              130                 135                    140

Asn  Glu  Pro  Tyr  Pro  Ala  Trp  Thr  Ala  Asp  Ser  Gln  Ser  Pro  Val  Ser
145                  150                 155                    160
```

```
Ile Glu Gln Ile Glu Asp Ile Phe Ile Asp Leu Thr Asn Arg Leu Gly
            165                 170                 175

Phe Gln Arg Asp Ser Met Arg Asn Met Phe Asp His Phe Met Val Leu
            180                 185                 190

Leu Asp Ser Arg Ser Ser Arg Met Ser Pro Asp Gln Ala Leu Leu Ser
            195                 200                 205

Leu His Ala Asp Tyr Ile Gly Gly Asp Thr Ala Asn Tyr Lys Lys Trp
            210                 215                 220

Tyr Phe Ala Ala Gln Leu Asp Met Asp Asp Glu Ile Gly Phe Arg Asn
225                 230                 235                 240

Met Ser Leu Gly Lys Leu Ser Arg Lys Ala Arg Lys Ala Lys Lys Lys
                    245                 250                 255

Asn Lys Lys Ala Met Glu Glu Ala Asn Pro Glu Asp Thr Glu Glu Thr
            260                 265                 270

Leu Asn Lys Ile Glu Gly Asp Asn Ser Leu Glu Ala Ala Asp Phe Arg
            275                 280                 285

Trp Lys Ala Lys Met Asn Gln Leu Ser Pro Leu Glu Arg Val Arg His
            290                 295                 300

Ile Ala Leu Tyr Leu Leu Cys Trp Gly Glu Ala Asn Gln Val Arg Phe
305                 310                 315                 320

Thr Ala Glu Cys Leu Cys Phe Ile Tyr Lys Cys Ala Leu Asp Tyr Leu
                    325                 330                 335

Asp Ser Pro Leu Cys Gln Gln Arg Gln Glu Pro Met Pro Glu Gly Asp
            340                 345                 350

Phe Leu Asn Arg Val Ile Thr Pro Ile Tyr His Phe Ile Arg Asn Gln
            355                 360                 365

Val Tyr Glu Ile Val Asp Gly Arg Phe Val Lys Arg Glu Arg Asp His
            370                 375                 380

Asn Lys Ile Val Gly Tyr Asp Asp Leu Asn Gln Leu Phe Trp Tyr Pro
385                 390                 395                 400

Glu Gly Ile Ala Lys Ile Val Leu Glu Asp Gly Thr Lys Leu Ile Glu
                    405                 410                 415

Leu Pro Leu Glu Glu Arg Tyr Leu Arg Leu Gly Asp Val Val Trp Asp
            420                 425                 430

Asp Val Phe Phe Lys Thr Tyr Lys Glu Thr Arg Thr Trp Leu His Leu
            435                 440                 445

Val Thr Asn Phe Asn Arg Ile Trp Val Met His Ile Ser Ile Phe Trp
    450                 455                 460

Met Tyr Phe Ala Tyr Asn Ser Pro Thr Phe Tyr Thr His Asn Tyr Gln
465                 470                 475                 480

Gln Leu Val Asp Asn Gln Pro Leu Ala Ala Tyr Lys Trp Ala Ser Cys
                485                 490                 495

Ala Leu Gly Gly Thr Val Ala Ser Leu Ile Gln Ile Val Ala Thr Leu
            500                 505                 510

Cys Glu Trp Ser Phe Val Pro Arg Lys Trp Ala Gly Ala Gln His Leu
            515                 520                 525

Ser Arg Arg Phe Trp Phe Leu Cys Ile Ile Phe Gly Ile Asn Leu Gly
    530                 535                 540

Pro Ile Ile Phe Val Phe Ala Tyr Asp Lys Asp Thr Val Tyr Ser Thr
545                 550                 555                 560

Ala Ala His Val Val Ala Ala Val Met Phe Phe Val Ala Val Ala Thr
                565                 570                 575

Ile Ile Phe Phe Ser Ile Met Pro Leu Gly Gly Leu Phe Thr Ser Tyr
            580                 585                 590
```

Met Lys Lys Ser Thr Arg Arg Tyr Val Ala Ser Gln Thr Phe Thr Ala
             595                 600                 605

Ala Phe Ala Pro Leu His Gly Leu Asp Arg Trp Met Ser Tyr Leu Val
         610                 615                 620

Trp Val Thr Val Phe Ala Ala Lys Tyr Ser Glu Ser Tyr Tyr Phe Leu
625                     630                 635                 640

Val Leu Ser Leu Arg Asp Pro Ile Arg Ile Leu Ser Thr Thr Ala Met
                 645                 650                     655

Arg Cys Thr Gly Glu Tyr Trp Trp Gly Ala Val Leu Cys Lys Val Gln
             660                 665                 670

Pro Lys Ile Val Leu Gly Leu Val Ile Ala Thr Asp Phe Ile Leu Phe
         675                 680                 685

Phe Leu Asp Thr Tyr Leu Trp Tyr Ile Ile Val Asn Thr Ile Phe Ser
     690                 695                 700

Val Gly Lys Ser Phe Tyr Leu Gly Ile Ser Ile Leu Thr Pro Trp Arg
705                     710                 715                 720

Asn Ile Phe Thr Arg Leu Pro Lys Arg Ile Tyr Ser Lys Ile Leu Ala
                 725                 730                 735

Thr Thr Asp Met Glu Ile Lys Tyr Lys Pro Lys Val Leu Ile Ser Gln
             740                 745                 750

Val Trp Asn Ala Ile Ile Ile Ser Met Tyr Arg Glu His Leu Leu Ala
         755                 760                 765

Ile Asp His Val Gln Lys Leu Leu Tyr His Gln Val Pro Ser Glu Ile
     770                 775                 780

Glu Gly Lys Arg Thr Leu Arg Ala Pro Thr Phe Phe Val Ser Gln Asp
785                     790                 795                 800

Asp Asn Asn Phe Glu Thr Glu Phe Phe Pro Arg Asp Ser Glu Ala Glu
                 805                 810                 815

Arg Arg Ile Ser Phe Phe Ala Gln Ser Leu Ser Thr Pro Ile Pro Glu
             820                 825                 830

Pro Leu Pro Val Asp Asn Met Pro Thr Phe Thr Val Leu Thr Pro His
         835                 840                 845

Tyr Ala Glu Arg Ile Leu Leu Ser Leu Arg Glu Ile Ile Arg Glu Asp
     850                 855                 860

Asp Gln Phe Ser Arg Val Thr Leu Leu Glu Tyr Leu Lys Gln Leu His
865                     870                 875                 880

Pro Val Glu Trp Glu Cys Phe Val Lys Asp Thr Lys Ile Leu Ala Glu
                 885                 890                 895

Glu Thr Ala Ala Tyr Glu Gly Asn Glu Asn Glu Ala Glu Lys Glu Asp
             900                 905                 910

Ala Leu Lys Ser Gln Ile Asp Asp Leu Pro Phe Tyr Cys Ile Gly Phe
         915                 920                 925

Lys Ser Ala Ala Pro Glu Tyr Thr Leu Arg Thr Arg Ile Trp Ala Ser
     930                 935                 940

Leu Arg Ser Gln Thr Leu Tyr Arg Thr Ile Ser Gly Phe Met Asn Tyr
945                     950                 955                 960

Ser Arg Ala Ile Lys Leu Leu Tyr Arg Val Glu Asn Pro Glu Ile Val
                 965                 970                 975

Gln Met Phe Gly Gly Asn Ala Glu Gly Leu Glu Arg Glu Leu Glu Lys
             980                 985                 990

Met Ala Arg Arg Lys Phe Lys Phe Leu Val Ser Met Gln Arg Leu Ala
         995                 1000                1005

-continued

```
Lys  Phe  Lys  Pro  His  Glu  Leu  Glu  Asn  Ala  Glu  Phe  Leu  Leu  Arg  Ala
     1010                1015                1020

Tyr  Pro  Asp  Leu  Gln  Ile  Ala  Tyr  Leu  Asp  Glu  Glu  Pro  Pro  Leu  Thr
1025                1030                1035                          1040

Glu  Gly  Glu  Glu  Pro  Arg  Ile  Tyr  Ser  Ala  Leu  Ile  Asp  Gly  His  Cys
               1045                1050                     1055

Glu  Ile  Leu  Asp  Asn  Gly  Arg  Arg  Pro  Lys  Phe  Arg  Val  Gln  Leu
     1060                1065                     1070

Ser  Gly  Asn  Pro  Ile  Leu  Gly  Asp  Gly  Lys  Ser  Asp  Asn  Gln  Asn  His
          1075                1080                     1085

Ala  Leu  Ile  Phe  Tyr  Arg  Gly  Glu  Tyr  Ile  Gln  Leu  Ile  Asp  Ala  Asn
     1090                1095                1100

Gln  Asp  Asn  Tyr  Leu  Glu  Glu  Cys  Leu  Lys  Ile  Arg  Ser  Val  Leu  Ala
1105                1110                1115                     1120

Glu  Phe  Glu  Glu  Leu  Asn  Val  Glu  Gln  Val  Asn  Pro  Tyr  Ala  Pro  Gly
               1125                1130                     1135

Leu  Arg  Tyr  Glu  Glu  Gln  Thr  Thr  Asn  His  Pro  Val  Ala  Ile  Val  Gly
          1140                1145                     1150

Ala  Arg  Glu  Tyr  Ile  Phe  Ser  Glu  Asn  Ser  Gly  Val  Leu  Gly  Asp  Val
     1155                1160                     1165

Ala  Ala  Gly  Lys  Glu  Gln  Thr  Phe  Gly  Thr  Leu  Phe  Ala  Arg  Thr  Leu
     1170                1175                1180

Ser  Gln  Ile  Gly  Gly  Lys  Leu  His  Tyr  Gly  His  Pro  Asp  Phe  Ile  Asn
1185                1190                1195                          1200

Ala  Thr  Phe  Met  Thr  Thr  Arg  Gly  Gly  Val  Ser  Lys  Ala  Gln  Lys  Gly
               1205                1210                     1215

Leu  His  Leu  Asn  Glu  Asp  Ile  Tyr  Ala  Gly  Met  Asn  Ala  Met  Leu  Arg
          1220                1225                     1230

Gly  Gly  Arg  Ile  Lys  His  Cys  Glu  Tyr  Tyr  Gln  Cys  Gly  Lys  Gly  Arg
          1235                1240                     1245

Asp  Leu  Gly  Phe  Gly  Thr  Ile  Leu  Asn  Phe  Thr  Thr  Lys  Ile  Gly  Ala
     1250                1255                1260

Gly  Met  Gly  Glu  Gln  Met  Leu  Ser  Arg  Glu  Tyr  Tyr  Tyr  Leu  Gly  Thr
1265                1270                1275                          1280

Gln  Leu  Pro  Val  Asp  Arg  Phe  Leu  Thr  Phe  Tyr  Tyr  Ala  His  Pro  Gly
               1285                1290                     1295

Phe  His  Leu  Asn  Asn  Leu  Phe  Ile  Gln  Leu  Ser  Leu  Gln  Met  Phe  Met
          1300                1305                     1310

Leu  Thr  Leu  Val  Asn  Leu  Ser  Ser  Leu  Ala  His  Glu  Ser  Ile  Met  Cys
     1315                1320                     1325

Ile  Tyr  Asp  Arg  Asn  Lys  Pro  Lys  Thr  Asp  Val  Leu  Val  Pro  Ile  Gly
     1330                1335                     1340

Cys  Tyr  Asn  Phe  Gln  Pro  Ala  Val  Asp  Trp  Val  Arg  Arg  Tyr  Thr  Leu
1345                1350                1355                          1360

Ser  Ile  Phe  Ile  Val  Phe  Trp  Ile  Ala  Phe  Val  Pro  Ile  Val  Val  Gln
          1365                1370                     1375

Glu  Leu  Ile  Glu  Arg  Gly  Leu  Trp  Lys  Ala  Thr  Gln  Arg  Phe  Phe  Cys
               1380                1385                     1390

His  Leu  Leu  Ser  Leu  Ser  Pro  Met  Phe  Glu  Val  Phe  Ala  Gly  Gln  Ile
          1395                1400                     1405

Tyr  Ser  Ser  Ala  Leu  Leu  Ser  Asp  Leu  Ala  Ile  Gly  Gly  Ala  Arg  Tyr
     1410                1415                     1420

Ile  Ser  Thr  Gly  Arg  Gly  Phe  Ala  Thr  Ser  Arg  Ile  Pro  Phe  Ser  Ile
1425                1430                1435                          1440
```

```
Leu Tyr Ser Arg Phe Ala Gly Ser Ala Ile Tyr Met Gly Ala Arg Ser
            1445                1450                1455
Met Leu Met Leu Leu Phe Gly Thr Val Ala His Trp Gln Ala Pro Leu
        1460                1465                1470
Leu Trp Phe Trp Ala Ser Leu Ser Ser Leu Ile Phe Ala Pro Phe Val
        1475                1480                1485
Phe Asn Pro His Gln Phe Ala Trp Glu Asp Phe Phe Leu Asp Tyr Arg
    1490                1495                1500
Asp Tyr Ile Arg Trp Leu Ser Arg Gly Asn Asn Gln Tyr His Arg Asn
505                1510                1515                1520
Ser Trp Ile Gly Tyr Val Arg Met Ser Arg Ala Arg Ile Thr Gly Phe
            1525                1530                1535
Lys Arg Lys Leu Val Gly Asp Glu Ser Glu Lys Ala Ala Gly Asp Ala
            1540                1545                1550
Ser Arg Ala His Arg Thr Asn Leu Ile Met Ala Glu Ile Ile Pro Cys
        1555                1560                1565
Ala Ile Tyr Ala Ala Gly Cys Phe Ile Ala Phe Thr Phe Ile Asn Ala
        1570                1575                1580
Gln Thr Gly Val Lys Thr Thr Asp Asp Asp Arg Val Asn Ser Val Leu
585                1590                1595                1600
Arg Ile Ile Ile Cys Thr Leu Ala Pro Ile Ala Val Asn Leu Gly Val
            1605                1610                1615
Leu Phe Phe Cys Met Gly Met Ser Cys Cys Ser Gly Pro Leu Phe Gly
        1620                1625                1630
Met Cys Cys Lys Lys Thr Gly Ser Val Met Ala Gly Ile Ala His Gly
        1635                1640                1645
Val Ala Val Ile Val His Ile Ala Phe Phe Ile Val Met Trp Val Leu
    1650                1655                1660
Glu Ser Phe Asn Phe Val Arg Met Leu Ile Gly Val Val Thr Cys Ile
665                1670                1675                1680
Gln Cys Gln Arg Leu Ile Phe His Cys Met Thr Ala Leu Met Leu Thr
                1685                1690                1695
Arg Glu Phe Lys Asn Asp His Ala Asn Thr Ala Phe Trp Thr Gly Lys
        1700                1705                1710
Trp Tyr Gly Lys Gly Met Gly Tyr Met Ala Trp Thr Gln Pro Ser Arg
        1715                1720                1725
Glu Leu Thr Ala Lys Val Ile Glu Leu Ser Glu Phe Ala Ala Asp Phe
        1730                1735                1740
Val Leu Gly His Val Ile Leu Ile Cys Gln Leu Pro Leu Ile Ile Ile
745                1750                1755                1760
Pro Lys Ile Asp Lys Phe His Ser Ile Met Leu Phe Trp Leu Lys Pro
            1765                1770                1775
Ser Arg Gln Ile Arg Pro Pro Ile Tyr Ser Leu Lys Gln Thr Arg Leu
            1780                1785                1790
Arg Lys Arg Met Val Lys Lys Tyr Cys Ser Leu Tyr Phe Leu Val Leu
            1795                1800                1805
Ala Ile Phe Ala Gly Cys Ile Ile Gly Pro Ala Val Ala Ser Ala Lys
        1810                1815                1820
Ile His Lys His Ile Gly Asp Ser Leu Asp Gly Val Val His Asn Leu
825                1830                1835                1840
Phe Gln Pro Ile Asn Thr Thr Asn Asn Asp Thr Gly Ser Gln Met Ser
            1845                1850                1855
```

Thr Tyr Gln Ser His Tyr Tyr Thr His Thr Pro Ser Leu Lys Thr Trp
                1860                1865                1870
Ser Thr Ile Lys
     1875

( 2 ) INFORMATION FOR SEQ ID NO:3:

( i ) SEQUENCE CHARACTERISTICS:
         ( A ) LENGTH: 7070 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| GAATTCCCCT | CGCAACACTG | AAAGATGCCA | TTGTCAAAGG | TGAAATTGCC | GCGTGGCCCC | 60 |
| TAGATCCTGC | TCGTGAACGA | TGGACGCGGC | CTGCGCTATT | CATCAGGGCT | ACTCAATCGC | 120 |
| ATTATGTGGT | AGACGAGTAT | CTTCCGATCA | TCGGCGCGTT | CTTTCCACGC | TTTGAAACAC | 180 |
| GTGACATCGA | TGCGGGTCAC | TGGGTAAATG | CGGAGAAGCC | TGGGGAATGT | GCCGAAAGCA | 240 |
| TCGTCGATTT | TGTGGAGCGG | CACGAGGATT | AAAGGCAAGC | GCCCCGGAGC | AAGGTGCCAG | 300 |
| TAGCACCAGT | CGGTGGCTGT | GCGCTTGCCG | TAGCACATGA | CATACGGACT | ATTGTGTGAG | 360 |
| TGGTGATGGG | GTGTAGGCAG | TGCCACACCA | GTTTAAAGGC | CTAGTAACGG | CAAATCGCCA | 420 |
| AAAGAGATGA | TGCTGATGCA | TACGATAAGA | TCGTCAGTTT | CACGTTCGCG | GTTCGAACAT | 480 |
| GGAATTGTGG | CTAAAGAAAT | TTGGGCGGTA | TGATGCAAAT | GAGGTGTACG | TATGTATATA | 540 |
| TAGCAAAGAG | TAGAATAAAA | TGAGATAAAG | CCTCGTTCGT | TCTCTCCATT | TCTTCCCTGT | 600 |
| TTCTCCTTTA | TTTTCTCTAC | TGCTTATTTC | GAGTTCACCA | GAGAACAAGA | GAGCAGGAAC | 660 |
| GCAAAGAGTG | TGTGACACGA | AATTCAAGAT | ACAAAATAA | AGCTTACGT | TGTGTATTTC | 720 |
| AACTGGTGTG | CTAAGAATAG | AGTTTCATAA | AGTACTGCAT | TTATTCATAT | ATTATTTTTG | 780 |
| TTATTTGTAT | ATATACTTCA | CACTTAGAGT | TCTACTAAAA | GTCTACCCAG | CACGCATCCT | 840 |
| TCGTTTATTT | TTACATCTCT | CTTTTGCTTT | TCCTTTTTTT | TTTTGGTGCT | TGCTAGATAC | 900 |
| TACTGAAGAT | CAAAGGTTAC | AAAGAACGCC | GCATATATTT | TCTGCAGGCA | TATTAAAGAA | 960 |
| GTTACAAAAG | GATTAATCGA | AGCGCTGTTT | GGATACACTC | CTGTAAAGAG | AAGAAAGGA | 1020 |
| AAAAAATAAA | AAGTGGACAA | TAAATAATTA | TTAAACTGTC | ATAGTTATGT | CCTACAACGA | 1080 |
| TCCAAACTTG | AATGGACAGT | ATTACAGTAA | CGGTGATGGG | ACTGGTGACG | GTAATTACCC | 1140 |
| TACGTACCAA | GTGACACAGG | ATCAAAGTGC | GTACGATGAG | TACGGTCAGC | CAATCTATAC | 1200 |
| ACAAAACCAA | CTGGATGATG | GTTATTATGA | TCCAAACGAA | CAATACGTTG | ACGGTACACA | 1260 |
| ATTTCCTCAG | GGACAAGATC | CTTCACAAGA | CCAAGGTCCT | TATAATAACG | ATGCTAGTTA | 1320 |
| CTATAACCAA | CCCCCCAATA | TGATGAACCC | GTCTTCTCAA | GATGGAGAGA | ACTTCTCAGA | 1380 |
| TTTTAGCAGC | TATGGTCCCC | CATCCGGCAC | TTATCCTAAC | GATCAATATA | CTCCTTCTCA | 1440 |
| AATGAGTTAT | CCTGATCAAG | ATGGTTCTTC | AGGGGCCTCA | ACCCCTATG | GAAATGGTGT | 1500 |
| CGTTAATGGT | AATGGCCAGT | ACTACGACCC | TAATGCTATT | GAAATGGCTT | TACCAAATGA | 1560 |
| TCCATATCCC | GCATGGACCG | CAGATCCCCA | GTCTCCCCTG | CCCATCGAAC | AAATCGAAGA | 1620 |
| TATCTTCATA | GATTTAACAA | ATAAATTCGG | TTTTCAGAGA | GATTCCATGA | GAAATATGTT | 1680 |
| TGACCATTTT | ATGACCCTTT | TGGACTCTAG | ATCTTCTAGG | ATGTCTCCAG | AACAGGCCCT | 1740 |
| TTTATCATTA | CATGCAGACT | ACATAGGTGG | AGATACGGCC | AACTACAAAA | AATGGTACTT | 1800 |
| TGCCGCTCAA | CTTGATATGG | ATGATGAAAT | TGGTTTCAGG | AATATGAAGT | TGGGTAAGCT | 1860 |

-continued

| | | | | | |
|---|---|---|---|---|---|
| ATCAAGAAAG | GCAAGAAAGG | CTAAGAAGAA | AAATAAAAAA | GCCATGCAAG | AGGCTAGTCC 1920 |
| TGAAGACACT | GAGGAGACTT | TAAATCAAAT | TGAGGGTGAT | AACTCATTAG | AAGCTGCGGA 1980 |
| TTTTAGATGG | AAGTCAAAGA | TGAATCAACT | TTCTCCATTT | GAAATGGTTC | GTCAAATTGC 2040 |
| CTTGTTTTTA | TTATGTTGGG | GCGAGGCAAA | TCAAGTCAGA | TTTACCCCGG | AGTGTCTTTG 2100 |
| TTTCATTTAT | AAATGCGCCT | CTGATTACTT | AGATTCTGCA | CAATGTCAAC | AACGTCCTGA 2160 |
| TCCCTTGCCT | GAAGGTGATT | TTTTGAATAG | AGTTATTACT | CCTCTTTATC | GTTTATTAG 2220 |
| GAGCCAGGTT | TACGAAATCG | TGGATGGTCG | ATACGTGAAG | AGTGAAAAG | ATCATAACAA 2280 |
| AGTTATTGGG | TATGATGATG | TCAATCAATT | ATTCTGGTAT | CCAGAAGGTA | TAGCAAAAAT 2340 |
| TGTCATGGAA | GATGGAACCA | GGTTGATTGA | TTTGCCAGCA | GAGGAGCGTT | ATTTGAAATT 2400 |
| GGGAGAAATT | CCCTGGGATG | ATGTCTTCTT | TAAAACTTAC | AAAGAAACAC | GTTCCTGGTT 2460 |
| ACATTTAGTT | ACCAACTTCA | ATCGTATTTG | GATCATGCAC | ATCTCAGTAT | ATTGGATGTA 2520 |
| TTGTGCTTAC | AATGCTCCAA | CTTTTTATAC | TCACAACTAT | CAACAATTGG | TCGACAATCA 2580 |
| GCCTTTGGCA | GCTTATAAAT | GGGCCACTGC | AGCATTAGGT | GGTACTGTGG | CAAGTTTGAT 2640 |
| TCAAGTTGCC | GCTACTTTGT | GCGAGTGGTC | ATTCGTTCCT | AGAAAATGGG | CGGGTGCTCA 2700 |
| ACATTTGTCC | CGTAGATTCT | GGTTCTTGTG | TGTCATTATG | GGTATTAATT | TGGGGCCTGT 2760 |
| GATATTTGTT | TTCGCTTATG | ATAAGGACAC | AGTATATTCT | ACTGCCGCTC | ATGTCGTTGG 2820 |
| AGCAGTTATG | TTTTTTGTTG | CTGTGGCAAC | ACTTGTTTTC | TTTTCCGTAA | TGCCATTGGG 2880 |
| TGGATTATTT | ACATCGTATA | TGAAAAAGTC | CACAAGAAGT | TATGTTGCCT | CACAGACCTT 2940 |
| CACCGCATCT | TTTGCTCCAT | TGCATGGTTT | AGACAGGTGG | ATGTCTTATT | TGGTTTGGGT 3000 |
| AACCGTTTTT | GCTGCTAAAT | ATGCAGAGTC | ATATTTTTT | CTAATACTGT | CACTAAGAGA 3060 |
| TCCAATTAGG | ATTTTATCTA | CTACATCAAT | GAGATGTACT | GGTGAATACT | GGTGGGGTAA 3120 |
| TAAGATTTGT | AAGGTCCAGC | CAAAGATTGT | TTTAGGTTTA | ATGATTGCGA | CTGACTTCAT 3180 |
| TTTGTTCTTT | TTGGATACCT | ACTTGTGGTA | TATCGTTGTT | AACACTGTTT | TCTCGGTCGG 3240 |
| AAAATCGTTC | TATTTGGGTA | TTTCTATCTT | AACTCCATGG | AGAAATATTT | TCACTAGATT 3300 |
| GCCAAAAAGA | ATTTATTCTA | AGATCTTGGC | TACTACTGAT | ATGGAAATAA | AATATAAACC 3360 |
| GAAAGTACTA | ATTTCTCAGA | TTTGGAATGC | TATCATTATC | TCCATGTACA | GAGAACATTT 3420 |
| ATTAGCCATA | GACCATGTAC | AAAAATTGTT | ATATCATCAG | GTTCCGTCCG | AAATTGAAGG 3480 |
| TAAGAGGACT | TTGAGAGCAC | CAACTTTCTT | TGTTTCCCAA | GATGACAATA | ATTTTGAGAC 3540 |
| TGAATTTTTC | CCTAGAGATT | CAGAAGCTGA | GCGCCGTATT | TCATTTTTTG | CCCAATCTCT 3600 |
| ATCCACTCCA | ATTCCAGAAC | CACTACCAGT | TGACAACATG | CCAACATTTA | CTGTATTAAC 3660 |
| TCCCCATTAC | GCCGAGAGGA | TTCTATTATC | ATTGAGAGAA | ATTATTCGTG | AAGATGATCA 3720 |
| ATTTTCAAGA | GTTACTCTTT | TGGAATACCT | GAAGCAATTA | CACCCGGTAG | AATGGGACTG 3780 |
| TTTTGTTAAG | GATACGAAAA | TTCTTGCTGA | AGAAACGGCC | GCATATGAAA | ACAATGAAGA 3840 |
| TGAACCTGAA | AAGGAAGACG | CTCTGAAATC | TCAAATTGAT | GATTTACCTT | TCTATTGTAT 3900 |
| TGGTTTCAAA | TCTGCTGCAC | CAGAATACAC | CTTACGTACG | AGAATCTGGG | CCTCTTTAAG 3960 |
| GTCGCAAACT | TTGTATCGCA | CAATCTCGGG | GTTTATGAAT | TATTCGAGGG | CCATAAAATT 4020 |
| ACTTTATCGT | GTGGAAAATC | CAGAAATCGT | TCAAATGTTC | GGTGGTAATG | CTGATGGATT 4080 |
| AGAAAGAGAA | CTGGAAAAAA | TGGCAAGGCG | AAAATTCAAA | TTCTTGGTTT | CGATGCAAAG 4140 |
| ATTGGCCAAG | TTTAAACCAC | ATGAACTAGA | AAATGCTGAG | TTCCTGTTGA | GAGCTTATCC 4200 |
| GGACTTGCAA | ATTGCCTACC | TGGATGAAGA | ACCTCCCTTA | AACGAAGGCG | AAGAGCCAAG 4260 |

-continued

| | | | | | |
|---|---|---|---|---|---|
| AATTTACTCG | GCCTTAATTG | ATGGTCATTG | TGAGATTTTA | GAGAATGGTC | GTAGACGTCC | 4320
| CAAATTTAGA | GTTCAACTAT | CCGGTAATCC | AATTCTTGGT | GATGGTAAAT | CAGATAATCA | 4380
| AAATCATGCT | TTGATTTTTT | ACAGAGGTGA | GTATATTCAA | TTGATTGATG | CTAATCAAGA | 4440
| CAATTACTTG | GAAGAGTGTT | TGAAAATCAG | GTCTGTCTTA | GCAGAATTTG | AAGAATTGGG | 4500
| AATTGAGCAA | ATTCATCCTT | ATACTCCTGG | TTTAAAATAT | GAGGACCAAT | CCACAAATCA | 4560
| TCCTGTTGCA | ATTGTCGGCG | CTAGAGAATA | TATTTTCTCA | GAAAACTCTG | GTGTTCTTGG | 4620
| TGATGTAGCG | GCTGGTAAAG | AACAAACTTT | TGGTACATTA | TTTGCCCGTA | CTTTGGCACA | 4680
| GATTGGTGGT | AAATTGCATT | ATGGTCATCC | AGATTTTATT | AATGCGACAT | TCATGACTAC | 4740
| TAGGGGTGGT | GTTTCCAAAG | CACAAAAGGG | TCTACATTTA | AATGAAGATA | TTTATGCCGG | 4800
| TATGAATGCC | GTACTTCGGG | GTGGTCGTAT | CAAGCATTGC | GAATATTATC | AGTGTGGTAA | 4860
| AGGTAGAGAT | TTAGGTTTTG | GTACAATTTT | GAATTTCACT | ACTAAGATCG | GTGCTGGTAT | 4920
| GGGTGAACAA | ATGTTATCTC | GTGAATACTA | TTATTTGGGT | ACGCAATTAC | CTATTGACCG | 4980
| TTTTTTAACA | TTTTATTATG | CGCATCCAGG | GTTTCACTTG | AATAACTTAT | TTATTCAATT | 5040
| GTCTCTGCAG | ATGTTCATGT | TAACTTTAGT | GAACTTGCAT | GCTTTGGCTC | ATGAATCCAT | 5100
| TCTGTGTGTT | TACGATAGGG | ATAAGCCAAT | TACTGATGTT | TTGTATCCAA | TGGTTGTTA | 5160
| CAACTTTCAT | CCTGCGATTG | ATTGGGTGAG | ACGTTATACA | CTCTCTATTT | TCATCGTCTT | 5220
| TTGGATTGCT | TTTGTCCCTA | TTGTCGTTCA | GGAATTAATC | GAGCGTGGTC | TGTGGAAGGC | 5280
| GACACAAAGA | TTTTTCCGTC | ACATTTATC | TCTATCTCCA | ATGTTTGAAG | TCTTTGCTGG | 5340
| CCAAATCTAT | TCTTCAGCAC | TGTTAAGTGA | TATCGCTGTG | GGTGGTGCTC | GTTATATTTC | 5400
| AACAGGTCGT | GGCTTTGCTA | CATCTCGTAT | ACCTTTCTCT | ATTCTTTATT | CAAGATTTGC | 5460
| GGGTTCAGCC | ATTTATATGG | GATCAAGATC | AATGTTGATG | TTATTATTTG | GTACCGTGGC | 5520
| ACATTGGCAA | GCTCCACTAT | TATGGTTTTG | GGCATCATTA | TCAGCCTTAA | TCTTTGCACC | 5580
| ATTCATTTTC | AATCCACATC | AATTTGCTTG | GAAGATTTT | TTCCTAGACT | ACAGAGATTA | 5640
| TATCAGATGG | CTGTCAAGAG | GTAATAATAA | GTACCACAGG | AACTCATGGA | TTGGTTATGT | 5700
| AAGAATGTCG | AGGTCTCGTG | TTACTGGTTT | CAAGCGCAAA | CTGGTGGGTG | ATGAGTCTGA | 5760
| AAAATCTGCA | GGCGATGCAA | GCAGGGCTCA | TAGAACCAAT | TTAATTATGG | CTGAAATTAT | 5820
| ACCGTGTGCG | ATTTACGCAG | CAGGTTGTTT | TATTGCCTTC | ACGTTTATTA | ATGCACAAAC | 5880
| TGGTGTCAAG | ACTACTGATG | AAGATAGAGT | AAATTCCACC | TTACGTATCA | TCATTTGCAC | 5940
| CTTGGCGCCT | ATTGTTATCG | ATATTGGTGT | TTTATTCTTC | TGTATGGGTT | TGTCATGCTG | 6000
| CTCTGGCCCT | TTGTTGGGCA | TGTGCTGCAA | GAAAACTGGT | TCTGTTATGG | CAGGGATCGC | 6060
| TCACGGTATC | GCTGTTGTTG | TCCATATTGT | CTTTTTCATT | GTCATGTGGG | TTTTAGAGGG | 6120
| TTTTAGTTTT | GTTAGGATGT | TGATTGGCGT | TGTTACATGT | ATACAATGTC | AAAGGTTGAT | 6180
| TTTTCACTGT | ATGACTGTAC | TGTTGCTGAC | CCGTGAGTTC | AAGAATGATC | ACGCTAATAC | 6240
| TGCCTTTTGG | ACAGGCAAAT | GGTACAGCAC | CGGTTTAGGA | TATATGGCAT | GGACTCAACC | 6300
| GACAAGGGAA | TTGACTGCAA | AAGTCATTGA | GCTTTCCGAG | TTTGCAGCGG | ATTTTGTTTT | 6360
| GGGGCATGTA | ATTTTGATCT | TCCAACTACC | AGTCATTTGT | ATTCCAAAGA | TAGATAAGTT | 6420
| TCACTCCATC | ATGTTATTTT | GGTTAAAACC | ATCCCGTCAA | ATCCGTCCTC | CTATTTACTC | 6480
| TTTGAAACAA | GCACGCCTAC | GTAAACGTAT | GGTTAGGAGG | TATTGCAGCT | TGTACTTTTT | 6540
| GGTACTGATC | ATATTCGCGG | GATGCATCGT | TGGCCCTGCC | GTTGCTTCAG | CACATGTTCC | 6600
| AAAAGACCTT | GGATCTGGGT | TGACGGGTAC | TTTCCATAAC | TTGGTTCAAC | CAAGGAACGT | 6660

```
ATCTAACAAT GATACAGGGT CCCAGATGTC TACTTATAAG AGTCATTATT ACACTCATAC      6720

GCCATCCTTA AAGACCTGGT CTACGATCAA ATGATTTTTT TAGTTTACAA TCTATTTTTG      6780

TTTCTAAGCA AGTTTATCAC GCAAATACAT AAGTATATTT TTACTTTCTA TTCTTCCTAG      6840

TTTATATTTA TTTCATTGTA ACTTTCTTAG AAGCTCGGTC CTCTCGCTAT ATAGTAGGAT      6900

CTGCAACATA TTTGGATGTG GGTGGGCGTT CTCCTTCTTT TTTAGATGTA AGGTCCAACA      6960

CGTATAACAG GTGATACACA TAGAAAGACA CGTGGAAATA ACAGTCATTT ACGAATATTT      7020

AAAACCTGAG CAACTCCGTC AAATTTGATC TTAATCTTTT CTGGGGCCCC                 7070
```

( 2 ) INFORMATION FOR SEQ ID NO:4:

( i ) SEQUENCE CHARACTERISTICS:
        ( A ) LENGTH: 1895 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

```
Met Ser Tyr Asn Asp Pro Asn Leu Asn Gly Gln Tyr Tyr Ser Asn Gly
 1           5                  10                  15

Asp Gly Thr Gly Asp Gly Asn Tyr Pro Thr Tyr Gln Val Thr Gln Asp
            20                  25                  30

Gln Ser Ala Tyr Asp Glu Tyr Gly Gln Pro Ile Tyr Thr Gln Asn Gln
            35                  40                  45

Leu Asp Asp Gly Tyr Tyr Asp Pro Asn Glu Gln Tyr Val Asp Gly Thr
            50                  55                  60

Gln Phe Pro Gln Gly Gln Asp Pro Ser Gln Asp Gln Gly Pro Tyr Asn
65                  70                  75                  80

Asn Asp Ala Ser Tyr Tyr Asn Gln Pro Pro Asn Met Met Asn Pro Ser
                85                  90                  95

Ser Gln Asp Gly Glu Asn Phe Ser Asp Phe Ser Ser Tyr Gly Pro Pro
            100                 105                 110

Ser Gly Thr Tyr Pro Asn Asp Gln Tyr Thr Pro Ser Gln Met Ser Tyr
            115                 120                 125

Pro Asp Gln Asp Gly Ser Ser Gly Ala Ser Thr Pro Tyr Gly Asn Gly
            130                 135                 140

Val Val Asn Gly Asn Gly Gln Tyr Tyr Asp Pro Asn Ala Ile Glu Met
145                 150                 155                 160

Ala Leu Pro Asn Asp Pro Tyr Pro Ala Trp Thr Ala Asp Pro Gln Ser
                165                 170                 175

Pro Leu Pro Ile Glu Gln Ile Glu Asp Ile Phe Ile Asp Leu Thr Asn
            180                 185                 190

Lys Phe Gly Phe Gln Arg Asp Ser Met Arg Asn Met Phe Asp His Phe
            195                 200                 205

Met Thr Leu Leu Asp Ser Arg Ser Ser Arg Met Ser Pro Glu Gln Ala
            210                 215                 220

Leu Leu Ser Leu His Ala Asp Tyr Ile Gly Gly Asp Thr Ala Asn Tyr
225                 230                 235                 240

Lys Lys Trp Tyr Phe Ala Ala Gln Leu Asp Met Asp Asp Glu Ile Gly
                245                 250                 255

Phe Arg Asn Met Lys Leu Gly Lys Leu Ser Arg Lys Ala Arg Lys Ala
                260                 265                 270
```

```
Lys  Lys  Lys  Asn  Lys  Lys  Ala  Met  Gln  Glu  Ala  Ser  Pro  Glu  Asp  Thr
          275            280                 285

Glu  Glu  Thr  Leu  Asn  Gln  Ile  Glu  Gly  Asp  Asn  Ser  Leu  Glu  Ala  Ala
     290            295                 300

Asp  Phe  Arg  Trp  Lys  Ser  Lys  Met  Asn  Gln  Leu  Ser  Pro  Phe  Glu  Met
305            310                 315                                   320

Val  Arg  Gln  Ile  Ala  Leu  Phe  Leu  Leu  Cys  Trp  Gly  Glu  Ala  Asn  Gln
               325                 330                           335

Val  Arg  Phe  Thr  Pro  Glu  Cys  Leu  Cys  Phe  Ile  Tyr  Lys  Cys  Ala  Ser
          340                 345                      350

Asp  Tyr  Leu  Asp  Ser  Ala  Gln  Cys  Gln  Gln  Arg  Pro  Asp  Pro  Leu  Pro
          355                 360                      365

Glu  Gly  Asp  Phe  Leu  Asn  Arg  Val  Ile  Thr  Pro  Leu  Tyr  Arg  Phe  Ile
     370                 375                      380

Arg  Ser  Gln  Val  Tyr  Glu  Ile  Val  Asp  Gly  Arg  Tyr  Val  Lys  Ser  Glu
385                 390                 395                                400

Lys  Asp  His  Asn  Lys  Val  Ile  Gly  Tyr  Asp  Asp  Val  Asn  Gln  Leu  Phe
               405                 410                      415

Trp  Tyr  Pro  Glu  Gly  Ile  Ala  Lys  Ile  Val  Met  Glu  Asp  Gly  Thr  Arg
               420                 425                      430

Leu  Ile  Asp  Leu  Pro  Ala  Glu  Glu  Arg  Tyr  Leu  Lys  Leu  Gly  Glu  Ile
          435                 440                      445

Pro  Trp  Asp  Asp  Val  Phe  Phe  Lys  Thr  Tyr  Lys  Glu  Thr  Arg  Ser  Trp
     450                 455                 460

Leu  His  Leu  Val  Thr  Asn  Phe  Asn  Arg  Ile  Trp  Ile  Met  His  Ile  Ser
465                 470                 475                           480

Val  Tyr  Trp  Met  Tyr  Cys  Ala  Tyr  Asn  Ala  Pro  Thr  Phe  Tyr  Thr  His
               485                 490                           495

Asn  Tyr  Gln  Gln  Leu  Val  Asp  Asn  Gln  Pro  Leu  Ala  Ala  Tyr  Lys  Trp
          500                 505                      510

Ala  Thr  Ala  Ala  Leu  Gly  Gly  Thr  Val  Ala  Ser  Leu  Ile  Gln  Val  Ala
          515                 520                      525

Ala  Thr  Leu  Cys  Glu  Trp  Ser  Phe  Val  Pro  Arg  Lys  Trp  Ala  Gly  Ala
     530                 535                      540

Gln  His  Leu  Ser  Arg  Arg  Phe  Trp  Phe  Leu  Cys  Val  Ile  Met  Gly  Ile
545                 550                 555                                560

Asn  Leu  Gly  Pro  Val  Ile  Phe  Val  Phe  Ala  Tyr  Asp  Lys  Asp  Thr  Val
               565                 570                      575

Tyr  Ser  Thr  Ala  Ala  His  Val  Val  Gly  Ala  Val  Met  Phe  Phe  Val  Ala
          580                 585                      590

Val  Ala  Thr  Leu  Val  Phe  Phe  Ser  Val  Met  Pro  Leu  Gly  Gly  Leu  Phe
     595                 600                      605

Thr  Ser  Tyr  Met  Lys  Lys  Ser  Thr  Arg  Ser  Tyr  Val  Ala  Ser  Gln  Thr
     610                 615                      620

Phe  Thr  Ala  Ser  Phe  Ala  Pro  Leu  His  Gly  Leu  Asp  Arg  Trp  Met  Ser
625                 630                 635                                640

Tyr  Leu  Val  Trp  Val  Thr  Val  Phe  Ala  Ala  Lys  Tyr  Ala  Glu  Ser  Tyr
               645                 650                      655

Phe  Phe  Leu  Ile  Leu  Ser  Leu  Arg  Asp  Pro  Ile  Arg  Ile  Leu  Ser  Thr
               660                 665                      670

Thr  Ser  Met  Arg  Cys  Thr  Gly  Glu  Tyr  Trp  Trp  Gly  Asn  Lys  Ile  Cys
          675                 680                      685

Lys  Val  Gln  Pro  Lys  Ile  Val  Leu  Gly  Leu  Met  Ile  Ala  Thr  Asp  Phe
     690                 695                      700
```

```
Ile Leu Phe Phe Leu Asp Thr Tyr Leu Trp Tyr Ile Val Val Asn Thr
705                 710                 715                 720

Val Phe Ser Val Gly Lys Ser Phe Tyr Leu Gly Ile Ser Ile Leu Thr
                725                 730                 735

Pro Trp Arg Asn Ile Phe Thr Arg Leu Pro Lys Arg Ile Tyr Ser Lys
            740                 745                 750

Ile Leu Ala Thr Thr Asp Met Glu Ile Lys Tyr Lys Pro Lys Val Leu
        755                 760                 765

Ile Ser Gln Ile Trp Asn Ala Ile Ile Ile Ser Met Tyr Arg Glu His
    770                 775                 780

Leu Leu Ala Ile Asp His Val Gln Lys Leu Leu Tyr His Gln Val Pro
785                 790                 795                 800

Ser Glu Ile Glu Gly Lys Arg Thr Leu Arg Ala Pro Thr Phe Phe Val
                805                 810                 815

Ser Gln Asp Asp Asn Asn Phe Glu Thr Glu Phe Phe Pro Arg Asp Ser
            820                 825                 830

Glu Ala Glu Arg Arg Ile Ser Phe Phe Ala Gln Ser Leu Ser Thr Pro
        835                 840                 845

Ile Pro Glu Pro Leu Pro Val Asp Asn Met Pro Thr Phe Thr Val Leu
    850                 855                 860

Thr Pro His Tyr Ala Glu Arg Ile Leu Leu Ser Leu Arg Glu Ile Ile
865                 870                 875                 880

Arg Glu Asp Asp Gln Phe Ser Arg Val Thr Leu Leu Glu Tyr Leu Lys
                885                 890                 895

Gln Leu His Pro Val Glu Trp Asp Cys Phe Val Lys Asp Thr Lys Ile
            900                 905                 910

Leu Ala Glu Glu Thr Ala Ala Tyr Glu Asn Asn Glu Asp Glu Pro Glu
        915                 920                 925

Lys Glu Asp Ala Leu Lys Ser Gln Ile Asp Asp Leu Pro Phe Tyr Cys
    930                 935                 940

Ile Gly Phe Lys Ser Ala Ala Pro Glu Tyr Thr Leu Arg Thr Arg Ile
945                 950                 955                 960

Trp Ala Ser Leu Arg Ser Gln Thr Leu Tyr Arg Thr Ile Ser Gly Phe
                965                 970                 975

Met Asn Tyr Ser Arg Ala Ile Lys Leu Leu Tyr Arg Val Glu Asn Pro
            980                 985                 990

Glu Ile Val Gln Met Phe Gly Gly Asn Ala Asp Gly Leu Glu Arg Glu
        995                 1000                1005

Leu Glu Lys Met Ala Arg Arg Lys Phe Lys Phe Leu Val Ser Met Gln
    1010                1015                1020

Arg Leu Ala Lys Phe Lys Pro His Glu Leu Glu Asn Ala Glu Phe Leu
025                 1030                1035                1040

Leu Arg Ala Tyr Pro Asp Leu Gln Ile Ala Tyr Leu Asp Glu Glu Pro
            1045                1050                1055

Pro Leu Asn Glu Gly Glu Glu Pro Arg Ile Tyr Ser Ala Leu Ile Asp
        1060                1065                1070

Gly His Cys Glu Ile Leu Glu Asn Gly Arg Arg Arg Pro Lys Phe Arg
    1075                1080                1085

Val Gln Leu Ser Gly Asn Pro Ile Leu Gly Asp Gly Lys Ser Asp Asn
    1090                1095                1100

Gln Asn His Ala Leu Ile Phe Tyr Arg Gly Glu Tyr Ile Gln Leu Ile
105                 1110                1115                1120
```

-continued

```
Asp  Ala  Asn  Gln  Asp  Asn  Tyr  Leu  Glu  Glu  Cys  Leu  Lys  Ile  Arg  Ser
              1125                     1130                      1135

Val  Leu  Ala  Glu  Phe  Glu  Glu  Leu  Gly  Ile  Glu  Gln  Ile  His  Pro  Tyr
              1140                     1145                      1150

Thr  Pro  Gly  Leu  Lys  Tyr  Glu  Asp  Gln  Ser  Thr  Asn  His  Pro  Val  Ala
              1155                     1160                      1165

Ile  Val  Gly  Ala  Arg  Glu  Tyr  Ile  Phe  Ser  Glu  Asn  Ser  Gly  Val  Leu
              1170                     1175                      1180

Gly  Asp  Val  Ala  Ala  Gly  Lys  Glu  Gln  Thr  Phe  Gly  Thr  Leu  Phe  Ala
185                  1190                     1195                      1200

Arg  Thr  Leu  Ala  Gln  Ile  Gly  Gly  Lys  Leu  His  Tyr  Gly  His  Pro  Asp
              1205                     1210                      1215

Phe  Ile  Asn  Ala  Thr  Phe  Met  Thr  Thr  Arg  Gly  Gly  Val  Ser  Lys  Ala
              1220                     1225                      1230

Gln  Lys  Gly  Leu  His  Leu  Asn  Glu  Asp  Ile  Tyr  Ala  Gly  Met  Asn  Ala
              1235                     1240                      1245

Val  Leu  Arg  Gly  Gly  Arg  Ile  Lys  His  Cys  Glu  Tyr  Tyr  Gln  Cys  Gly
              1250                     1255                      1260

Lys  Gly  Arg  Asp  Leu  Gly  Phe  Gly  Thr  Ile  Leu  Asn  Phe  Thr  Thr  Lys
265                  1270                     1275                      1280

Ile  Gly  Ala  Gly  Met  Gly  Glu  Gln  Met  Leu  Ser  Arg  Glu  Tyr  Tyr  Tyr
              1285                     1290                      1295

Leu  Gly  Thr  Gln  Leu  Pro  Ile  Asp  Arg  Phe  Leu  Thr  Phe  Tyr  Tyr  Ala
              1300                     1305                      1310

His  Pro  Gly  Phe  His  Leu  Asn  Asn  Leu  Phe  Ile  Gln  Leu  Ser  Leu  Gln
              1315                     1320                      1325

Met  Phe  Met  Leu  Thr  Leu  Val  Asn  Leu  His  Ala  Leu  Ala  His  Glu  Ser
              1330                     1335                      1340

Ile  Leu  Cys  Val  Tyr  Asp  Arg  Asp  Lys  Pro  Ile  Thr  Asp  Val  Leu  Tyr
345                  1350                     1355                      1360

Pro  Ile  Gly  Cys  Tyr  Asn  Phe  His  Pro  Ala  Ile  Asp  Trp  Val  Arg  Arg
              1365                     1370                      1375

Tyr  Thr  Leu  Ser  Ile  Phe  Ile  Val  Phe  Trp  Ile  Ala  Phe  Val  Pro  Ile
              1380                     1385                      1390

Val  Val  Gln  Glu  Leu  Ile  Glu  Arg  Gly  Leu  Trp  Lys  Ala  Thr  Gln  Arg
              1395                     1400                      1405

Phe  Phe  Arg  His  Ile  Leu  Ser  Leu  Ser  Pro  Met  Phe  Glu  Val  Phe  Ala
              1410                     1415                      1420

Gly  Gln  Ile  Tyr  Ser  Ser  Ala  Leu  Leu  Ser  Asp  Ile  Ala  Val  Gly  Gly
425                  1430                     1435                      1440

Ala  Arg  Tyr  Ile  Ser  Thr  Gly  Arg  Gly  Phe  Ala  Thr  Ser  Arg  Ile  Pro
              1445                     1450                      1455

Phe  Ser  Ile  Leu  Tyr  Ser  Arg  Phe  Ala  Gly  Ser  Ala  Ile  Tyr  Met  Gly
              1460                     1465                      1470

Ser  Arg  Ser  Met  Leu  Met  Leu  Leu  Phe  Gly  Thr  Val  Ala  His  Trp  Gln
              1475                     1480                      1485

Ala  Pro  Leu  Leu  Trp  Phe  Trp  Ala  Ser  Leu  Ser  Ala  Leu  Ile  Phe  Ala
              1490                     1495                      1500

Pro  Phe  Ile  Phe  Asn  Pro  His  Gln  Phe  Ala  Trp  Glu  Asp  Phe  Phe  Leu
505                  1510                     1515                      1520

Asp  Tyr  Arg  Asp  Tyr  Ile  Arg  Trp  Leu  Ser  Arg  Gly  Asn  Asn  Lys  Tyr
              1525                     1530                      1535

His  Arg  Asn  Ser  Trp  Ile  Gly  Tyr  Val  Arg  Met  Ser  Arg  Ser  Arg  Val
              1540                     1545                      1550
```

```
Thr  Gly  Phe  Lys  Arg  Lys  Leu  Val  Gly  Asp  Glu  Ser  Glu  Lys  Ser  Ala
          1555                    1560                    1565

Gly  Asp  Ala  Ser  Arg  Ala  His  Arg  Thr  Asn  Leu  Ile  Met  Ala  Glu  Ile
     1570                    1575                    1580

Ile  Pro  Cys  Ala  Ile  Tyr  Ala  Ala  Gly  Cys  Phe  Ile  Ala  Phe  Thr  Phe
585                      1590                    1595                         1600

Ile  Asn  Ala  Gln  Thr  Gly  Val  Lys  Thr  Thr  Asp  Glu  Asp  Arg  Val  Asn
               1605                    1610                    1615

Ser  Thr  Leu  Arg  Ile  Ile  Ile  Cys  Thr  Leu  Ala  Pro  Ile  Val  Ile  Asp
               1620                    1625                    1630

Ile  Gly  Val  Leu  Phe  Phe  Cys  Met  Gly  Leu  Ser  Cys  Cys  Ser  Gly  Pro
               1635                    1640                    1645

Leu  Leu  Gly  Met  Cys  Cys  Lys  Thr  Gly  Ser  Val  Met  Ala  Gly  Ile
          1650                    1655                    1660

Ala  His  Gly  Ile  Ala  Val  Val  Val  His  Ile  Val  Phe  Phe  Ile  Val  Met
665                      1670                    1675                         1680

Trp  Val  Leu  Glu  Gly  Phe  Ser  Phe  Val  Arg  Met  Leu  Ile  Gly  Val  Val
               1685                    1690                    1695

Thr  Cys  Ile  Gln  Cys  Gln  Arg  Leu  Ile  Phe  His  Cys  Met  Thr  Val  Leu
               1700                    1705                    1710

Leu  Leu  Thr  Arg  Glu  Phe  Lys  Asn  Asp  His  Ala  Asn  Thr  Ala  Phe  Trp
          1715                    1720                    1725

Thr  Gly  Lys  Trp  Tyr  Ser  Thr  Gly  Leu  Gly  Tyr  Met  Ala  Trp  Thr  Gln
     1730                    1735                    1740

Pro  Thr  Arg  Glu  Leu  Thr  Ala  Lys  Val  Ile  Glu  Leu  Ser  Glu  Phe  Ala
745                      1750                    1755                         1760

Ala  Asp  Phe  Val  Leu  Gly  His  Val  Ile  Leu  Ile  Phe  Gln  Leu  Pro  Val
               1765                    1770                    1775

Ile  Cys  Ile  Pro  Lys  Ile  Asp  Lys  Phe  His  Ser  Ile  Met  Leu  Phe  Trp
               1780                    1785                    1790

Leu  Lys  Pro  Ser  Arg  Gln  Ile  Arg  Pro  Pro  Ile  Tyr  Ser  Leu  Lys  Gln
          1795                    1800                    1805

Ala  Arg  Leu  Arg  Lys  Arg  Met  Val  Arg  Arg  Tyr  Cys  Ser  Leu  Tyr  Phe
     1810                    1815                    1820

Leu  Val  Leu  Ile  Ile  Phe  Ala  Gly  Cys  Ile  Val  Gly  Pro  Ala  Val  Ala
825                      1830                    1835                         1840

Ser  Ala  His  Val  Pro  Lys  Asp  Leu  Gly  Ser  Gly  Leu  Thr  Gly  Thr  Phe
               1845                    1850                    1855

His  Asn  Leu  Val  Gln  Pro  Arg  Asn  Val  Ser  Asn  Asn  Asp  Thr  Gly  Ser
               1860                    1865                    1870

Gln  Met  Ser  Thr  Tyr  Lys  Ser  His  Tyr  Tyr  Thr  His  Thr  Pro  Ser  Leu
          1875                    1880                    1885

Lys  Thr  Trp  Ser  Thr  Ile  Lys
          1890                    1895
```

( 2 ) INFORMATION FOR SEQ ID NO:5:

( i ) SEQUENCE CHARACTERISTICS:
        ( A ) LENGTH: 2565 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
TACTGTATCG GTTTCAAGTC TGCTGCTCCC GAGTACACGC TTCGCACCCG TATTTGGTCC      60
TCGCTGCGTT CGCAAACTCT TTACAGAACT GTATCCGGGA TGATGAACTA TAGCAGAGCT     120
ATCAAGCTCC TCTACCGTGT GGAGAACCCG GAAGTCGTCC AGATGTTCGG TGGTAATTCT     180
GAGAAGCTGG AACATGAGCT CGAGAGGATG GCCCGTCGCA AGTTCAAGAT CTGTGTTTCA     240
ATGCAGCGGT ATGCCAAATT CACAAAAGAA GAACGTGAGA ACACAGAGTT CCTCCTCCGA     300
GCCTACCCCG ACCTGCAGAT TGCCTATCTC GATGAGGAAC CTCCAGCCAA CGAGGGTGAA     360
GAGCCGCGTC TCTACTCTGC TTTGATTGAT GGACACTGTG AGCTGCTCGA GAATGGCATG     420
CGGAAGCCCA AGTTCAGGAT CCAGCTCTCC GGAAACCCGA TCCTTGGTGA CGGCAAGTCT     480
GACAACCAAA ACCACTCGAT CATTTTCTAC CGCGGTGAAT ACATTCAGGT CATTGATGCC     540
AACCAAGACA ACTATCTCGA AGAGTGCTTG AAAATCCGAA GCGTTCTTGC TGAGTTTGAG     600
GAATTGACCA CCGACAATGT CTCGCCTTAC ACTCCTGGCG TTGCCTCTTC CTCTGAAGCT     660
CCTGTTGCTA TCCTTGGTGC CCGTGAATAC ATTTTCTCAG AGAACATTGG TGTACTTGGT     720
GACGTTGCCG CCGGTAAAGA ACAGACATTT GGTACCCTGT TTGCTCGTAC TCTTGCTCAG     780
ATTGGCGGAA AGCTCCATTA TGGTCACCCT GATTTCCTGA ATGGTATCTT CATGACTACC     840
AGAGGTGGTA TCTCCAAGGC TCAAAAAGGT CTACACCTTA ACGAGGATAT CTACGCTGGT     900
ATGAACGCCA TGGTTCGTGG TGGCCGCATC AAGCACTGCG AGTACTTCCA GTGTGGTAAG     960
GGTCGTGATC TTGGTTTCGG TTCCATTCTT AATTTCACCA CTAAGATTGG CACTGGTATG    1020
GGTGAGCAAA TGCTATCAAG AGAGTACTAC TACTKGGGTA CTCAACTGCC ACTCGACCGA    1080
TTCCTGTCCT TTTACTATGY TCACCCTGGA TTCCACATCA ACAACATGTT TATTATGTTG    1140
TCTGTGCAAA TGTTCATGAT TGTTCTGATC AACCTGGGGG CCCTGAAGCA CGAAACCATC    1200
AACTGCAACT ACAACTCCGA CCTGCCCATT ACCGATCCAC TTATGCCAAC GTTCTGCGCG    1260
CCTCTCACTC CTATCATCAA CTGGGTCAAC CGCTGTGTTA TTTCGATTTT CATCGTTTTC    1320
TTCATTTCGT TTGTTCCTTT GGCTGTTCAA GAATTGACTG AAAGAGGACT CTGGCGTATG    1380
GCAACGCGTC TGGCCAAACA TTTCGGATCT TTCTCCTTCA TGTTCGAGGT GTTTGTTTGT    1440
CAAATCTATT CCAACGCTGT GCACCAAAAC TTGTCTTTCG GTGGAGCGCG CTACATCGCT    1500
ACCGGTCGTG GTTTCGCAAC TGCTCGTATC CCATTCGGCG TTCTGTACTC TCGGTTTGCG    1560
GGACCTTCAA TTTACACCGG TTTCCGTCTG CTGATCATGC TGCTCTTCTC AACCTCAACT    1620
ACCTGGACTG CCTCTCTCAT TTGGTTCTGG GTCTCTCTTC TCGCCCTTTG CATCTCCCCA    1680
TTCCTTTTCA ACCCTCACCA GTTTGCCTGG AACGACTTCT TCATCGATTA CCGTGACTAC    1740
ATCCGATGGC TTTCGCGCGG TAACTCTCGC TCACACGCAT CCTCATGGAT TGGCTTCTGC    1800
CGTTTGTCGC GTACTCGGAT CACTGGTTAC AAGCGCAAGC TTCTCGGTGT GCCGTCGGAG    1860
AAAGGATCAG GTGACGTTCC CAGAGCTCGT ATTACCAACA TTTTCTTCAG CGAAATTGTC    1920
GCTCCTCTAG TCCTCGTTGC TGTTACCCTC GTTCCATACC TCTACATCAA TTCTCGGACT    1980
GGTGTGAGCG CTGATGTGGA CGGGGGCAAT GACCCTCACG ATGCCATTTT GCGTATTGCC    2040
ATTGTAGCAT TTGGACCTAT TGGTATCAAT GCCGGTGTTG CTGCTGTTTT CTTTGGTATG    2100
GCATGCTGCA TGGGTCCCAT CCTGAGCATG TGCTGCAAGA AGTTCGGTGC TGTGTTGGCG    2160
GCTATTGCCC ACGCGATTGC TGTGATCATC TTGCTTGTCA TCTTTGAAGT CATGTTCTTC    2220
CTCGAACACT GGTCTTGGCC CCGGTGCGTC ATGGGCATGA TCGCCATGGG TGCCATTCAA    2280
CGTTTCGTCT ACAAACTTAT TATCGCGCTC GCTCTTACCC GAGAGTTCAA GCATGACCAG    2340
TCGAACATCG CATGGTGGAC TGGAAAATGG TACAACATGG GTTGGGACTC TCTCTCTCAA    2400
```

-continued

```
CCGGGCCGAG AGTTCCTCTG CAAGATCACG GAGTTGGGCT ATTTCTCAGC AGACTTCGTC      2460

ATTGGTCATC TCCTATTGTT CATTATGCTG CCCGCTCTTT GTGTTCCTTA CATTGACAAG      2520

TTTCACTCAG YCATTCTCTT TTGGGTCCSG CCCAAGGTAA GAACC                     2565
```

( 2 ) INFORMATION FOR SEQ ID NO:6:

( i ) SEQUENCE CHARACTERISTICS:
        ( A ) LENGTH: 855 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:6:

```
Tyr Cys Ile Gly Phe Lys Ser Ala Ala Pro Glu Tyr Thr Leu Arg Thr
  1               5                  10                  15

Arg Ile Trp Ser Ser Leu Arg Ser Gln Thr Leu Tyr Arg Thr Val Ser
             20                  25                  30

Gly Met Met Asn Tyr Ser Arg Ala Ile Lys Leu Leu Tyr Arg Val Glu
         35                  40                  45

Asn Pro Glu Val Val Gln Met Phe Gly Gly Asn Ser Glu Lys Leu Glu
     50                  55                  60

His Glu Leu Glu Arg Met Ala Arg Arg Lys Phe Lys Ile Cys Val Ser
 65                  70                  75                  80

Met Gln Arg Tyr Ala Lys Phe Thr Lys Glu Glu Arg Glu Asn Thr Glu
                 85                  90                  95

Phe Leu Leu Arg Ala Tyr Pro Asp Leu Gln Ile Ala Tyr Leu Asp Glu
            100                 105                 110

Glu Pro Pro Ala Asn Glu Gly Glu Glu Pro Arg Leu Tyr Ser Ala Leu
        115                 120                 125

Ile Asp Gly His Cys Glu Leu Leu Glu Asn Gly Met Arg Lys Pro Lys
    130                 135                 140

Phe Arg Ile Gln Leu Ser Gly Asn Pro Ile Leu Gly Asp Gly Lys Ser
145                 150                 155                 160

Asp Asn Gln Asn His Ser Ile Ile Phe Tyr Arg Gly Glu Tyr Ile Gln
                165                 170                 175

Val Ile Asp Ala Asn Gln Asp Asn Tyr Leu Glu Glu Cys Leu Lys Ile
            180                 185                 190

Arg Ser Val Leu Ala Glu Phe Glu Glu Leu Thr Thr Asp Asn Val Ser
        195                 200                 205

Pro Tyr Thr Pro Gly Val Ala Ser Ser Glu Ala Pro Val Ala Ile
    210                 215                 220

Leu Gly Ala Arg Glu Tyr Ile Phe Ser Glu Asn Ile Gly Val Leu Gly
225                 230                 235                 240

Asp Val Ala Ala Gly Lys Glu Gln Thr Phe Gly Thr Leu Phe Ala Arg
                245                 250                 255

Thr Leu Ala Gln Ile Gly Gly Lys Leu His Tyr Gly His Pro Asp Phe
            260                 265                 270

Leu Asn Gly Ile Phe Met Thr Thr Arg Gly Gly Ile Ser Lys Ala Gln
        275                 280                 285

Lys Gly Leu His Leu Asn Glu Asp Ile Tyr Ala Gly Met Asn Ala Met
    290                 295                 300

Val Arg Gly Gly Arg Ile Lys His Cys Glu Tyr Phe Gln Cys Gly Lys
305                 310                 315                 320
```

-continued

| | | | | | | | | | | | | | | |
|---|---|---|---|---|---|---|---|---|---|---|---|---|---|---|
| Gly | Arg | Asp | Leu | Gly 325 | Phe | Gly | Ser | Ile | Leu 330 | Asn | Phe | Thr | Thr | Lys 335 | Ile |
| Gly | Thr | Gly | Met 340 | Gly | Glu | Gln | Met | Leu 345 | Ser | Arg | Glu | Tyr | Tyr 350 | Tyr | Xaa |
| Gly | Thr | Gln | Leu 355 | Pro | Leu | Asp | Arg | Phe 360 | Leu | Ser | Phe | Tyr | Tyr 365 | Xaa | His |
| Pro | Gly 370 | Phe | His | Ile | Asn | Asn 375 | Met | Phe | Ile | Met | Leu 380 | Ser | Val | Gln | Met |
| Phe 385 | Met | Ile | Val | Leu | Ile 390 | Asn | Leu | Gly | Ala | Leu 395 | Lys | His | Glu | Thr | Ile 400 |
| Asn | Cys | Asn | Tyr | Asn 405 | Ser | Asp | Leu | Pro | Ile 410 | Thr | Asp | Pro | Leu | Met 415 | Pro |
| Thr | Phe | Cys | Ala 420 | Pro | Leu | Thr | Pro | Ile 425 | Ile | Asn | Trp | Val | Asn 430 | Arg | Cys |
| Val | Ile | Ser 435 | Ile | Phe | Ile | Val | Phe 440 | Phe | Ile | Ser | Phe | Val 445 | Pro | Leu | Ala |
| Val | Gln 450 | Glu | Leu | Thr | Glu | Arg 455 | Gly | Leu | Trp | Arg | Met 460 | Ala | Thr | Arg | Leu |
| Ala 465 | Lys | His | Phe | Gly | Ser 470 | Phe | Ser | Phe | Met | Phe 475 | Glu | Val | Phe | Val | Cys 480 |
| Gln | Ile | Tyr | Ser | Asn 485 | Ala | Val | His | Gln | Asn 490 | Leu | Ser | Phe | Gly | Gly 495 | Ala |
| Arg | Tyr | Ile | Ala | Thr 500 | Gly | Arg | Gly | Phe 505 | Ala | Thr | Ala | Arg | Ile 510 | Pro | Phe |
| Gly | Val | Leu 515 | Tyr | Ser | Arg | Phe | Ala 520 | Gly | Pro | Ser | Ile | Tyr 525 | Thr | Gly | Phe |
| Arg | Leu 530 | Leu | Ile | Met | Leu | Leu 535 | Phe | Ser | Thr | Ser | Thr 540 | Thr | Trp | Thr | Ala |
| Ser 545 | Leu | Ile | Trp | Phe | Trp 550 | Val | Ser | Leu | Leu | Ala 555 | Leu | Cys | Ile | Ser | Pro 560 |
| Phe | Leu | Phe | Asn | Pro 565 | His | Gln | Phe | Ala | Trp 570 | Asn | Asp | Phe | Phe | Ile 575 | Asp |
| Tyr | Arg | Asp | Tyr 580 | Ile | Arg | Trp | Leu | Ser 585 | Arg | Gly | Asn | Ser | Arg 590 | Ser | His |
| Ala | Ser | Ser 595 | Trp | Ile | Gly | Phe | Cys 600 | Arg | Leu | Ser | Arg | Thr 605 | Arg | Ile | Thr |
| Gly 610 | Tyr | Lys | Arg | Lys | Leu 615 | Leu | Gly | Val | Pro | Ser 620 | Glu | Lys | Gly | Ser | Gly |
| Asp 625 | Val | Pro | Arg | Ala | Arg 630 | Ile | Thr | Asn | Ile | Phe 635 | Phe | Ser | Glu | Ile | Val 640 |
| Ala | Pro | Leu | Val | Leu 645 | Val | Ala | Val | Thr | Leu 650 | Val | Pro | Tyr | Leu | Tyr 655 | Ile |
| Asn | Ser | Arg | Thr 660 | Gly | Val | Ser | Ala | Asp 665 | Val | Asp | Gly | Gly | Asn 670 | Asp | Pro |
| His | Asp | Ala 675 | Ile | Leu | Arg | Ile | Ala 680 | Ile | Val | Ala | Phe | Gly 685 | Pro | Ile | Gly |
| Ile | Asn 690 | Ala | Gly | Val | Ala | Ala 695 | Val | Phe | Phe | Gly | Met 700 | Ala | Cys | Cys | Met |
| Gly 705 | Pro | Ile | Leu | Ser | Met 710 | Cys | Cys | Lys | Lys | Phe 715 | Gly | Ala | Val | Leu | Ala 720 |
| Ala | Ile | Ala | His | Ala 725 | Ile | Ala | Val | Ile | Ile 730 | Leu | Leu | Val | Ile | Phe 735 | Glu |
| Val | Met | Phe | Phe 740 | Leu | Glu | His | Trp | Ser 745 | Trp | Pro | Arg | Cys | Val 750 | Met | Gly |

| | | | | | | | | | | | | | | |
|---|---|---|---|---|---|---|---|---|---|---|---|---|---|---|
|Met|Ile|Ala|Met|Gly|Ala|Ile|Gln|Arg|Phe|Val|Tyr|Lys|Leu|Ile|Ile|
| | |755| | | | |760| | | |765| | | |
|Ala|Leu|Ala|Leu|Thr|Arg|Glu|Phe|Lys|His|Asp|Gln|Ser|Asn|Ile|Ala|
| | |770| | | |775| | | |780| | | | |
|Trp|Trp|Thr|Gly|Lys|Trp|Tyr|Asn|Met|Gly|Trp|Asp|Ser|Leu|Ser|Gln|
|785| | | | |790| | | |795| | | | | |800|
|Pro|Gly|Arg|Glu|Phe|Leu|Cys|Lys|Ile|Thr|Glu|Leu|Gly|Tyr|Phe|Ser|
| | | | |805| | | |810| | | | |815| |
|Ala|Asp|Phe|Val|Ile|Gly|His|Leu|Leu|Leu|Phe|Ile|Met|Leu|Pro|Ala|
| | | |820| | | | |825| | | |830| | |
|Leu|Cys|Val|Pro|Tyr|Ile|Asp|Lys|Phe|His|Ser|Xaa|Ile|Leu|Phe|Trp|
| | |835| | | |840| | | | |845| | | |
|Val|Xaa|Pro|Lys|Val|Arg|Thr|
| |850| | | | |855|

( 2 ) INFORMATION FOR SEQ ID NO:7:

( i ) SEQUENCE CHARACTERISTICS:
        ( A ) LENGTH: 2069 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
|GGTACCATCT|ACTGGATGTA|CACTGCTTAC|AACTCCCCAA|CCTTGTATAC|TAAACATTAT|60|
|GTCCAAACCA|TAAATCAACA|ACCACTTGCT|TCGTCAAGAT|GGGCTGCTTG|TGCCATTGGT|120|
|GGTGTTCTTG|CTTCATTTAT|TCAAATTCTT|GCCACACTTT|TCGAATGGAT|TTTCGTGCCT|180|
|AGAGAATGGG|CCGGTGCTCA|ACATTTGAGT|CGTCGTATGC|TATTTTTGGT|GTTAATTTTC|240|
|TTACTCAATT|TGGTTCCACC|AGTTTATACA|TTCCAAATTA|CCAAATTGGT|GATTTATTCG|300|
|AAATCGGCAT|ATGCTGTGTC|GATTGTTGGA|TTTTTCATTG|CTGTGGCCAC|TTTAGTATTC|360|
|TTTGCCGTCA|TGCCATTGGG|TGGTTTATTC|ACTTCATACA|TGAACAAGAG|ATCAAGAAGA|420|
|TATATTGCAT|CACAAACATT|TACTGCCAAC|TACATTAAAT|GAAAGGTTT|AGATATGTGG|480|
|ATGTCTTATT|TGTTATGGTT|TTTGGTTTTC|CTTGCCAAAT|TGGTTGAATC|TTATTTCTTC|540|
|TTGACTTTGT|CTTTAAGAGA|TCCTATTAGA|AACTTGTCGA|CCATGACAAT|GAGATGTGTT|600|
|GGTGAAGTTT|GGTACAAAGA|TATTGTTTGT|AGAAACCAAG|CCAAGATTGT|CTTGGGGTTG|660|
|ATGTATCTTG|TTGATTTGTT|ATTGTTCTTT|TGGATACTT|ATATGTGGTA|CATTATTTGT|720|
|AACTGTATCT|TCTCCATTGG|TCGTTCATTC|TATTTGGGTA|TTTCCATTTT|GACTCCTTGG|780|
|AGAAACATTT|TCACCAGATT|GCCAAAGAGA|ATTTATTCCA|AGATTTTAGC|TACCACGGAA|840|
|ATGGAAATCA|AATATAAACC|TAAAGTTTTG|ATTTCACAAA|TTTGGAATGC|CATTGTTATT|900|
|TCCATGTACA|GAGAACACTT|GTTAGCCATT|GATCACGTTC|AAAAATTATT|GTATCATCAA|960|
|GTCCCATCTG|AAATTGAAGG|TAAGAGAACT|TTGAGAGCTC|CAACTTTCTT|TGTTTCTCAA|1020|
|GATGACAACA|ATTTTGAAAC|GGAATTTTTC|CCAAGAAATT|CTGAAGCTGA|AGAAGAATT|1080|
|TCATTTTTCG|CTCAATCTTT|GGCTACACCA|ATGCCAGAAC|CATTACCAGT|TGATAATATG|1140|
|CCAACTTTTA|CTGTTTTTAC|TCCTCATTAT|TCGGAAAAGA|TTTTGTTATC|TTTGAGAGAA|1200|
|ATCATTAGAG|AAGATGATCA|ATTCTCAAGA|GTGACATTAT|GGAATATTT|GAAACAATTA|1260|
|CATCCAGTTG|AATGGGATTG|TTTTGTTAAG|GACACCAAGA|TTTTGGCTGA|AGAAACTGCT|1320|
|GCTTATGAAA|ATGGTGATGA|TTCTGAAAAA|TTATCTGAAG|ATGGATTGAA|ATCCAAGATT|1380|

-continued

```
GATGATTTAC CATTCTATTG TATTGGTTTC AAGTCTGCCG CCCCTGAATA TACTTTAAGA   1440
ACAAGAATTT GGGCTTCATT GAGATCCCAA ACTTTGTACA GAACTGTATC TGGGTTTATG   1500
AATTATGCCA GAGCCATTAA ATTGTTATAC AGAGTGGAAA ACCCAGAATT GGTTCAATAT   1560
TTCGGTGGTG ATCCTGAAGG ATTAGAATTA GCTTTAGAAA GAATGGCCAG AAGAAAGTTT   1620
AGATTTTTGG TTTCTATGCA AAGATTGTCT AAATTCAAAG ATGATGAAAT GGAAATGCT    1680
GAGTTCTTAT TGCGTGCTTA CCCTGATTTG CAAATTGCTT ACTTGGATGA AGAACCGGCT   1740
TTGAATGAGG ACGAGGAACC AAGAGTATAC TCTGCCTTGA TTGATGGTCA TTGTGAAATG   1800
TTAGAAAATG GTAGACGTCG TCCTAAATTC AGAGTTCAAT TGTCTGGTAA TCCAATTTTG   1860
GGTGATGGTA AATCTGATAA TCAAATCAT GCGGTTATTT TCCATAGAGG TGAATATATT    1920
CAATTGATTG ATGCTAATCA AGATAATTAT TTGGAAGAAT GTTTGAAGAT TAGATCAGTT   1980
TTGGCTGAAT TTGAAGAAAT GAATGTTGAA CATGTTAATC CATATGCACC AAATTTGAAA   2040
TCTGAAGATA ATAACACCAA GAAGGATCC                                    2069
```

( 2 ) INFORMATION FOR SEQ ID NO:8:

( i ) SEQUENCE CHARACTERISTICS:
        ( A ) LENGTH: 690 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

```
Gly Thr Ile Tyr Trp Met Tyr Thr Ala Tyr Asn Ser Pro Thr Leu Tyr
 1               5                  10                  15
Thr Lys His Tyr Val Gln Thr Ile Asn Gln Gln Pro Leu Ala Ser Ser
            20                  25                  30
Arg Trp Ala Ala Cys Ala Ile Gly Gly Val Leu Ala Ser Phe Ile Gln
        35                  40                  45
Ile Leu Ala Thr Leu Phe Glu Trp Ile Phe Val Pro Arg Glu Trp Ala
    50                  55                  60
Gly Ala Gln His Leu Ser Arg Arg Met Leu Phe Leu Val Leu Ile Phe
65                  70                  75                  80
Leu Leu Asn Leu Val Pro Pro Val Tyr Thr Phe Gln Ile Thr Lys Leu
                85                  90                  95
Val Ile Tyr Ser Lys Ser Ala Tyr Ala Val Ser Ile Val Gly Phe Phe
            100                 105                 110
Ile Ala Val Ala Thr Leu Val Phe Phe Ala Val Met Pro Leu Gly Gly
        115                 120                 125
Leu Phe Thr Ser Tyr Met Asn Lys Arg Ser Arg Arg Tyr Ile Ala Ser
    130                 135                 140
Gln Thr Phe Thr Ala Asn Tyr Ile Lys Leu Lys Gly Leu Asp Met Trp
145                 150                 155                 160
Met Ser Tyr Leu Leu Trp Phe Leu Val Phe Leu Ala Lys Leu Val Glu
                165                 170                 175
Ser Tyr Phe Phe Leu Thr Leu Ser Leu Arg Asp Pro Ile Arg Asn Leu
            180                 185                 190
Ser Thr Met Thr Met Arg Cys Val Gly Glu Val Trp Tyr Lys Asp Ile
        195                 200                 205
Val Cys Arg Asn Gln Ala Lys Ile Val Leu Gly Leu Met Tyr Leu Val
    210                 215                 220
```

| Asp | Leu | Leu | Leu | Phe | Phe | Leu | Asp | Thr | Tyr | Met | Trp | Tyr | Ile | Ile | Cys |
| 225 | | | | 230 | | | | 235 | | | | | | | 240 |
| Asn | Cys | Ile | Phe | Ser | Ile | Gly | Arg | Ser | Phe | Tyr | Leu | Gly | Ile | Ser | Ile |
| | | | | 245 | | | | 250 | | | | | 255 | | |
| Leu | Thr | Pro | Trp | Arg | Asn | Ile | Phe | Arg | Leu | Pro | Lys | Arg | Ile | Tyr | |
| | | | 260 | | | | 265 | | | | | 270 | | | |
| Ser | Lys | Ile | Leu | Ala | Thr | Thr | Glu | Met | Glu | Ile | Lys | Tyr | Lys | Pro | Lys |
| | | 275 | | | | | 280 | | | | | 285 | | | |
| Val | Leu | Ile | Ser | Gln | Ile | Trp | Asn | Ala | Ile | Val | Ile | Ser | Met | Tyr | Arg |
| 290 | | | | | 295 | | | | | 300 | | | | | |
| Glu | His | Leu | Leu | Ala | Ile | Asp | His | Val | Gln | Lys | Leu | Leu | Tyr | His | Gln |
| 305 | | | | | 310 | | | | | 315 | | | | | 320 |
| Val | Pro | Ser | Glu | Ile | Glu | Gly | Lys | Arg | Thr | Leu | Arg | Ala | Pro | Thr | Phe |
| | | | | 325 | | | | | 330 | | | | | 335 | |
| Phe | Val | Ser | Gln | Asp | Asp | Asn | Asn | Phe | Glu | Thr | Glu | Phe | Phe | Pro | Arg |
| | | | 340 | | | | | 345 | | | | | 350 | | |
| Asn | Ser | Glu | Ala | Glu | Arg | Arg | Ile | Ser | Phe | Phe | Ala | Gln | Ser | Leu | Ala |
| | | 355 | | | | | 360 | | | | | 365 | | | |
| Thr | Pro | Met | Pro | Glu | Pro | Leu | Pro | Val | Asp | Asn | Met | Pro | Thr | Phe | Thr |
| | 370 | | | | | 375 | | | | | 380 | | | | |
| Val | Phe | Thr | Pro | His | Tyr | Ser | Glu | Lys | Ile | Leu | Leu | Ser | Leu | Arg | Glu |
| 385 | | | | | 390 | | | | | 395 | | | | | 400 |
| Ile | Ile | Arg | Glu | Asp | Asp | Gln | Phe | Ser | Arg | Val | Thr | Leu | Leu | Glu | Tyr |
| | | | | 405 | | | | | 410 | | | | | 415 | |
| Leu | Lys | Gln | Leu | His | Pro | Val | Glu | Trp | Asp | Cys | Phe | Val | Lys | Asp | Thr |
| | | | 420 | | | | | 425 | | | | | 430 | | |
| Lys | Ile | Leu | Ala | Glu | Glu | Thr | Ala | Ala | Tyr | Glu | Asn | Gly | Asp | Asp | Ser |
| | | | 435 | | | | 440 | | | | | 445 | | | |
| Glu | Lys | Leu | Ser | Glu | Asp | Gly | Leu | Lys | Ser | Lys | Ile | Asp | Asp | Leu | Pro |
| | 450 | | | | | 455 | | | | | 460 | | | | |
| Phe | Tyr | Cys | Ile | Gly | Phe | Lys | Ser | Ala | Ala | Pro | Glu | Tyr | Thr | Leu | Arg |
| 465 | | | | | 470 | | | | 475 | | | | | | 480 |
| Thr | Arg | Ile | Trp | Ala | Ser | Leu | Arg | Ser | Gln | Thr | Leu | Tyr | Arg | Thr | Val |
| | | | | 485 | | | | | 490 | | | | | | 495 |
| Ser | Gly | Phe | Met | Asn | Tyr | Ala | Arg | Ala | Ile | Lys | Leu | Leu | Tyr | Arg | Val |
| | | | 500 | | | | | 505 | | | | | 510 | | |
| Glu | Asn | Pro | Glu | Leu | Val | Gln | Tyr | Phe | Gly | Gly | Asp | Pro | Glu | Gly | Leu |
| | | 515 | | | | | 520 | | | | | 525 | | | |
| Glu | Leu | Ala | Leu | Glu | Arg | Met | Ala | Arg | Arg | Lys | Phe | Arg | Phe | Leu | Val |
| | | 530 | | | | 535 | | | | | 540 | | | | |
| Ser | Met | Gln | Arg | Leu | Ser | Lys | Phe | Lys | Asp | Asp | Glu | Met | Glu | Asn | Ala |
| 545 | | | | | 550 | | | | 555 | | | | | | 560 |
| Glu | Phe | Leu | Leu | Arg | Ala | Tyr | Pro | Asp | Leu | Gln | Ile | Ala | Tyr | Leu | Asp |
| | | | | 565 | | | | 570 | | | | | | 575 | |
| Glu | Glu | Pro | Ala | Leu | Asn | Glu | Asp | Glu | Pro | Arg | Val | Tyr | Ser | Ala | |
| | | | 580 | | | | 585 | | | | | 590 | | | |
| Leu | Ile | Asp | Gly | His | Cys | Glu | Met | Leu | Glu | Asn | Gly | Arg | Arg | Pro | |
| | | 595 | | | | | 600 | | | | | 605 | | | |
| Lys | Phe | Arg | Val | Gln | Leu | Ser | Gly | Asn | Pro | Ile | Leu | Gly | Asp | Gly | Lys |
| | 610 | | | | | 615 | | | | | 620 | | | | |
| Ser | Asp | Asn | Gln | Asn | His | Ala | Val | Ile | Phe | His | Arg | Gly | Glu | Tyr | Ile |
| 625 | | | | | 630 | | | | | 635 | | | | | 640 |
| Gln | Leu | Ile | Asp | Ala | Asn | Gln | Asp | Asn | Tyr | Leu | Glu | Glu | Cys | Leu | Lys |
| | | | | 645 | | | | | 650 | | | | | 655 | |

```
Ile  Arg  Ser  Val  Leu  Ala  Glu  Phe  Glu  Met  Asn  Val  Glu  His  Val
               660                 665                     670

Asn  Pro  Tyr  Ala  Pro  Asn  Leu  Lys  Ser  Glu  Asp  Asn  Thr  Lys  Lys
               675                 680                     685

Asp  Pro
     690
```